US012214066B2

(12) United States Patent
Shoseyov et al.

(10) Patent No.: US 12,214,066 B2
(45) Date of Patent: Feb. 4, 2025

(54) HAIR CARE COMPOSITIONS

(71) Applicants: Yissum Research Development Company of the Hebrew University of Jerusalem Ltd., Jerusalem (IL); Smart Resilin Ltd., Karmei Yosef (IL)

(72) Inventors: Oded Shoseyov, Shoham (IL); Roni Shalev, Moshav Timorim (IL); Sigal Baruch-Sharon, Ness-Ziona (IL); Tal Ben Shalom, Beer-Yaacov (IL); Liron Nuttman-Nesial, Rechovot (IL)

(73) Assignees: YISSUM RESEARCH DEVELOPMENT COMPANY OF THE HEBREW UNIVERSITY OF JERUSALEM LTD., Jerusalem (IL); SMART RESILIN LTD., Karmei Yosef (IL)

( * ) Notice: Subject to any disclaimer, the term of this patent is extended or adjusted under 35 U.S.C. 154(b) by 0 days.

(21) Appl. No.: 16/603,280

(22) PCT Filed: Apr. 4, 2018

(86) PCT No.: PCT/IL2018/050399
§ 371 (c)(1),
(2) Date: Oct. 7, 2019

(87) PCT Pub. No.: WO2018/185768
PCT Pub. Date: Oct. 11, 2018

(65) Prior Publication Data
US 2020/0121581 A1    Apr. 23, 2020

Related U.S. Application Data

(60) Provisional application No. 62/482,910, filed on Apr. 7, 2017.

(51) Int. Cl.
*A61K 8/64* (2006.01)
*A61K 8/73* (2006.01)
*A61Q 5/06* (2006.01)

(52) U.S. Cl.
CPC .............. *A61K 8/64* (2013.01); *A61K 8/731* (2013.01); *A61Q 5/06* (2013.01)

(58) Field of Classification Search
None
See application file for complete search history.

(56) References Cited

U.S. PATENT DOCUMENTS

2010/0015070 A1   1/2010  Bollschweiler et al.
2011/0180093 A1*  7/2011  Verboom ................. A61Q 5/06
                                                    132/203

(Continued)

FOREIGN PATENT DOCUMENTS

BR    102012008730 A2 *  8/2015  .............. A61K 8/11
WO   WO-2008055931 A1 *  5/2008  ............. A61Q 17/04

(Continued)

OTHER PUBLICATIONS

Linder. Journal of Biotechnology 57 (1997) 15-28.*

(Continued)

*Primary Examiner* — Nicole P Babson
*Assistant Examiner* — Lori K Mattison
(74) *Attorney, Agent, or Firm* — FISHERBROYLES, LLP; Roger L. Browdy

(57) ABSTRACT

Provided are methods, compositions and kits employing cellulose nanocrystals for hair-straightening treatment. Also provided are methods, compositions and kits employing a resilin, for hair-straightening treatment and/or for maintenance of straightened hair following a hair-straightening treatment.

8 Claims, 18 Drawing Sheets

Specification includes a Sequence Listing.

(56) References Cited

U.S. PATENT DOCUMENTS

| | | |
|---|---|---|
| 2012/0125358 A1 | 5/2012 | Hawkins et al. |
| 2012/0148517 A1 | 6/2012 | Gilmore et al. |
| 2012/0186596 A1 | 7/2012 | Xavier et al. |
| 2014/0037816 A1* | 2/2014 | Bakeev ............... C08L 1/284 |
| | | 426/564 |
| 2014/0083416 A1* | 3/2014 | Nuopponen ............ C08B 15/02 |
| | | 127/29 |

FOREIGN PATENT DOCUMENTS

| | | | | |
|---|---|---|---|---|
| WO | WO 2009/069123 | | 6/2009 | |
| WO | WO-2012027369 A2 * | | 3/2012 | ............... A61K 8/23 |
| WO | WO 2013/030840 | | 3/2013 | |
| WO | WO 2015/068160 | | 5/2015 | |
| WO | WO 2016/015148 | | 2/2016 | |
| WO | WO-2017040876 A1 * | | 3/2017 | ............... A61K 8/06 |
| WO | WO-2017041903 A1 * | | 3/2017 | ............... A61K 8/46 |
| WO | WO 2018/185768 | | 10/2018 | |

OTHER PUBLICATIONS

BR 102012008730 Eng Tran. Published: Aug. 2015.*

Cathe Forums. https://cathe.com/forum/threads/how-long-does-your-shampoo-last.207546/. Published: Jul. 23, 2005.*

Minguet. https://onlinelibrary.wiley.com/doi/epdf/10.1111/j.1468-2494.2009.00566.x. International Journal of Cosmetic Science, 2010, 32, 246-257.*

Chakravorty. https://vedix.com/blogs/articles/hair-straightening. Published: Aug. 4, 2022.*

Flora. https://web.archive.org/web/20160730034340/http://chemeng.uwaterloo.ca/mtam/flora.html. Published: Jul. 30, 2016.*

Notification About Necessity to Submit Additional Materials Dated Feb. 17, 2021 From The Eurasian Patent Organization, The Eurasian Patent Office Re. 201992400 and Its Summary in English. (4 Pages).

Office Action Dated Jun. 3, 2021 From the Israel Patent Office Re. Application No. 269898 and Its Translation Into English. (6 Pages).

Translation Dated Mar. 24, 2021 of Requirement to Furnish Additional Materials Dated Feb. 17, 2021 From The Eurasian Patent Organization, The Eurasian Patent Office Re. 201992400 and Its Summary in English. (2 Pages).

Communication Pursuant to Article 94(3) EPC Dated Jul. 20, 2020 From the European Patent Office Re. Application No. 18723987.6. (8 Pages).

International Preliminary Report on Patentability Dated Oct. 17, 2019 From the International Bureau of WIPO Re. Application No. PCT/IL2018/050399. (11 Pages).

International Search Report and the Written Opinion Dated Jul. 9, 2018 From the International Searching Authority Re. Application No. PCT/IL2018/050399. (19 Pages).

Andersen "The Cross-Links in Resilin Identified as Dityrosine and Trityrosine", Biochimica et Biophysica Acta, 93(1): 213-215, Oct. 9, 1964.

Ardell et al. "Tentative Identification of A Resilin Gene in *Drosophila Melanogaster*", Insect Biochemistry and Molecular Biology, XP002998361, 31(10): 965-970, Sep. 2001.

Elvin et al. "Synthesis and Properties of Crosslinked Recombinant Pro-Resilin", Nature, 437(7061): 999-1002, Oct. 13, 2005.

Feughelman "A Note on the Permanent Setting of Human Hair", Journal of the Society of the Cosmetic Chemists, 41(3): 209-212, May/Jun. 1990.

Kharin et al. "Optical Properties of the Medulla and the Cortex of Human Scalp Hair", Journal of Biomedical Optics, 14(2): 024035-1-024035-7, Published Online Apr. 13, 2009.

Miranda-Vilela et al. "An Overview of Chemical Straightening of Human Hair: Technical Aspects, Potential Rsiks to Hair Fibre and Health and Legal Issues", International Journal of Cosmetic Science, 36(1): 2-11, Feb. 2014.

Qin et al. "Expression, Cross-Linking, and Characterization of Recombinant Chitin Binding Resilin", Biomacromolecules, 10: 3227-3234, Published on Web Nov. 23, 2009.

Qin et al. "Recombinant Exon-Encoded Resilins for Elastomeric Biomaterials", Biomaterials, 32: 9231-9243, Available Online Sep. 29, 2011.

Rivkin et al. "Bionanocomposite Films From Resilin-CBD Bound to Cellulose Nanocrystals", Industrial Biotechnology, 1191): 44-58, Feb. 2015.

Sakurada et al. "Experimental Determination of the Elastic Modulus of Crystalline Regions in Oriented Polymers", Journal of Polymer Science, 57(165): 651-660, Mar. 1962.

Shoseyov et al. "Carbohydrate Binding Modules: Biochemical Properties and Novel Applications", Microbiology and Molecular Biology Reviews, 70(2): 283-295, Jun. 2006.

Spaniol Abraham et al. "Hair Care: A Medical Overview (Part 2)", Surgical & Cosmetic Dermatology, 1(4): 178-185, 2009.

Verker et al. "Insertion of Nano-Crystaline Cellulose Into Epoxy Resin Via Resilin to Construct A Novel Elastic Adhesive", Cellulose, 21(6): 4369-4379, Published Online Sep. 30, 2014.

Weis-Fogh "Molecular Interpretation of the Elasticity of Resilin, A Rubber-Like Protein", Journal of Molecular Biology, 3(5): 648-667, Oct. 1961.

Weis-Fogh "Thermodynamic Properties of Resilin, A Rubber-Like Protein", Journal of Molecular Biology, 3(5): 520-531, Oct. 1961.

Wolfram "Human Hair: A Unique Physicochemical Composite", Journal of the American Academy of Dermatology, 48(6): S106-S114, Jun. 2003.

Wong et al. "Mechanism of Hair Straightening", Journal of the Society of Cosmetic Chemists, 45(6): 347-352, Nov./Dec. 1994.

Examination Report Dated Apr. 26, 2022 From the Servico Publico Federal, Ministerio da Economia, Instituto Nacional da Propriedade Industrial do Brasil RE Application No. BR11 2019 020980 8 and its Translation into English . (4 Pages).

Habibi et al. "Cellulose Nanocrystals: Chemistry, Self-Assembly, and Applications", Chemical Reviews, 110(6): 3479-3500, Published on Web Mar. 4, 2010.

Communication Pursuant to Article 94(3) EPC Dated Sep. 30, 2022 From the European Patent Office Re. Application No. 18723987.6. (4 Pages).

English Translation Dated Nov. 29, 2021 of Notification About Necessity to Submit Additional Materials Dated Nov. 8, 2021 From The Eurasian Patent Organization, The Eurasian Patent Office Re. Apllication No. 201992400. (8 Pages).

Notification About Necessity to Submit Additional Materials Dated Nov. 8, 2021 From The Eurasian Patent Organization, The Eurasian Patent Office Re. Apllication No. 201992400. (8 Pages).

Tsybulya et al. "Physical Methods of Solid State Study", Ministry of Education of the Russian Federation ovosibirisk State University, Department of General Physics Specialization, 2P., 2008. Translation.

* cited by examiner

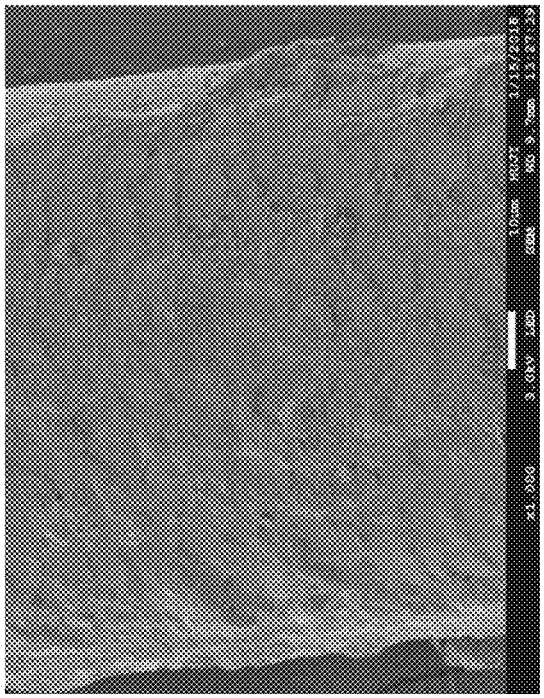
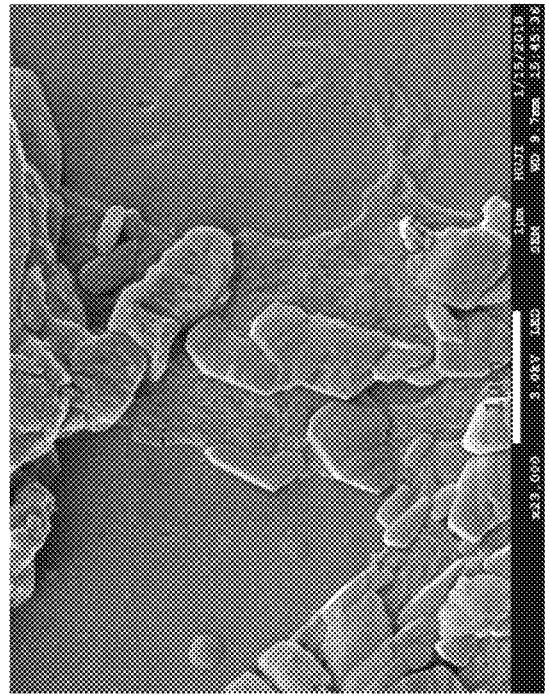
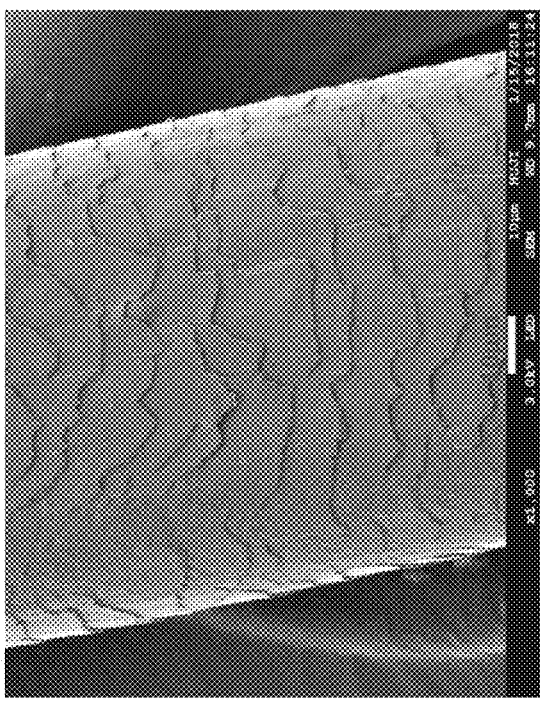
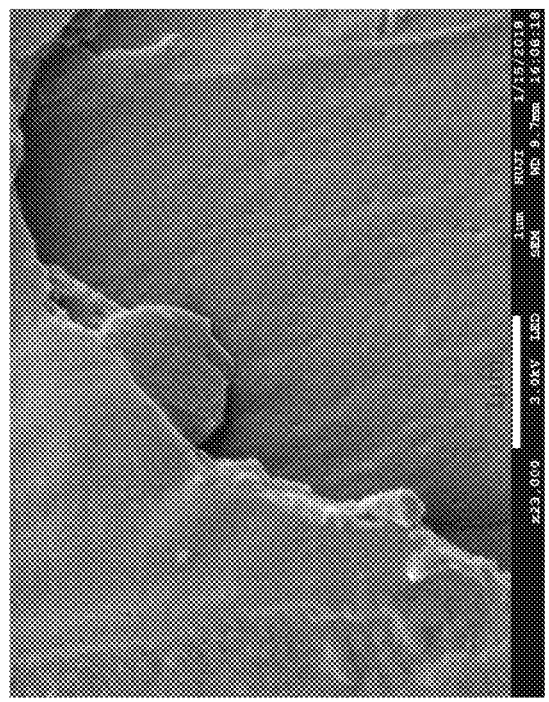
FIG. 23A
FIG. 23B
FIG. 23C
FIG. 23D

HAIR CARE COMPOSITIONS

RELATED APPLICATIONS

This application is a National Phase of PCT Patent Application No. PCT/IL2018/050399 having International filing date of Apr. 4, 2018, which claims the benefit of priority under 35 USC § 119(e) of U.S. Provisional Patent Application No. 62/482,910 filed on Apr. 7, 2017. The contents of the above applications are all incorporated by reference as if fully set forth herein in their entirety.

SEQUENCE LISTING STATEMENT

The ASCII file, entitled 79682SequenceListing.txt, created on Oct. 7, 2019, comprising 61,563 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to cosmetics, more particularly, but not exclusively, to compositions and treatments useful in straightening hair.

Having a full, healthy and manageable head of hair is a common concern of men and women. Other than the number of hair fibers on a person's head, a full head of natural, healthy, manageable hair depends on the diameter and cross sectional area of the hair fibers, as well as various mechanical properties thereof. Hair fibers (about 50-100 µm in diameter) are not continuous in their entire length, but rather the result of the combination of compact groups of cells within the follicle, from which originate three distinct layers: the cuticle, the cortex, and the medulla.

The cuticle is the outermost layer of a hair fiber which consists of flattened cells arranged in an overlapping fashion, from about 6 to 12 cells thick. The outermost layer of the cuticle is coated with a lipid substance that renders the outer surface of the hair hydrophobic. The overlapping cellular arrangement and the lipid coating confer barrier properties to the fiber and permit the cells to slide past each other as the fiber swells from within.

The cortex, immediately beneath the cuticle, consists of tightly packed, rod-like structures composed of melanin granules that pigment the shaft. The cortex accounts for about 80% of the hair mass of the hair fiber, and provides most of the mechanical strength of a hair fiber. Much of this strength is due to the crosslinking of cysteine residues in covalent disulfide bonds; but much of hair fiber strength, as well as other properties, are also due to an extensive network of hydrogen bonding.

The innermost layer of a hair fiber, the medulla, is a core of loosely packed, cube-like cells with small packets of air between them. The width of each layer, as well as that of the entire shaft, can vary significantly even along the same hair. In some shafts, the medulla may be discontinuous or entirely absent.

The hair appearance depends considerably on the health of the cuticle. When the cuticle is strong and healthy, hair appears to be strong and healthy. Intact and closed cuticle acts as a protective shield against harmful environmental elements; when cuticle scales are open (raised), substances can be deposited in their structure. Physical-chemical manipulation of the scales of the cuticle causes the appearance of hair to be changed, creating all kinds of different effects which can vary in softness, color and even texture. Thus, from a cosmetic point of view, the cuticle is a very important component of the hair fiber [Rieger, M. M., ed. Harry's Cosmetology. $8^{th}$ ed., Chemical Publishing Co Inc., New York (2000)]. The cortex also has considerable cosmetic importance, as its optical properties strongly affect the color and shine of hair fiber [Kharin et al., *J Biomed Optics* 2009, 14:1-7].

Hair types may be categorized into three large groups—African, Caucasian and Asian—which facilitates recognition of specific characteristics of each type of hair including color, curling and other parameters [Wolfram, *J Am Acad Dermatol* 2003, 48:S106-S114]. The amino acid composition of hair fibers is always the same and the ranges of their concentration overlap and do not appear to vary greatly with ethnicity. Moreover, apart from their ethnicity, all hair fibers have a high content of cysteine disulfide bonds, which contribute significantly to the stability of the fiber.

The natural shape and structural integrity of human hair depends, in part, on the orientation of disulfide bonds (cysteine-cysteine bonds) of keratin protein. In human hair, disulfide bonds contribute to tertiary and quaternary protein structure. It is generally thought that alteration of the disulfide bonds is necessary and/or useful to effect long term changes in the shape of hair.

Hair shaping treatments that do not rearrange the disulfide bonds result in changes in hair shape that last a relatively short time [Miranda-Vilela et al., *Int J Cosmet Sci* 2014, 36:2-11]. For example, the use of hairstyling products or physicochemical techniques such as dryer, flat iron and hot comb to style hair may create temporary straightening of the hair. However, the styled hair will return to its natural shape after a short time, as a result of exposure to moisture in the air or washing. The use of heat and moisture to straighten hair may break and reconfigure hydrogen bonds in the hair, but the disulfide bonds are not substantially affected. It is commonly believed that hydrogen bonds, by themselves, are insufficient to hold the shape of hair for a significant time, because the stronger disulfide bonds eventually force the hair to reassume its original shape.

Thus, a permanent straightening of the hair is commonly considered to involve the cleaving and reforming of a substantial number of disulfide bonds. Various chemical treatments for doing this are known in the literature. Depending on the straightening agent used, damage to the protein structure may be controlled to a more or less degree. That is, various types of protein structures of the treated hair may be broken down, or only a particular type of protein structure. For example, hair straightening products that alter primary structure do so by weakening and/or breaking the internal chemical bonds of hair protein amino acids. Regardless of where the protein structure is altered, effective straightening treatments cause natural curls to loosen and straighten. While some straightening agents may be more effective and/or efficient than others, the tradeoff is usually in the damage done to the hair and scalp, and the need for adjunct treatments to limit that damage. On the other hand, treatments which may be somewhat less damaging to the hair and scalp, may require a longer time to operate, or the application of significantly more product, or multiple applications to achieve a desired result.

Alkaline agents can stabilize straightened hair by altering primary structure, converting cysteine dimers to lanthionine, a monosulfide (thioether) analog of a cysteine disulfide dimer, in a process referred to as lanthionization [Bouillon & Wilkinson, J. The Science of Hair Care, 2nd edn. Taylor & Francis Group, New York, 2005; Wong et al., J Soc Cosmet Chem 1994, 45:347-352]. However, lanthionization weakens hair fibers and it is well known that repeated use of alkaline hair straightening products can damage hair considerably.

Sulfur-containing agents, such as ammonium thioglycolate, ammonium sulfite, ammonium bisulfite, sodium metabisulfite ($Na_2S_2O_5$) and cysteine, act via milder mechanism, by reducing disulfide bonds (—S—S—) to thiosulfate groups (—S—$SO_3^-$), also known as a Bunte salts. It has been reported that the formation of Bunte salts in hair treatment can be slowly reversed with water rinsing, to rebuild the disulfide bonds, or an oxidizing agent may be used to help form new disulfide bonds. Following reduction of disulfide bonds and application of mechanical stress, new disulfide bonds form in a new arrangement, stabilizing the desired conformation [Feughelman, J Soc Cosmet Chem 1990, 41:209-2120].

U.S. Patent Application Publication No. 2012/0186596 describes a use of a combination of transglutaminase and polylysine for hair straightening. The topically applied transglutaminase is reported to covalently bind the polylysine to glutamine in proteins near the hair surface, which results in a continuous film on the surface of the hair.

Cellulose nanocrystals (CNC) represent a bio-material made from cellulose, which can be obtained from waste streams such as those of paper mills and municipal sewage system sludge. In its almost pure form, CNC has a tiny crystalline molecular structure, with a 200-300 nm length and 10-20 nm width, and is about 10 times stronger than steel. CNC is a highly crystalline form of nanostructured cellulose; due to the high aspect ratio, CNC fibres are typically obtained by controlled acid hydrolysis, during which the amorphous regions of the cellulose are attacked and removed. Suitably modified CNC, including CNC hydrolyzed by $H_2SO_4$, self-assembles and forms nematic liquid crystals in solution [Sakurada et al., *J Polym Sci* 1962, 57:651-660].

Resilin is found in specialized cuticle regions in many insects, and displays unique mechanical properties that combine reversible deformation with very high resilience. The structure of resilin is essentially an amorphous, polymeric hydrogel held together via di- and tri-tyrosine cross-links [Qin et al., *Biomaterials* 2011, 32:9231-9243; Andersen, *Biochimica Biophysica Acta* 1964, 93:213-215], which imparts near perfect rubberiness. Qin et al. [*Biomacromolecules* 2009, 10:3227-3234] describe the cloning, expression and purification of resilin-chitin binding domain (6H-resilin ChBD) proteins, which lay the foundation for a resilin-cellulose binding domain (CBD) construct.

International Patent Applicant Publication WO2013/030840 describes elastomeric materials prepared from recombinant proteins comprising resilin with a chitin binding domain (resilin-ChBD) or with a cellulose binding domain (resilin-CBD), by cross-linking dihydroxyphenyl moieties. International Patent Applicant Publication WO 2015/068160 describes further artificially cross-linked elastomeric materials prepared from resilin-ChBD or resilin-CBD, as well as composite materials comprising resilin-CBD bound to nanocrystalline cellulose. Verker et al. [*Cellulose* 2014, 21:4369-4379] describes direct insertion of resilin-CBD bound to nanocrystalline cellulose into a hydrophobic epoxy matrix, giving a 50% improvement in the Young's modulus and a higher elasticity of the nanocomposite compared to the neat epoxy.

U.S. Patent Application Publication No. 2010/0015070 describes a use of resilin proteins in cosmetics, wherein the proteins comprise 1-100 repeat units with the consensus sequence SXXYGXP (SEQ ID NO: 20).

Additional background art includes Abraham et al. [*Sung Cosmet Dermatol* 2009, 1:178-185]; Ardell & Andersen [*Insect Biochem Mol Biol* 2001, 31:965-970]; Elvin et al. [*Nature* 2005, 437:999-1002]; Rivkin et al. [*Industrial Biotechnology* 2015, 11:144-158]; Shoseyov et al. [*Microbiol Mol Biol Rev* 2006, 70:283-295]; Weis-Fogh [*J Mol Biol* 1961, 3:520-531]; Weis-Fogh [*J Mol Biol* 1961, 3:648-667]; International Patent Applicant Publication WO2009/069123; and U.S. Patent Application Publication No. 2012/0125358.

SUMMARY OF THE INVENTION

According to an aspect of some embodiments of the present invention there is provided a method of straightening hair, the method comprising:
(a) applying at least one cationic agent to the hair and/or subjecting the hair to a plasma treatment;
(b) applying cellulose nanocrystals to the hair; and
(c) applying heat and pressure to the hair, at a degree sufficient to cause hair straightening without causing damage to hair,
thereby straightening the hair.

According to some of any of the embodiments described herein, the method further comprises, prior to (a), applying to the hair an agent capable of cleaving disulfide bonds in hair.

According to some of any of the embodiments described herein, the method further comprises applying resilin to the hair.

According to some of any of the embodiments described herein, the resilin is a modified resilin comprising a cellulose-binding domain (CBD).

According to some of any of the embodiments described herein, the method comprises applying at least a portion of the resilin to the hair subsequently to applying the hair-straightening composition.

According to some of any of the embodiments described herein, the applying of at least a portion of the resilin to the hair is effected at least one day subsequently to applying the hair-straightening composition.

According to some of any of the embodiments described herein, the applying of at least a portion of the resilin to the hair is effected at least one week after applying the hair-straightening composition.

According to some of any of the embodiments described herein, the applying of at least a portion of the resilin to the hair is effected on at least two different days.

According to some of any of the embodiments described herein, the applying of at least a portion of the resilin to the hair is effected on at least 5 different days.

According to some of any of the embodiments described herein, the applying of at least a portion of the resilin to the hair is effected during a time period in a range of from one week to two years after applying the hair-straightening composition.

According to some of any of the embodiments described herein, the method is for maintenance of straightened hair after each application of the hair-straightening composition and the heat and pressure.

According to an aspect of some embodiments of the present invention there is provided a hair-straightening composition comprising cellulose nanocrystals, and a carrier suitable for application to hair.

According to an aspect of some embodiments of the present invention there is provided a method for maintenance of straightened hair following a hair-straightening treatment, the method comprising applying resilin to the hair.

According to some of any of the embodiments described herein, the hair-straightening treatment comprises applying cellulose nanocrystals to the hair, for example, a treatment as described herein in any of the respective embodiments and any combination thereof.

According to some of any of the embodiments described herein, the resilin is a modified resilin comprising a cellulose-binding domain (CBD).

According to some of any of the embodiments described herein, the applying of resilin to the hair is effected on at least two different days.

According to some of any of the embodiments described herein, the applying of resilin to the hair is effected on at least 5 different days.

According to some of any of the embodiments described herein, the applying of resilin to the hair is effected at least one week after applying the hair-straightening composition.

According to some of any of the embodiments described herein, the applying of at least a portion of the resilin to the hair is effected during a time period in a range of from one week to two years after applying the hair-straightening composition.

According to an aspect of some embodiments of the present invention there is provided a hair-straightening composition comprising resilin, and a carrier suitable for application to hair.

According to some of any of the embodiments described herein, the composition is for maintenance of straightened hair following a hair-straightening treatment.

According to some of any of the embodiments described herein, the hair-straightening treatment comprises applying cellulose nanocrystals to the hair, for example, a treatment as described herein in any of the respective embodiments and any combination thereof.

According to some of any of the embodiments described herein, the resilin is a modified resilin comprising a cellulose-binding domain (CBD).

According to an aspect of some embodiments of the present invention there is provided a kit for straightening hair, the kit comprising, as separate containers:
a) a first container comprising cellulose nanocrystals, and a carrier suitable for application to hair; and
b) a second container comprising a pre-treatment composition comprising at least one cationic agent.

According to some of any of the embodiments described herein, the kit further comprises a third container comprising the composition comprising resilin and a carrier suitable for application to hair.

According to some of any of the embodiments described herein, the resilin is a modified resilin comprising a cellulose-binding domain (CBD).

According to some of any of the embodiments described herein, the kit further comprises a fourth container comprising an agent capable of cleaving disulfide bonds in hair.

According to an aspect of some embodiments of the present invention there is provided a kit for straightening and maintenance of hair, the kit comprising, as separate containers:
a) a first container comprising cellulose nanocrystals, and a carrier suitable for application to hair; and
b) a second container comprising resilin and a carrier suitable for application to hair.

According to some of any of the embodiments described herein, the resilin is a modified resilin comprising a cellulose-binding domain (CBD).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying images. With specific reference now to the images in detail, it is stressed that the particulars shown are by way of example and for purposes of illustrative discussion of embodiments of the invention. In this regard, the description taken with the images makes apparent to those skilled in the art how embodiments of the invention may be practiced.

In the drawings:

FIGS. 23A-E present scanning electron micrographic images of untreated hair sample at ×1000 magnification (FIG. 23A) and at ×23,000 magnification (FIG. 23B) and of the hair sample following sequential treatment with 1M cysteine in 100 mM MES pH 3.5, 0.5M arginine in 1% BTMS in DDW and 2% CNC containing 10:1 RES-CBD, at ×1000 magnification (FIG. 23C) and at ×23,000 magnification (FIG. 23D), and of a side incision of the treated hair sample at ×23,000 magnification (FIG. 23E).

DESCRIPTION OF SPECIFIC EMBODIMENTS OF THE INVENTION

Figure 1:
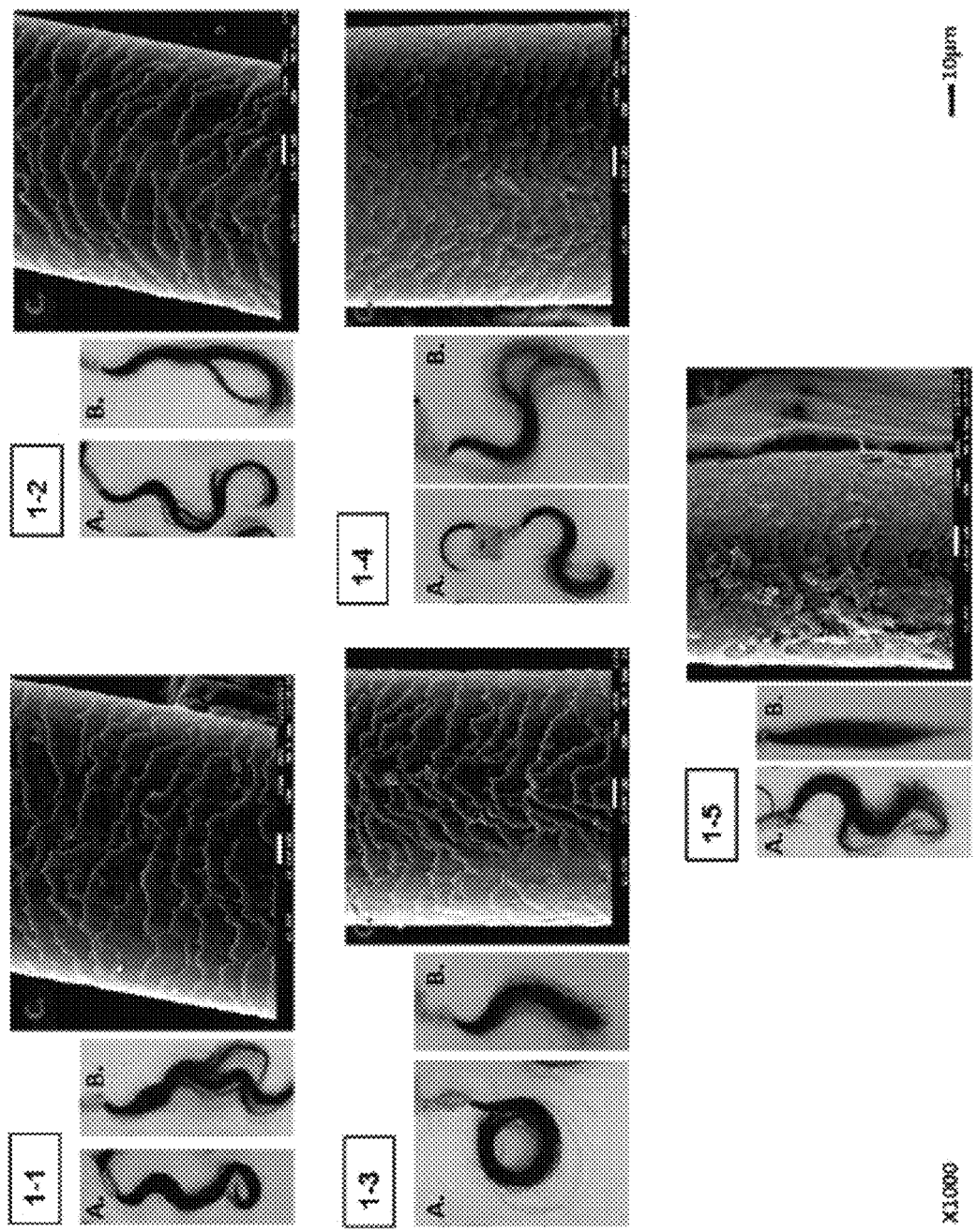
FIG. 1 presents photographic images of hair samples before (A) and after (B) treatment, and scanning electron micrographic images at ×1000 magnification (C) of the hair samples after a hair-straightening treatment using 5 mM SMBS+0.01% polylysine (Sample 1-1), 5 mM SMBS+polylysine+CNC (Sample 1-2), 0.5% SDS+1% NaCl+5 mM SMBS+0.5 M Cys+2% cetrimonium chloride (Sample 1-3), 0.5% SDS+1% NaCl (Sample 1-4), or 0.5% SDS+1% NaCl+5 mM SMBS+0.5 M Cys+2% cetrimonium chloride+CNC (Sample 1-5).

The present invention, in some embodiments thereof, relates to cosmetics, more particularly, but not exclusively, to compositions and treatments useful in straightening hair.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

The present inventors have uncovered that cellulose nanocrystals are surprisingly effective for use in straightening hair, and can enhance the efficacy of existing techniques for straightening hair.

While reducing the present invention to practice, the inventors have further uncovered that application of resilin to hair is surprisingly effective at enhancing and restoring the hair-straightening effect of treatments utilizing cellulose nanocrystals, even when applied many weeks after the original hair-straightening treatment.

Without being bound to any particular theory, it is believed that the cellulose nanocrystals affect the hair by forming a rigid or semi-rigid film, long-lasting coating on the hair surface.

According to an aspect of some embodiments of the invention, there is provided a method of straightening hair, the method comprising applying cellulose nanocrystals (CNC) to the hair, in combination with conditions suitable for altering a shape of hair, for example, by applying heat and pressure to the hair, preferably at a degree sufficient to cause hair straightening without causing damage to hair.

Herein, a "degree" of an applied heat and/or pressure encompasses a temperature (regarding applied heat), duration (of heat and/or pressure), and/or amount (e.g., of pressure).

Suitable degrees of heat and pressure for effecting hair-straightening, as well as devices (e.g., hot irons) and techniques suitable for applying such heat and pressure, will be known to one of ordinary skill in the art.

The cellulose nanocrystals utilized in any of the embodiments of the invention may optionally be chemically non-modified (which does not exclude naturally-occurring chemical modifications commonly present in cellulose nanocrystals, such as the presence of sulfate groups) or modified. Various suitable forms of modified cellulose nanocrystals are described elsewhere herein.

Hair-straightening treatment according to any of the respective embodiments described herein optionally comprises one or more pre-treatment stages, performed prior to and/or concomitantly with (preferably prior to) application of cellulose nanocrystals. Examples of such pre-treatments include, without limitation, treatments with cationic agents and/or with plasma (e.g., by subjecting the hair to an air plasma jet, using any suitable device).

Thus, in some embodiments, the method comprises:
a) applying at least one cationic agent to the hair and/or subjecting the hair to a plasma treatment;
b) applying cellulose nanocrystals to the hair; and
c) applying heat and pressure to the hair, at a degree sufficient to cause hair straightening without causing damage to hair.

The hair is optionally washed after pre-treatment (e.g., pre-treatment with a cationic agent), and optionally both washed and dried, prior to applying cellulose nanocrystals.

Examples of suitable cationic compounds include, without limitation, amino acids, such as arginine and lysine; cationic polymers, such as chitosan, polylysine (e.g., poly-L-lysine) and polyethyleneimine (PEI); and cationic surfactants, such as behentrimonium salts (e.g., behentrimonium methosulfate (BTMS), cetrimonium (a.k.a. cetyltrimethylammonium, hexadecyltrimethylammonium or HDTMA) salts (e.g., cetrimonium chloride or cetrimonium bromide (CTAB)) and cetylpyridinium salts (e.g., cetylpyridinium chloride (CPC)), and any combination of the foregoing.

Without being bound by any particular theory, it is believed that the surface of CNC is negatively charged (e.g., by sulfate groups introduced during CNC production CNC) and that cationic compounds bind to the negatively charged surface of CNC and/or hair via coulombic attraction, thereby facilitating binding of CNC to the hair surface. It is further believed that cationic surfactants can facilitate binding of CNC to the hair surface by binding to the negatively charged surface of CNC via coulombic attraction and to the hair surface via hydrophobic interactions (as the hair surface is naturally hydrophobic due to the presence of lipids such as 18-methyl eicosanoic acid (18-MEA).

Alternatively or additionally, pre-treatment may optionally comprise plasma treatment—for example, cold plasma treatment—for modifying the hair surface. Plasma treatments are known in the art to be particularly suitable for modifying surface properties without significantly affecting bulk properties.

Plasma treatment may optionally be used to introduce positive charges to the hair surface, in addition to or instead of use of cationic agents.

In some embodiments of any of the respective embodiments described herein, the hair-straightening treatment further comprises applying an agent capable of cleaving disulfide bonds in hair, for example, by reducing disulfide bonds to two free thiol groups or derivatives of thiol groups. Such agents are also collectively referred to herein interchangeably as "a reducing agent".

Examples of suitable agents capable of cleaving disulfide bonds in hair include, without limitation, sulfites and bisulfites (e.g., ammonium sulfite, ammonium bisulfite), metabisulfites (e.g., sodium metabisulfite), and thiols such as cysteine and thioglycolate (e.g., ammonium thioglycolate), and any combination of the foregoing. Sodium metabisulfite (SMBS; $Na_2S_2O_5$) is an exemplary agent for reducing disulfide bonds.

Agents capable of cleaving disulfide bonds in hair are commonly used to facilitate reconfiguration of the keratin in the hair, thereby allowing a straighter hair conformation. All these agents are contemplated herewith.

Without being bound by any particular theory, it is believed that cellulose nanocrystals on the hair enhance the ability of the abovementioned agents to permanently or semi-permanently reconfigure the keratin structure in the hair, by providing mechanical support to the newly formed keratin structure upon straightening and/or by shielding the hair from ambient humidity and/or pollution, which may weaken the effect of the reconfiguration of keratin structure.

In some embodiments of any of the embodiments described herein, the method of straightening hair further comprises applying resilin (as defined herein) to the hair.

In some embodiments, at least a portion of the resilin applied to the hair (according to any of the respective embodiments described herein) is applied subsequently to applying the cellulose nanocrystals (e.g., as part of a composition described herein), for example, at least one day, at least one week and/or at least one month after applying the cellulose nanocrystals. In some such embodiments, the resilin is applied during a time period of up to 2, 3, 4, 5, 6, 7, 8, 9, 10, 11 or 12 months, or even up to 2 years or more, after applying the cellulose nanocrystals.

In some embodiments of any of the embodiments described herein relating to application of resilin subsequently to applying a hair-straightening composition, the application of resilin is for maintenance of straightened hair after straightening the hair by applying the hair-straightening composition (e.g., along with heat and pressure according to any of the respective embodiments described herein).

Herein, "maintenance" (or "maintaining" or variants thereof) of straightened hair refers to delaying (e.g., decreasing a rate of) and/or at least partially reversing (e.g., temporarily reversing) a process whereby the effect of hair straightening treatment on the shape of hair is gradually lost.

Thus, for each time the hair is straightened (to obtain straightened hair), application of resilin (according to any of the respective embodiments described herein) may optionally be effected thereafter once, twice (e.g., on two different days), or 3, 4, 5, 6, 7, 8, 9, 10 or more times (e.g., on different days), so as to maintain the previously straightened hair in a straightened state.

For example, application of resilin can be effected once a day, every day after the hair straightening treatment, for, for example, 1, 2, 3, 4, 5, 6, 7, days, or more, or for 2 weeks, 3 weeks, 4 weeks, or more, as desired. Alternatively, application of resilin can be effected every other day after the hair straightening treatment, for a time period as desired (e.g., as indicated hereinabove). Further alternatively, application of resilin can be effected once, twice, or trice, as week, after the hair straightening treatment, for a time period as desired (e.g., as indicated hereinabove).

According to an aspect of some embodiments of the invention, there is provided a method for maintenance of straightened hair following a hair-straightening treatment, the method comprising applying resilin to the hair, according to any of the respective embodiments described herein. The hair-straightening treatment is optionally according to any of the embodiments described herein relating to a hair-straightening treatment (e.g., utilizing application of cellulose nanocrystals), or alternatively, may be any other hair-straightening treatment known in the art.

In some of any of the embodiments relating to maintenance of straightened hair, the resilin is applied to the hair (according to any of the respective embodiments described herein) at least one day, at least one week and/or at least one month after the hair-straightening treatment. In some such embodiments, the resilin is applied during a time period of up to 2, 3, 4, 5, 6, 7, 8, 9, 10, 11 or 12 months, or even up to 2 years or more, after the hair-straightening treatment.

It is expected that during the life of a patent maturing from this application many relevant hair-straightening treatments will be developed and the scope of the term "hair-straightening treatment" is intended to include all such new technologies a priori, except where such a treatment is clearly excluded from a described embodiment.

According to an aspect of some embodiments of the present invention there is provided a method of straightening hair, which comprises subjecting the hair to a first hair-straightening treatment (e.g., a hair-straightening treatment according to any of the embodiments described herein relating to a hair-straightening treatment utilizing application of cellulose nanocrystals, or alternatively, by any other hair-straightening treatment known in the art, as described herein);

applying resilin to the hair following the first hair-straightening treatment, according to any of the respective embodiments described herein;

subjecting the hair to a second hair-straightening treatment as described herein in any of the respective embodiments of the first treatment; and applying resilin to the hair following the first hair-straightening treatment, according to any of the respective embodiments described herein, and optionally, subjecting the hair to third, fourth, fifth, etc. hair-straightening treatments, as desired, while applying resilin following each treatment, such that a time period between consecutive treatments is longer by at least 20%, or at least 30%, or at least 40%, or at least 50%, or more, than the time period between the same consecutive treatments without application of resilin following each treatment required for maintaining straightened hair as desired by a subject.

In some embodiments, the time period between each of the first and second hair-straightening treatments, and/or between each of the second and third treatments, and/or between the third and fourth treatments, and so on, that is, between consecutive treatments, is at least 4 weeks, or at least 8 weeks, or at least 3 months, or at least 6 month, or at least 8 months, or at least 10 months, or at least one year, or even more (e.g., 2 years).

This method utilizes the maintenance effect provided by the application of resilin by enabling a reduced frequency of hair-straightening treatments that are required or desired for maintaining straightened hair.

In some of any of the embodiments described herein, in any of the relevant methods described herein a modified and/or non-modified CNC (according to any of the respective embodiments described herein) is applied in a composition comprising same, as described in further detail hereinunder. In some embodiments, a concentration of the modified and/or non-modified CNC in the composition ranges from about 0.1% to about 5%, by weight, including any intermediate values and subranges therebetween.

In some of any of the embodiments described herein, in any of the relevant methods described herein, a resilin (according to any of the respective embodiments described herein) is applied in a composition comprising same, as described in further detail hereinunder. In some embodiments, a concentration of the resilin in the composition ranges from about 0.1 mg/ml to about 200 mg/ml, including any intermediate values and subranges therebetween.

In some of any of the embodiments described herein, in any of the relevant methods described herein, a reducing agent (according to any of the respective embodiments described herein) is applied in a composition comprising same, as described in further details hereinunder. In some embodiments, a concentration of the reducing agent in the composition ranges from about 1 nM to 2M, including any intermediate values and subranges therebetween.

In some of any of the embodiments described herein, in any of the relevant methods described herein a cationic agent (according to any of the respective embodiments described herein) is applied in a composition comprising same, as described in further details hereinunder. In some embodiments, a concentration of the cationic agent in the composition ranges from about 0.1% to about 40%, by weight, including any intermediate values and subranges therebetween.

In some of any of the embodiments described herein, an amount of any of the agents or compositions comprising same that applied to the hair depends on the type, length, curliness, width, and other factors of the hair of an individual subject. Those skilled in the art would readily determine which amounts would provide desired results for an individual subject.

Modified Cellulose Nanocrystals:

In some embodiments of any of the embodiments described herein relating to CNC, the CNC optionally comprises chemically modified CNC. Modifications of CNC may optionally be selected so as to provide a desired stiffness/flexibility of a CNC film applied onto hair, and/or a desired hydrophobicity/hydrophilicity.

A wide variety of techniques for modifying cellulose are known in the art (e.g., by covalently modifying hydroxyl groups at the cellulose surface), and may optionally be used in the context of some embodiments of the invention. Examples of such modifications include, without limitation, esterification (e.g., according to procedures such described by Zoppe et al. [*Biomacromolecules* 2010, 11:2683-2691] or Habibi et al. [*J Mater Chem* 2008, 18:5002-5010]), etherification with alkylating agents (e.g., according to procedures such described by Hermanson GT [Bioconjugate Techniques, (Academic, San Diego, 1996)]), oxidation (e.g., according to procedures such as described by Azzam et al. [*Biomacromolecules* 2010, 11:3652-3659]), silylation (e.g., according to procedures such as described by Taipina et al. [*Cellulose* 2013, 20:217-226]), reaction with isocyanates (e.g., according to procedures such described by Shang et al. [*Cellulose* 2013, 20:179-190] or Yu et al. [*ACS Sustainable Chem Eng* 2014, 2:875-886]), and/or polymer grafting (e.g., according to procedures such described by Shang et al. [*Cellulose* 2013, 20:179-190], Zoppe et al. [*Biomacromolecules* 2010, 11:2683-2691], Habibi et al. [*J Mater Chem* 2008, 18:5002-5010] or Azzam et al. [*Biomacromolecules* 2010, 11:3652-3659]).

In some of any of the respective embodiments described herein, the modified CNC is modified by the addition of an acryl or methacryl functional group (referred to herein as "(meth)acryl" or a variant thereof).

The (meth)acryl group may optionally be attached directly to the cellulose by an ester linkage (—O—C(=O)—), for example, by contacting CNC with a reagent such as (meth)acrylic anhydride, (meth)acryl chloride, and the like.

Alternatively or additionally, the may optionally be attached to the cellulose via a linking moiety, for example, by contacting CNC with a reagent such as glycidyl (meth)acrylate or isocyanatoethyl (meth)acrylate, under suitable conditions (e.g., in the presence of a base such as triethylamine or sodium hydroxide), optionally aqueous conditions.

In some of any of the respective embodiments described herein, the modified CNC is modified by a polyester network on the CNC surface, for example, a castor oil-based polyol (COPO). The polyester is optionally attached to the CNC via a diisocyanate linker, for example, a diisocyanate (e.g., toluene diisocyanate) linker such as described by Shang et al. [*Cellulose* 2013, 20:179-190].

In some of any of the respective embodiments described herein, the modified CNC is modified by the addition of a hydrophobic functional group, optionally attached to the cellulose by an ester linkage (—O—C(=O)—). Hydrophobic ester groups (e.g., $C_{8-50}$-acyl) may be formed, for example, by contacting CNC with a reagent such as a fatty acyl chloride, an alkyl ketene dimer (which forms beta-ketocarboxylic ester groups), or an alkenyl succinic anhydride, or any other suitable agent used in the art to modify cellulose (e.g., in paper sizing processes).

In some of any of the respective embodiments described herein, the modified CNC is modified by the addition of a thiol functional group. Many agents (e.g., "thiolating agents") and techniques suitable for introducing thiol groups are known in the art.

In some embodiments, modified cellulose nanocrystals comprising a thiol group are attached to keratin in the hair via disulfide bonds formed between cysteine in the keratin and the cellulose nanocrystal thiol. Alternatively or additionally, modified cellulose nanocrystals comprising a thiol group are attached to each other, so as to cross-link the cellulose nanocrystals.

Such disulfide bonds are optionally formed by contacting the CNC with a suitable oxidizing agent. Suitable oxidizing agents for forming disulfide bonds in hair are known in the art, and are often used at the end of hair-straightening treatments (e.g., to stabilize the newly straightened hair conformation).

Thiol groups may optionally be utilized for further modification of CNC, for example, by reacting with haloacetyl, alkyl halide, maleimide, and/or aziridine groups.

In some of any of the respective embodiments described herein, modification comprises oxidizing cellulose, so as to obtain aldehyde groups and/or carboxylate groups (in addition to or instead of the naturally occurring hydroxyl groups of cellulose). For example, aldehyde groups may be obtained by periodate-oxidation of glucose residues in cellulose (e.g., as exemplified herein).

The aldehyde groups and/or carboxylate groups are optionally used to react with agents which comprise a desired functional group as well as a functional group (e.g., amine) for attaching to the aldehyde or carboxylate, which may not be as readily attached to CNC. For example, amine groups can be reacted with carboxylates to form an amide linkage, using common techniques (e.g., using a carbodiimide such as 1-ethyl-3-(3-dimethylaminopropyl)carbodiimide (EDC), and with aldehydes to form an imine. Aldehyde groups on cellulose can also be sulfonated by upon reaction with bisulfite (e.g., as described by Liimatainen et al. [*Cellulose* 2013; 20:741-749]).

Carbodiimide (e.g., EDC) coupling is optionally effected under acidic (e.g., pH 4.5-5.5) conditions, such as in a MES (2-(N-morpholino)ethanesulfonic acid), although phosphate buffers at pH≤7.2 are also compatible with the reaction chemistry. N-hydroxysuccinimide (NHS) or its water-soluble analog (sulfo-NHS) is optionally included in carbodiimide coupling protocols to improve efficiency and/or to create a more stable, amine-reactive intermediate.

In some embodiments, a polypeptide (e.g., silk or resilin protein), according to any of the respective embodiments described herein, is attached to CNC via one or more amine groups in the polypeptide, for example, via carbodiimide coupling (e.g., any of the respective embodiments described herein).

In some embodiments, oxidized CNC (e.g., $NaClO_2$-oxidized CNC) comprising carboxylate groups is reacted with a compound comprising an amine group linked to a thiol group (e.g., via a hydrocarbon linker such as $C_2$-$C_{10}$ alkylene, as in 6-amino-1-hexanethiol), using carbodiimide coupling, so as to obtain thiol groups attached to the CNC via amide linkages (—C(=O)—NH—).

In some embodiments, oxidized CNC (e.g., $NaClO_2$-oxidized CNC) comprising carboxylate groups is reacted with a compound comprising an amine group linked to a thiol group (e.g., via a hydrocarbon linker such as $C_2$-$C_{10}$ alkylene, as in 6-amino-1-hexanethiol), using carbodiimide coupling, so as to obtain thiol groups attached to the CNC via amide linkages (—C(=O)—NH—).

CNC may also be modified (e.g., by attachment to a polypeptide) via click chemistry, e.g., as described by Karaaslan et al. [*Cellulose* 2013, 20:2655-2665].

Alternatively or additionally to any of the covalent modifications described herein, the cellulose nanocrystals may optionally be modified non-covalently, for example, by attachment (e.g., adsorption) of compounds to a surface thereof by noncovalent bonds (e.g., hydrophobic interactions, hydrogen bonds, and/or electrostatic interactions), and/or by coating a surface of the crystals with a polymer.

In some embodiments of any of the respective embodiments described herein, the cellulose nanocrystals are attached non-covalently to a polypeptide, for example, a polypeptide comprising a cellulose binding domain (e.g., according to any of the respective embodiments described herein). The cellulose binding domain (CBD) is optionally incorporated into a protein, for example, a silk or resilin protein. Resilin with a CBD is an exemplary protein suitable for noncovalent modification of cellulose nanocrystals.

CBD (cellulose binding domain) belongs to a large superfamily of carbohydrate-binding molecules (CBMs), and represents a contiguous amino acid sequence within carbohydrate-active enzymes. The domain features a discrete fold, carbohydrate (cellulose)-binding activity, and has been found in both hydrolytic and non-hydrolytic proteins. The utilization of CBDs is described, for example, by Shoseyov et al. [*Microbiol Mol Biol Rev* 2006, 70:283-295], which is incorporated herein by reference.

Examples of cellulose binding domain (CBD) amino acid sequences are provided in SEQ ID NOs: 17, 18 and 21, and in Yaniv et al. [*Acta Crystallogr Sect F Struct Biol Cryst Commun* 2013, 69:733-737] (e.g., PDB: 4J05-A).

Without being bound by any particular theory, it is believed that proteins such as silk and resilin can provide elasticity and resilience, for example, to a layer of CNC on the hair surface.

Silk protein according to any of the respective embodiments described herein optionally comprises spider silk protein, and optionally spider dragline silk protein. The spider silk protein is optionally a recombinant protein fused to CBD.

A silk polypeptide (with or without a CBD) may optionally comprise any silk polypeptide described in International Patent Application Publication WO 2009/069123, the contents of which are incorporated herein by reference.

Fusion of CBD to silk protein can dramatically improve protein properties, such as its molecular order and melting point. The highly ordered crystalline cellulose structure optionally serves as a template to enable the assembly of silk proteins into hair fibers. This can optionally be facilitated by the fusion of silk proteins to CBD, thereby facilitating film assembly of silk-CBD and/or CNC over hair fibers.

Cross-Linking Cellulose Nanocrystals:

In some embodiments of any of the embodiments described herein relating to a method of straightening hair by applying cellulose nanocrystals (CNC) to the hair, the method further comprises cross-linking the cellulose nanocrystals on the hair.

Without being bound by any particular theory, it is believed that cross-linking cellulose nanocrystals on the hair results in a more rigid and/or durable layer coating the hair surface, thereby enhancing the effect of the cellulose nanocrystals (e.g., as a surface barrier and/or as a mechanical support of hair-straightening).

Cross-linking may optionally be effected by contacting the cellulose nanocrystals with a suitable cross-linking agent, for example, during and/or after application of the cellulose nanocrystals onto the hair. Alternatively or additionally, cross-linking may be effected by irradiating the cellulose (e.g., by UV and/or visible light), for example, chemically modified cellulose nanocrystals selected to be cross-linkable upon irradiation.

Cross-linking may optionally be effected prior to, concomitantly with and/or subsequently to applying heat and pressure to straighten the hair.

In some embodiments of any of the respective embodiments, cross-linking is effected by UV irradiation at a sufficient dosage (e.g., intensity and/or duration) to effect cross-linking of the CNC. In some such embodiments, the CNC is a modified CNC comprising a UV-cross-linkable functional group such as a (meth)acrylate functional group (e.g., according to any of the respective embodiments described herein).

Irradiation is optionally effected in the presence of a photoinitiator (e.g., a water-soluble photoinitiator, such as 2-hydroxy-4'-(2-hydroxyethoxy)-2-methylpropiophenone marketed under the trademark IRGACURE® 2959). The photoinitiator may optionally be applied to the hair along with the CNC, for example, wherein the photoinitiator is co-formulated with the CNC in a composition described herein.

Irradiation with UV and/or visible light may optionally be effected by a practitioner of a hair-straightening treatment (e.g., a hairdresser or employee thereof). Alternatively or additionally, the irradiation is effected by exposure to natural sunlight.

Examples of suitable cross-linking agents which may be used to cross-link cellulose nanocrystals include, without limitation, alpha-hydroxyacids (e.g., lactic acid, glycolic acid, malic acid, citric acid, tartaric acid, and derivatives thereof), which may optionally promote esterification/transesterification cross-linking reactions at the CNC interface; compounds with two or more carboxylic acid groups (e.g., adipic acid, azelaic acid, succinic acid, malic acid, tartaric acid, citric acid, BTCA (1,2,3,4-butanetetracarboxylic acid), and derivatives thereof), which may be esterified (e.g., according to any of the respective embodiments described herein) to hydroxyl groups of different cellulose nanocrystals; and proteins (e.g., casein, albumin, gelatin, resilin).

Oxidizing agents may optionally be used to cross-link modified CNC with thiol groups (e.g., as described herein).

Polypeptides such as proteins (e.g., casein, albumin, gelatin, keratin) may optionally cross-link CNC upon application of heat via condensation reactions such as esterification (e.g., between polypeptide carboxylate groups and hydroxyl groups on CNC and/or another polypeptide). Alternatively or additionally, the polypeptide (e.g., resilin) cross-links CNC (e.g., CNC oxidized to comprise carboxylate groups) via carbodiimide (e.g., EDC) coupling. Alternatively, or additionally the polypeptide (e.g., gelatin) cross-links the CNC in the presence of a transglutaminase which is naturally present in or applied to the hair.

Cross-linking nanocrystals with polypeptides may optionally be effected by attaching a polypeptide molecule to two or more nanocrystals (e.g., by condensation, and/or carbodiimide coupling), and/or by attaching (e.g., by condensation, carbodiimide coupling, and/or transglutaminase) a polypeptide molecule attached to a nanocrystal (e.g., by condensation, and/or carbodiimide coupling) to another polypeptide molecule attached to another nanocrystal.

A polypeptide used to cross-link CNC according to any of the respective embodiments described herein may optionally bind to the CNC covalently (e.g., according to any of the embodiments described herein relating to covalent modification of CNC).

Alternatively or additionally, a polypeptide used to cross-link CNC according to any of the respective embodiments described herein may optionally bind to the CNC non-covalently (e.g., according to any of the embodiments described herein relating to noncovalent modification of CNC), for example, wherein the polypeptide comprises a cellulose binding domain (e.g., a modified resilin or silk, or an isolated cellulose binding domain polypeptide). In such embodiments, the cross-linking may be effected by covalently cross-linking a plurality of polypeptides non-covalently attached to CNC, for example, by condensation, carbodiimide coupling, and/or transglutaminase (according to any of the respective embodiments described herein).

In some of any of the embodiments described herein, in any of the relevant methods described herein, the modified and/or non-modified CNC is employed in combination with a cross-linking agent as described herein. In some embodiments, the CNC and the cross-linking agent are applied concomitantly, or sequentially, in any order. A concentration ratio between the CNC and the cross-linking agent can be determined in accordance with the chemical composition of the cross-linking agent and the desired degree of cross-linking. Exemplary such ratios may range from 100:1 to 1:1.

If a cross-linking agent is employed, it can form a part of a composition comprising same, as described in further detail hereinunder.

Resilin:

Herein, the term "resilin" encompasses a polypeptide comprising a sequence of a naturally-occurring resilin protein, a fragment of a naturally-occurring resilin protein, or a homologous polypeptide thereof (i.e., a polypeptide homologous to a resilin protein or fragment thereof, as defined herein).

Herein, a "homologous polypeptide" of a given polypeptide encompasses polypeptides which are at least 50%, at least 55%, at least 60%, at least 65%, at least 70%, at least 75%, at least 80%, at least 85%, at least 87%, at least 89%, at least 91%, at least 93%, at least 95% or more, e.g., 100%, homologous to the given polypeptide, such as a resilin protein described herein (e.g., a sequence listed in Table 1 or a fragment thereof), as determined using BlastP software of the National Center of Biotechnology Information (NCBI) using default parameters. The homologous polypeptide may also refer to a deletion, insertion, or substitution variant, including an amino acid substitution, thereof and biologically active polypeptide fragments thereof.

In some of any of the embodiments described herein, a homologous polypeptide is at least 80% homologous, as defined hereinabove. In some embodiments, a homologous polypeptide is at least 85% homologous, as defined hereinabove. In some embodiments, a homologous polypeptide is at least 90% homologous, as defined hereinabove. In some embodiments, a homologous polypeptide is at least 95% homologous, as defined hereinabove. In some embodiments, a homologous polypeptide is at least 98% homologous, as defined hereinabove. In some embodiments, a homologous polypeptide is at least 99% homologous, as defined hereinabove.

In some of any of the embodiments described herein, a fragment of a resilin protein (or homologous polypeptide thereof) is at least 50 amino acid residues in length. In some embodiments, a fragment of a resilin protein is at least 60 amino acid residues in length. In some embodiments, a fragment of a resilin protein is at least 70 amino acid residues in length. In some embodiments, a fragment of a resilin protein is at least 80 amino acid residues in length. In some embodiments, a fragment of a resilin protein is at least 100 amino acid residues in length. In some embodiments, a fragment of a resilin protein is at least 125 amino acid residues in length. In some embodiments, a fragment of a resilin protein is at least 150 amino acid residues in length. In some embodiments, a fragment of a resilin protein is at least 200 amino acid residues in length.

In some of any of the embodiments described herein, the resilin (according to any of the respective embodiments described herein) consists essentially of a naturally-occurring resilin protein, a fragment thereof, or a homologous polypeptide thereof.

In some of any of the embodiments described herein, the resilin according to any of the respective embodiments described herein) comprises one or more peptide sequence(s) in addition to a naturally-occurring resilin sequence, a fragment thereof, or a homologous polypeptide thereof.

GenBank Accession Nos. of non-limiting examples of resilin are listed in Table 1 below.

TABLE 1

| Exemplary resilin NCBI sequence number | Organism |
| --- | --- |
| NP 995860 | Drosophila melanogaster |
| NP 611157 | Drosophila melanogaster |
| Q9V7U0 | Drosophila melanogaster |
| AAS64829 | Drosophila melanogaster |
| AAF57953 | Drosophila melanogaster |
| XP 001817028 | Tribolium castaneum |
| XP001947408 | Acyrthosiphon pisum |

According to some of any of the embodiments described herein, the resilin (according to any of the respective embodiments described herein) comprises the full length resilin amino acid sequence (i.e. comprises amino acids from each of exon 1, exon 2 and exon 3), for example, as set forth in SEQ ID NO: 19.

According to other embodiments, the resilin (according to any of the respective embodiments described herein) comprises an exon 1 resilin amino acid sequence (SEQ ID NOs: 1, 2 or 16), or a homologous polypeptide sequence, which may be 70% homologous, 75% homologous, 80% homologous, 85% homologous, 90% homologous, 91% homologous, 92% homologous, 93% homologous, 94% homologous, 95% homologous, 96% homologous, 97% homologous, 98% homologous, 99% homologous or 100% homologous to the sequence as set forth in SEQ ID NOs: 1, 2 or 16 as determined using BlastP software of the National Center of Biotechnology Information (NCBI) using default parameters). The homologous polypeptide sequence may also refer to a deletion, insertion, or substitution variant, including an amino acid substitution, thereof and biologically active polypeptide fragments thereof.

In some of any of the embodiments described herein, the resilin (according to any of the respective embodiments described herein) is a modified resilin comprising a cellulose binding domain (CBD).

In some of any of the embodiments described herein, the resilin amino acid sequence (according to any of the respective embodiments described herein) comprises an exon 1 resilin amino acid sequence and a polysaccharide binding domain (e.g. a cellulose binding domain (CBD) and/or a chitin binding domain (ChBD), such as that encoded in exon 2).

Herein, the phrase "polysaccharide-binding domain" refers to a polypeptide or a portion thereof which is capable of selectively binding to a polysaccharide. Various polysaccharide-binding domains are known in the art.

An example of a ChBD sequence found in exon 2 of resilin is provided in SEQ ID NO: 3 or 6.

In some of any of the embodiments described herein, the resilin (according to any of the respective embodiments described herein) is a modified resilin comprising a cellulose binding domain (CBD).

Examples of cellulose binding domain (CBD) amino acid sequences are provided in SEQ ID NOs: 17 and 18.

Another example of a cellulose binding domain (CBD) amino acid sequence is a sequence homologous to the sequence as set forth in SEQ ID NO:21 (as determined using BlastP software of the National Center of Biotechnology Information (NCBI) using default parameters), which may be 70% homologous, 75% homologous, 80% homologous, 85% homologous, 90% homologous, 91% homologous, 92% homologous, 93% homologous, 94% homologous, 95% homologous, 96% homologous, 97% homologous, 98% homologous, 99% homologous or 100% homologous to the sequence as set forth in SEQ ID NO:21. The homologous polypeptide sequence may also refer to a deletion, insertion, or substitution variant, including an amino acid substitution, thereof and biologically active polypeptide fragments thereof.

Without being bound by any particular theory, it is believed that a cellulose binding domain in a resilin is useful for facilitating adherence of applied resilin to applied cellulose nanocrystals, e.g., in the context of any of the respective embodiments described herein.

Additional polysaccharide binding domains are provided in International Patent Application Publication WO 2009/069123, incorporated herein by reference.

The polysaccharide binding domain may be linked to the C terminal domain of exon 1 or the N terminal domain of exon 1 (either directly or via a linker).

According to still other embodiments, the resilin amino acid sequence (according to any of the respective embodiments described herein) comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating units as set forth in SEQ ID NO: 20, and optionally as set forth in SEQ ID NO: 4 (Gly Gly Arg Pro Ser Asp Ser Tyr Gly Ala Pro Gly Gly Gly Asn).

According to still other embodiments the resilin amino acid sequence (according to any of the respective embodiments described herein) comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating units as set forth in SEQ ID NO: 5 (GRPSDSYGA).

According to still other embodiments the resilin amino acid sequence (according to any of the respective embodiments described herein) is devoid of an exon 3 amino acid sequence.

According to yet other embodiments, the resilin amino acid sequence (according to any of the respective embodiments described herein) comprises an exon 3 amino acid sequence.

Examples of polynucleotides which can be used to express resilin are set forth in SEQ ID NO: 7, 8, 10, 12 and 14.

Examples of 6H-tagged resilin polypeptide sequences are set forth in SEQ ID NO: 9, 11, 13 and 15. SEQ ID NO: 13 is an exemplary polypeptide sequence. Such sequences may be readily isolated utilizing the 6H-tag, and may be incorporated as is in the composition-of-matter or incorporated after removing the 6H-tag, for example, as described in International Patent Applicant Publication WO 2015/068160, which is incorporated herein by reference (particularly with respect to resilin sequences described therein).

Other exemplary polypeptide and polynucleotide sequences, that may be used in the context of any of the embodiments described herein relating to resilin, are provided in International Application Publication WO 2009/069123 and in International Patent Application Publication WO 2013/030840, which are incorporated herein by reference.

In some of any of the embodiments described herein, a mol ratio of a resilin as described herein and CNC ranges from 1:1 to 1:50, or from 1:1 to 1:20, or from 1:5 to 1:20, including any intermediate value and subranges therebetween.

Polypeptides:

The term "polypeptide" as used herein encompasses native peptide macromolecules (e.g., a resilin or silk polypeptide), including degradation products, synthetically prepared peptides and recombinant peptides (e.g., recombinantly expressed in a microorganism), as well as peptidomimetic macromolecules (typically, synthetically synthesized peptides), as well as peptoid and semipeptoid macromolecules which are peptide analogs, which may have, for example, modifications rendering the polypeptides more stable. Such modifications include, but are not limited to N-terminus modification, C-terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein below.

Peptide bonds (—CO—NH—) within the polypeptide may be substituted, for example, by N-methylated amide bonds (—N(CH3)-CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g. methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), retro-amide bonds (—NH—CO—), peptide derivatives (—N(R)—CH$_2$—CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some of any of the embodiments described herein may also include one or more modified amino acids or one or more non-amino acid monomers e.g. fatty acids, complex carbohydrates, etc.

The term "amino acid" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids e.g. synthetic (Table 3) which can be used with some embodiments of the invention.

TABLE 2

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| Ornithine | Orn | hydroxyproline | Hyp |
| α-aminobutyric acid | Abu | aminonorbornyl-carboxylate | Norb |
| D-alanine | Dala | | |
| D-arginine | Darg | aminocyclopropane-carboxylate | Cpro |
| D-asparagine | Dasn | | |
| D-aspartic acid | Dasp | N-(3-guanidinopropyl)glycine | Narg |
| D-cysteine | Dcys | | |
| D-glutamine | Dgln | N-(carbamylmethyl)glycine | Nasn |
| D-glutamic acid | Dglu | N-(carboxymethyl)glycine | Nasp |
| D-histidine | Dhis | N-(thiomethyl)glycine | Ncys |
| D-isoleucine | Dile | N-(2-carbamylethyl)glycine | Ngln |
| D-leucine | Dleu | N-(2-carboxyethyl)glycine | Nglu |
| D-lysine | Dlys | N-(imidazolylethyl)glycine | Nhis |
| D-methionine | Dmet | N-(1-methylpropyl)glycine | Nile |
| D-ornithine | Dorn | N-(2-methylpropyl)glycine | Nleu |
| D-phenylalanine | Dphe | N-(4-aminobutyl)glycine | Nlys |
| D-proline | Dpro | N-(2-methylthio-ethyl)glycine | Nmet |
| D-serine | Dser | | |
| D-threonine | Dthr | N-(3-aminopropyl)glycine | Norn |
| D-tryptophan | Dtrp | N-benzylglycine | Nphe |
| D-tyrosine | Dtyr | N-(hydroxymethyl)glycine | Nser |
| D-valine | Dval | N-(1-hydroxyethyl)glycine | Nthr |
| D-N-methylalanine | Dnmala | N-(3-indolylethyl) glycine | Nhtrp |
| D-N-methylarginine | Dnmarg | N-(p-hydroxyphenyl)glycine | Ntyr |
| D-N-methylasparagine | Dnmasn | N-(1-methylethyl)glycine | Nval |
| D-N-methylasparatate | Dnmasp | N-methylglycine | Nmgly |
| D-N-methylcysteine | Dnmcys | L-N-methylalanine | Nmala |
| D-N-methylglutamine | Dnmgln | L-N-methylarginine | Nmarg |
| D-N-methylglutamate | Dnmglu | L-N-methylasparagine | Nmasn |
| D-N-methylhistidine | Dnmhis | L-N-methylaspartic acid | Nmasp |
| D-N-methylisoleucine | Dnmile | L-N-methylcysteine | Nmcys |
| D-N-methylleucine | Dnmleu | L-N-methylglutamine | Nmgln |
| D-N-methyllysine | Dnmlys | L-N-methylglutamic acid | Nmglu |
| D-N-methylmethionine | Dnmmet | L-N-methylhistidine | Nmhis |
| D-N-methylornithine | Dnmorn | L-N-methylisolleucine | Nmile |
| D-N-methylphenylalanine | Dnmphe | L-N-methylleucine | Nmleu |
| | | L-N-methyllysine | Nmlys |
| D-N-methylproline | Dnmpro | L-N-methylmethionine | Nmmet |
| D-N-methylserine | Dnmser | L-N-methylornithine | Nmorn |
| D-N-methylthreonine | Dnmthr | L-N-methylphenylalanine | Nmphe |
| D-N-methyltryptophan | Dnmtrp | L-N-methylproline | Nmpro |

TABLE 3-continued

| Non-conventional amino acid | Code | Non-conventional amino acid | Code |
|---|---|---|---|
| D-N-methyltyrosine | Dnmtyr | L-N-methylserine | Nmser |
| D-N-methylvaline | Dnmval | L-N-methylthreonine | Nmthr |
| L-norleucine | Nle | L-N-methyltryptophan | Nmtrp |
| L-norvaline | Nva | L-N-methyltyrosine | Nmtyr |
| L-ethylglycine | Etg | L-N-methylvaline | Nmval |
| L-t-butylglycine | Tbug | L-N-methylnorleucine | Nmnle |
| L-homophenylalanine | Hphe | L-N-methylnorvaline | Nmnva |
| α-naphthylalanine | Anap | L-N-methyl-ethylglycine | Nmetg |
| Penicillamine | Pen | L-N-methyl-t-butylglycine | Nmtbug |
| γ-aminobutyric acid | Gabu | L-N-methyl-homophenylalanine | Nmhphe |
| cyclohexylalanine | Chexa | | |
| cyclopentylalanine | Cpen | N-methyl-α-naphthylalanine | Nmanap |
| α-amino-α-methylbutyrate | Aabu | N-methylpenicillamine | Nmpen |
| | | N-methyl-γ-aminobutyrate | Nmgabu |
| α-aminoisobutyric acid | Aib | N-methyl-cyclohexylalanine | Nmchexa |
| D-α-methylarginine | Dmarg | N-methyl-cyclopentylalanine | Nmcpen |
| D-α-methylasparagine | Dmasn | N-methyl-α-amino-α-methylbutyrate | Nmaabu |
| D-α-methylaspartate | Dmasp | | |
| D-α-methylcysteine | Dmcys | N-methyl-α-aminoisobutyrate | Nmaib |
| D-α-methylglutamine | Dmgln | | |
| D-α-methyl glutamic acid | Dmglu | L-α-methylarginine | Marg |
| | | L-α-methylasparagine | Masn |
| D-α-methylhistidine | Dmhis | L-α-methylaspartate | Masp |
| D-α-methylisoleucine | Dmile | L-α-methylcysteine | Mcys |
| D-α-methylleucine | Dmleu | L-α-methylglutamine | Mgln |
| D-α-methyllysine | Dmlys | L-α-methylglutamate | Mglu |
| D-α-methylmethionine | Dmmet | L-α-methylhistidine | Mhis |
| D-α-methylornithine | Dmorn | L-α-methylisoleucine | Mile |
| D-α-methylphenylalanine | Dmphe | L-α-methylleucine | Mleu |
| | | L-α-methyllysine | Mlys |
| D-α-methylproline | Dmpro | L-α-methylmethionine | Mmet |
| D-α-methylserine | Dmser | L-α-methylornithine | Morn |
| D-α-methylthreonine | Dmthr | L-α-methylphenylalanine | Mphe |
| D-α-methyltryptophan | Dmtrp | L-α-methylproline | Mpro |
| D-α-methyltyrosine | Dmtyr | L-α-methylserine | Mser |
| D-α-methylvaline | Dmval | L-α-methylthreonine | Mthr |
| N-cyclobutylglycine | Ncbut | L-α-methyltryptophan | Mtrp |
| N-cycloheptylglycine | Nchep | L-α-methyltyrosine | Mtyr |
| N-cyclohexylglycine | Nchex | L-α-methylvaline | Mval |
| N-cyclodecylglycine | Ncdec | L-α-methylnorvaline | Mnva |
| N-cyclododecylglycine | Ncdod | L-α-methylethylglycine | Metg |
| N-cyclooctylglycine | Ncoct | L-α-methyl-t-butylglycine | Mtbug |
| N-cyclopropylglycine | Ncpro | L-α-methyl-homophenylalanine | Mhphe |
| N-cycloundecylglycine | Ncund | | |
| N-(2-aminoethyl)glycine | Naeg | α-methyl-α-naphthylalanine | Manap |
| | | α-methylpenicillamine | Mpen |
| N-(2,2-diphenylethyl)glycine | Nbhm | α-methyl-γ-aminobutyrate | Mgabu |
| | | α-methyl-cyclohexylalanine | Mchexa |
| N-(3,3-diphenylpropyl)glycine | Nbhe | α-methyl-cyclopentylalanine | Mcpen |
| | | N-(N-(2,2-diphenylethyl) carbamylmethyl-glycine | Nnbhm |
| 1-carboxy-1-(2,2-diphenyl ethylamino)cyclo-propane | Nmbc | N-(N-(3,3-diphenylpropyl) carbamylmethyl-glycine | Nnbhe |
| | | 1,2,3,4-tetrahydroisoquinoline-3-carboxylic acid | Tic |
| Phosphoserine | pSer | | |
| phosphotyrosine | pTyr | | |
| 2-aminoadipic acid | | phosphothreonine | pThr |
| | | O-methyl-tyrosine | |
| | | hydroxylysine | |

The polypeptides of some embodiments of the invention are preferably utilized in a linear form, although it will be appreciated that in cases where cyclization does not severely interfere with polypeptide characteristics, cyclic forms of the polypeptide can also be utilized.

The polypeptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after de-protection, a pentapeptide and so forth. Further description of polypeptide synthesis is disclosed in U.S. Pat. No. 6,472,505.

A preferred method of preparing a polypeptide some embodiments of the invention involves solid phase polypeptide synthesis.

Large scale polypeptide synthesis is described by Andersson [*Biopolymers* 2000; 55(3):227-50].

Polynucleotides of the present invention may be prepared using PCR techniques as described in the Examples section below, or can be chemically synthesized or by any other method or procedure known in the art for ligation of two different DNA sequences. See, for example, "Current Protocols in Molecular Biology", eds. Ausubel et al., John Wiley & Sons, 1992.

Polypeptides of the present invention can be purified using a variety of standard protein purification techniques, such as, but not limited to, heat treatments, salting out for example with ammonium sulfate, polyethyleneimines (PEI) precipitation, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety (see Examples section, herein below).

Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in a "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Color and Optical Effects:

The treatment of hair using CNC describes herein may optionally be in combination with coloring agents and other agents for altering the appearance of hair.

Typically, many pigments and dyes are not particularly suitable for coloring hair, as they do not adhere to the hair for long.

Without being bound by any particular theory, it is believed that a layer of applied CNC (especially cross-linked CNC) on the hair surface, according to embodiments described herein, can embed pigments (e.g., organic pigments) and other agents with desired optical properties, thereby providing the hair (in a controllable manner) with a desired absorption (e.g., color and/or UV protection) and/or shine features. Such agents may be colorless or colored mineral and/or organic pigments.

Examples of suitable mineral pigments include, without limitation, titanium dioxide (used as a white pigment), cerium oxide, zinc oxide, iron oxide (black, yellow and red), chromium oxide, manganese violet, ultramarine blue, chromium hydrate and ferric blue. In addition, metal powders such as aluminum or copper and their mixtures can optionally be utilized.

Examples of suitable organic pigments (which may be lipophilic and/or water-soluble) include, without limitation, carbon black, D & C types and such pigments based on cochineal carmine or barium, strontium, calcium, aluminum and their mixtures; nacre or nacreous pigments; lipophilic dyes such as soybean oil, Sudan brown, DC Yellow 11, DC Orange 5, quinoline yellow, and Sudan Red III; water-soluble dyes such as plant extracts (e.g., *Aleurites moluccana* Willd, *Alkanna tinctoria* Tausch, *Areca catechu* L., *Arrabidaea chica* E.), optionally in a lyophilized, paste or solution form.

Nanoparticles may optionally be used (e.g., embedded in the CNC), for example, $TiO_2$, $SiO_2$ (e.g., spherical shaped $SiO_2$), ZnO nanoparticles, gold nano particles, and/or core-shell nanoparticles. The nanoparticles are optionally selected to provide UV resistance and/or shine to the hair.

The nanoparticles may optionally comprise fluorescence quantum dots (e.g., as a colloid), for example, lead sulfide, lead selenide, cadmium selenide, and/or cadmium sulfide quantum dots.

Quantum dots are optionally covalently bound to the CNC, according to any of the embodiments described herein relating to covalent modification of CNC.

Quantum dots are semiconductor nanocrystals that exhibit unique optical properties, including color. As known in the art, the color properties of quantum dots are affected both by the chemical composition and the size of the quantum dots. For example, smaller dots emit bluer (higher energy) light.

Compositions:

The cellulose nanocrystals and/or resilin according to any of the embodiments presented herein can be utilized either per se, or, preferably, as a part of a composition comprising a suitable carrier.

According to an aspect of embodiments of the invention, there is provided a hair-straightening composition comprising modified and/or non-modified cellulose nanocrystals (according to any of the respective embodiments described herein), and a carrier suitable for application to hair.

According to an aspect of embodiments of the invention, there is provided a hair-straightening composition comprising resilin (according to any of the respective embodiments described herein), and a carrier suitable for application to hair. In some such embodiments, the hair-straightening composition is identified as being for use in maintenance of straightened hair following a hair-straightening treatment (e.g., a treatment according to any of the respective embodiments described herein), for example, in addition to, or rather than, being for use in a hair-straightening treatment per se. In some embodiments, the hair-straightening treatment comprises applying cellulose nanocrystals (e.g., according to any of the respective embodiments described herein).

Herein, the phrase "carrier suitable for application to hair" refers to a carrier or a diluent that does not cause significant irritation or cosmetically deleterious effects to an organism and does not abrogate the biological and/or cosmetic activity and properties of the administered agent.

Herein, the phrase "hair-straightening composition" encompasses any composition useful in a method of obtaining straighter hair, and is not intended to imply that the composition by itself is suitable for straightening hair. For example, as discussed herein, methods of straightening hair commonly utilize more than one composition, as well as physical processes such as applying heat and pressure.

The carrier may optionally comprise one or more excipients, that is, inert substance(s) added to a composition to further facilitate administration of a compound and/or processing of ingredients into preparations suitable for administration (e.g., onto hair). Examples, without limitation, of excipients include calcium carbonate, calcium phosphate, various sugars and types of starch, cellulose derivatives (e.g., other than cellulose nanocrystals), gelatin, vegetable oils, and polymers such as polyethylene glycols.

Techniques for formulation and administration of active agents may be found in "Remington's Pharmaceutical Sciences" Mack Publishing Co., Easton, PA, latest edition, which is incorporated herein by reference.

By selecting the appropriate carrier and optionally other ingredients that can be included in the composition, as is detailed herein, the hair-straightening compositions described herein may be formulated into any form typically employed for topical application such as application to hair. Hence, the hair-straightening compositions can be, for example, in a form of a cream, an ointment, a paste, a gel, a lotion, a milk, a suspension, an aerosol, a spray, a foam, a shampoo, a hair conditioner, a swab, a pledget, a pad, and a soap.

Ointments are semisolid preparations, typically based on vegetable oil (e.g. shea butter and/or cocoa butter), petrolatum or petroleum derivatives. The specific ointment base to be used is one that provides for optimum delivery for the hair-straightening agent chosen for a given formulation (e.g., cellulose nanocrystals and/or resilin), and, preferably, provides for other desired characteristics as well (e.g., emolliency). As with other carriers or vehicles, an ointment base should be inert, stable, nonirritating and nonsensitizing.

Lotions are preparations that may to be applied to the hair without friction. Lotions are typically liquid or semiliquid preparations in which solid particles, including the hair-straightening agent, are present in a water or alcohol base. Lotions are typically preferred for treating large areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the hair-straightening agent in contact with the hair.

Creams are viscous liquids or semisolid emulsions, either oil-in-water or water-in-oil. Cream bases typically contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant.

Pastes are semisolid dosage forms in which the hair-straightening agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base.

Gel formulations are semisolid, suspension-type systems. Single-phase gels contain organic macromolecules distributed substantially uniformly throughout the carrier liquid, which is typically aqueous, but also, preferably, contains a non-aqueous solvent and, optionally, an oil. Preferred organic macromolecules, i.e., gelling agents, are crosslinked acrylic acid polymers such as the family of carbomer polymers, e.g., carboxypolyalkylenes that may be obtained commercially under the trademark CARBOPOL™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the hair-straightening agent (e.g., cellulose nanocrystals and/or resilin) in an aqueous and/or volatile solvent solution which can be misted onto the hair for delivery. Such sprays include those formulated to provide for concentration of the hair-straightening agent solution at the site of administration following delivery, e.g., the spray solution can be primarily composed of a volatile liquid in which the hair-straightening agent can be dissolved. Upon delivery to the hair, the carrier evaporates, leaving concentrated hair-straightening agent at the site of administration.

Foam compositions are typically formulated in a single or multiple phase liquid form and housed in a suitable container, optionally together with a propellant which facilitates the expulsion of the composition from the container, thus transforming it into foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high volatile solvent content which, upon application to the hair of a user, quickly evaporates, leaving concentrated hair-straightening agent on the hair.

Representative examples of suitable carriers according to embodiments of the present invention therefore include, without limitation, water, liquid alcohols (optionally ethanol), liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic compositions.

The chemical composition of the carrier is typically selected according to the desired form of the hair-straightening composition. Further, the chemical composition of the carrier is selected so as to suit the desired purpose of the hair-straightening composition. For example, a composition for maintenance by repeated application (according to any of the respective embodiments described herein) may be selected to be milder (e.g., less irritating upon repeated application) and/or more convenient for use (e.g., home use) than a hair-straightening composition utilized in a single treatment (e.g., a treatment performed by a hairstyling professional). In addition, a hair-straightening composition utilized in a treatment comprising heat and pressure (according to any of the respective embodiments described herein) may be selected to be compatible with such conditions, whereas a composition for maintenance (according to any of the respective embodiments described herein) may not need to be compatible with such conditions. In addition, resilin may be sensitive to certain solvents to which celulose nanocrystals are resistant, and vice versa.

The carrier is optionally selected such that the composition is quick-drying, facilitating the spreading of the composition through the hair but minimizing dripping out of the hair and/or onto the scalp; non-harmful; and does not cause the hair to have an unappealing feel, appearance or aroma.

For example, dripping may be prevented by using a viscous carrier (e.g. cream, gel, foam), which is fluid enough to facilitate spreading through the hair, but sufficiently viscous so as to avoid dripping, as well as by using a quick-drying spray carrier, in which the carrier is sprayed onto the desired location, and then dries up before dripping out of the desired location.

Reflective compounds, such as silicone oils (e.g., disiloxane, dimethicone, and cyclomethicone), may be included in a carrier to provide hair with a glossy appearance.

Compositions of the present invention may, if desired, be presented (e.g., packaged) in a pack or dispenser device, such as an FDA (the U.S. Food and Drug Administration) approved kit, which may contain one or more compositions described herein. The pack or dispenser device may be accompanied by instructions for administration. The pack or dispenser may also be accompanied by a notice associated with the container in a form prescribed by a governmental agency regulating the manufacture, use or sale of cosmetics and/or pharmaceuticals, which notice is reflective of approval by the agency of the form of the compositions for human or veterinary administration. Such notice, for example, may be of labeling approved by the U.S. Food and Drug Administration. Compositions comprising cellulose nanocrystals and/or resilin (according to any of the respective embodiments described herein) may also be prepared, placed in an appropriate container (individually and/or together in a kit), and labeled for treatment of hair (e.g., according to any of the embodiments described herein).

In some of any of the embodiments described herein, a concentration of modified and/or non-modified CNC in a composition comprising same (e.g., a packaged composition) ranges from about 0.1% to about 5%, by weight, including any intermediate values and subranges therebetween. It is to be noted that higher concentrations are also contemplated and that such compositions may be diluted before application.

In some of any of the embodiments described herein, a concentration of a resilin in a composition (e.g., a packaged composition) comprising same ranges from about 0.1 mg/ml to about 200 mg/ml, including any intermediate values and subranges therebetween. It is to be noted that higher concentrations are also contemplated and that such compositions may be diluted before application.

According to some embodiments of the present invention, one or more of the other agents utilized in any of the methods described herein forms a part of a composition which further comprises a suitable carrier, as described herein for CNC and resilin. Such compositions are well known to those skilled in the art.

In some of any of the embodiments described herein, a concentration of a reducing agent in a composition (e.g., a packaged composition) comprising same ranges from about 1 mM to 2M, including any intermediate values and subranges therebetween. It is to be noted that higher concentrations are also contemplated and that such compositions may be diluted before application.

In some of any of the embodiments described herein, a concentration of a cationic agent in a composition (e.g., a packaged composition) comprising same ranges from about 0.1% to about 40%, by weight, including any intermediate values and subranges therebetween. It is to be noted that higher concentrations are also contemplated and that such compositions may be diluted before application.

In some of any of the embodiments described herein, a concentration of a cross-linking agent in a composition (e.g., a packaged composition) comprising same ranges from about 1 mg/ml to about 20 mg/ml, by weight, including any intermediate values and subranges therebetween. It is to be noted that higher concentrations are also contemplated and that such compositions may be diluted before application.

According to an aspect of some embodiments of the invention, there is provided a kit for straightening hair, the kit comprising, as separate containers:
- at least one container comprising cellulose nanocrystals or chemically modified cellulose nanocrystals (according to any of the respective embodiments described herein), or a composition comprising same; and
- at least one additional container comprising at least one additional composition for use in combination with cellulose nanocrystals (e.g., according to any of the respective embodiments described herein.

The additional container(s) may comprise, for example, a pre-treatment composition comprising at least one cationic agent (according to any of the respective embodiments described herein); and/or a composition comprising resilin (according to any of the respective embodiments described herein), e.g., optionally a composition for maintenance of straightened hair and/or at least one agent capable of cleaving disulfide bonds in hair according to any of the respective embodiments described herein.

In exemplary embodiments, the kit comprises:
- a first container comprising cellulose nanocrystals or chemically modified cellulose nanocrystals (according to any of the respective embodiments described herein), or a composition comprising same; and a second container comprising a pre-treatment composition comprising at least one cationic agent (according to any of the respective embodiments described herein).

In exemplary embodiments, the kit comprises:
a first container comprising cellulose nanocrystals or chemically modified cellulose nanocrystals (according to any of the respective embodiments described herein);
a second container comprising a pre-treatment composition comprising at least one cationic agent (according to any of the respective embodiments described herein); and
a third container a composition comprising resilin (according to any of the respective embodiments described herein).

In exemplary embodiments, the kit comprises:
a first container comprising cellulose nanocrystals or chemically modified cellulose nanocrystals (according to any of the respective embodiments described herein), or a composition comprising same; and
a second container a composition comprising resilin (according to any of the respective embodiments described herein).

In exemplary embodiments, the kit comprises:
a first container comprising cellulose nanocrystals or chemically modified cellulose nanocrystals (according to any of the respective embodiments described herein), or a composition comprising same;
a second container comprising a pre-treatment composition comprising at least one cationic agent (according to any of the respective embodiments described herein); and
a third container a composition comprising a composition for maintenance of straightened hair.

In exemplary embodiments, the kit comprises:
a first container comprising cellulose nanocrystals or chemically modified cellulose nanocrystals (according to any of the respective embodiments described herein), or a composition comprising same; and
a second container comprising a composition for maintenance of straightened hair.

In some of any of the above-described exemplary embodiments for a kit, the kit may further comprise an additional container comprising at least one agent capable of cleaving disulfide bonds in hair, as described herein in any of the respective embodiments, or a composition comprising same.

In some of any of the above-described exemplary embodiments for a kit, the kit may further comprise an additional container comprising a cross-linking agent, as described herein in any of the respective embodiments, or a composition comprising same.

In any of the kits described herein, the concentration of the agent (reducing agent, cationic agent, CNC, resilin, and any modifications and combinations thereof) can be a final concentration for use in the intended application, or a higher concentration which is diluted prior to application. In some embodiments, the kit may further comprise one or more suitable carriers for diluting the agents, and optionally means for performing the dilution, for example, a receptacle with measuring units, means to mix the diluted composition, and the like.

In some embodiments, any of the kits described herein further comprises instructions how to use the agents or compositions included therein, and in some embodiments, such instructions are in accordance with any of the respective methods described herein. The instructions may further include diluting one or more of the agents/compositions and instructions with a suitable carrier how to perform the dilution. The instructions may further include mixing one or more of the agents/compositions before application and instructions how to perform the mixing.

In some embodiments, the kit may further comprise means for mixing one or more of the agents/compositions before application.

In some of the any of the embodiments described herein for a kit, one or more of the containers in the kit is configured for dispensing a composition directly to the hair. For example, a container can be configured for dispensing a composition by means of a spray or a foam, or be a squeeze-bottle which dispenses the composition via a nozzle. Any other means for dispensing the composition are contemplated, depending on the composition.

In some of the any of the embodiments described herein for a kit, the kit, or one or more of the containers therein, may further include means for applying the composition to the hair, for example, a dedicated brush, sponge, gauze, pledget, etc.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, cosmetic, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.
Material:
Arginine was obtained from Sigma-Aldrich.
BTMS (behentrimonium methosulfate) was obtained from Roga Cosmetics.
Cetrimonium chloride was obtained from Emilia Cosmetics.
Chitosan was obtained from Sigma-Aldrich.
CNC (cellulose nanocrystals) was obtained from Melodea Ltd.
Cysteine was obtained from Sigma-Aldrich.
Gelatin was obtained from was obtained from Sigma-Aldrich.
Hydro-keratin was obtained from Helion Ltd.
MES (2-(N-morpholino)ethanesulfonic acid) was obtained from Sigma-Aldrich.
Polylysine was obtained from Sigma-Aldrich.
SDS (sodium dodecyl sulfate) was obtained from Bio-Lab Ltd.
SHP (sodium hypophosphite) was obtained from Sigma-Aldrich.
SLS-free shampoo was obtained from Mommy Care Ltd.
SMBS (sodium metabisulfite) was obtained from Sigma-Aldrich.
Resilin Production:
Resilin with a fused cellulose binding domain (RES-CBD) was prepared according to procedures similar to those described in International Patent Application Publication WO 2015/068160, Qin et al. [*Biomacromolecules* 2009, 10:3227-3234], International Patent Application Publication WO 2009/069123, and Qin et al. [*Biomaterials* 2011, 32:9231-9243].

Recombinant resilin was produced as a histidine-tagged (6H) chimeric protein composed of *D. melanogaster* resilin exon 1 (17 elastic repeats) fused to an N-terminal histidine tag, and to *C. cellulovorans* cellulose binding domain (CBD).

The 6H-res-CBD gene was cloned into a pHis-parallel3 expression vector, which confers ampicillin resistance upon its host. A lysogeny broth-agar plate containing ampicillin was streaked with a glycerol stock of *E. coli* bacteria strain BL-21(DE3) star (Invitrogen Carlsbad, CA) containing the expression vector pHis-parallel3_6H-17res-CBD, and incubated overnight (ON) at 37° C. A single colony was used for the inoculation of 200 ml M9 minimal media containing glucose (0.8% w/v) and ampicillin (100 mg/liter). The culture was grown in a rotary shaker (12 h, 250 rpm, 35° C.) until an optical density at 600 nm (OD 600 nm) of ~3. Next, bacteria culture (2% v/v) was used to inoculate a bench fermentor (New Brunswick Scientific, Edison, NJ, USA) containing 10 liters of TB, glucose (0.8% w/v), ampicillin (100 mg/liter), and antifoam "B" emulsion (4 ml of 1:3 diluted stock). The fermentor was operated at 400 rpm and 35° C., with an air flow rate of 5 vvm and air pressure of 10 psi. Protein expression was induced at OD 600 nm~8 (the mid-log phase) by the addition of isopropyl b-D-1-thiogalactopyranoside (IPTG), at a final concentration of 0.5 mM. Anti-foaming agent was added in small doses (1 ml) whenever necessary. Finally, 4 hour post-induction (OD 600 nm~18), bacteria were harvested by centrifugation (10,000 rpm, 4° C.) and stored at −80° C. until further use. Total bacterial samples (pre- and post-IPTG induction) were collected and analyzed by SDS-PAGE (12%) and western blot analysis.

Bacterial pellets were thawed at 4° C. and homogenized in a lysis buffer containing sodium phosphate (25 mM, pH 7.5) and NaCl (150 mM). Next, the homogenized bacteria were sonicated (80% amplitude, 50% pulse time, 40 minutes; 500 V UIP1000hd industrial sonicator (Hielscher, Germany)) on ice, and the soluble fraction was separated by centrifugation (11,000 rpm, 30 minutes, 20° C.). The soluble fraction was removed, and the pellet containing the 6H-res-CBD in the form of inclusion bodies (IBs) was washed once with sodium phosphate (25 mM, pH 7.5), NaCl (150 mM) and Triton X-100 (0.8 wt %) buffer followed by one additional washing step using a sodium phosphate (25 mM, pH 7.5) and NaCl (150 mM) detergent-free buffer. The IBs containing 6H-res-CBD were then dissolved in sodium phosphate (20 mM, pH 11.8) and the soluble fraction was collected (and diluted to ~2 mg/ml using the same buffer) for protein refolding. Refolding of the protein was carried out via a drop-wise addition of 1M HCl until reaching a pH of 8-9.

Cellulose Nanocrystal Modification:
Aldehyde-CNC (CNC modified to comprise surface aldehyde groups) was prepared as follow: The pH of a 2% CNC suspension was adjusted to a range of 2.5-3. 2 of grams $NaIO_4$ (sodium periodate) were dissolved in 100 ml of the 2% CNC suspension (1:1 weight ratio), and the suspension was stirred for 24 hours at room temperature, so as to convert glucose residues in cellulose to dialdehyde residues by oxidative cleavage. About 10 ml of ethylene glycol was then added in order to stop the reaction. The suspension was dialyzed against distilled water for about 3 days, thereby obtaining aldehyde-CNC.

In all of the Examples below, and unless otherwise indicated, whenever a modified or non-modified CNC is employed, it is employed either per se or in combination with a cross-linking agent as described herein.

Scanning Electron Microscopy (SEM) Measurements:

SEM images were obtained by A Jeol JSM 5410 Scanning Electron microscope, samples preparation was performed using Polaron SEM Coating Unit.

Example 1

Effect of Cellulose Nanocrystals on Hair Undergoing Straightening Treatment

Healthy curly hair samples were subjected to following hair care treatments for hair straightening, in order to assess the effect of cellulose nanocrystals (CNC). Following treatments (and for some samples, repeated washes subsequent to treatment), the hair was analyzed visually and using scanning electron microscopy (SEM).

Sample 1-1—Control sample (untreated), followed by repeated washes: Natural curly hair was washed with soapless soap. Treated hair samples were then washed with water 19 times, once per day. 28 days from the beginning of treatment, the samples were washed with regular shampoo 6 times, and then analyzed using SEM.

Sample 1-2—5 mM SMBS+0.01% poly-Lys+CNC, followed by repeated washes: Natural curly hair was washed with water and soapless soap and partially air dried. 5 mM of sodium metabisulfite (SMBS) was applied on the hair (spread on the hair samples) and left for 15 minutes. Hair samples were then fan-dried and straightened with a hot iron. SMBS was again spread on the hair and left for 15 minutes. The hair was washed with water, fan-dried and straightened with a hot iron. 0.01% polylysine (poly-Lys) was spread onto the hair and air-dried. The hair was washed with water and fan-dried. CNC was spread onto the hair, which was air-dried and straightened very slowly for 5-6 minutes with a hot iron. The hair was washed with water, fan-dried, washed again with water and air-dried. Treated hair samples were then washed with water 19 times, once per day. 28 days from the beginning of treatment, the samples were washed with regular shampoo 6 times, and then analyzed using SEM.

Sample 1-3—0.5% SDS+1% NaCl+5 mM SMBS+0.5 M cysteine+2% cetrimonium chloride: Natural curly hair was washed with shampoo and conditioner and air-dried. Hair samples were washed again with 0.5% sodium dodecyl sulfate (SDS) and 1% NaCl, and then, 5 mM sodium metabisulfite was applied on the hair (spread on the hair samples using a lice comb) and left for 10 minutes. The hair was then fan-dried and straightened with a hot iron. 0.5 M cysteine was added (spread on the hair samples using a lice comb) and left for 10 minutes. 2% cetrimonium chloride was added (spread on the hair samples using a lice comb), and the hair was partially air-dried for 30 minutes, fan-dried and straightened with a hot iron. Hair was washed with water and air-dried.

Sample 1-4—0.5% SDS+1% NaCl: Natural curly hair was washed with shampoo and conditioner and then air-dried. Hair samples were washed again with 0.5% SDS and 1% NaCl and air-dried.

Sample 1-5—0.5% SDS+1% NaCl+5 mM SMBS+0.5 M cysteine+2% cetrimonium chloride+CNC: Natural curly hair was washed with shampoo and conditioner and air-dried. Hair samples were washed again with 0.5% SDS and 1% NaCl, and then, 5 mM sodium metabisulfite (SMBS) was applied on the hair (spread on the hair samples using a lice comb) and left for 10 minutes. The hair was then fan-dried and straightened with a hot iron. 0.5 M cysteine was added (spread on the hair samples using a lice comb) and left for 10 minutes. 2% cetrimonium chloride was added (spread on the hair samples using a lice comb), and the hair was partially air dried for 30 minutes, fan-dried and straightened with a hot iron. Hair was washed with water, and CNC was spread onto the hair with a lice comb. The hair was partially air-dried for 30 minutes and fan-dried. The hair was then straightened slowly for 2 minutes with a hot iron (with the help of a lice comb). The hair was then washed with water and air-dried.

Figure 2:
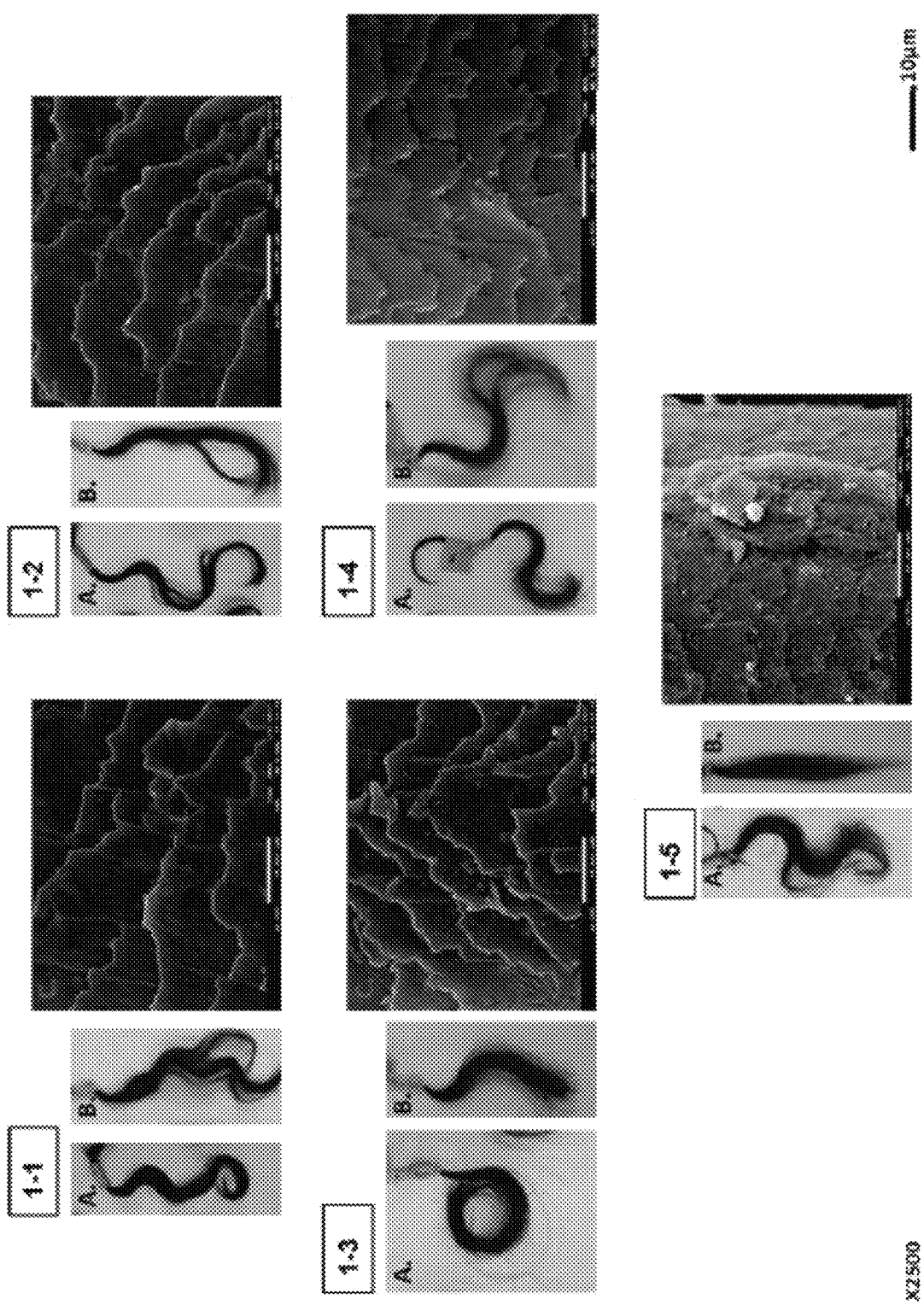
FIG. 2 presents photographic images of hair samples before (A) and after (B) treatment, and scanning electron micrographic images at ×2500 magnification (C) of the same treated hair samples as depicted in FIG. 1.
Figure 3:
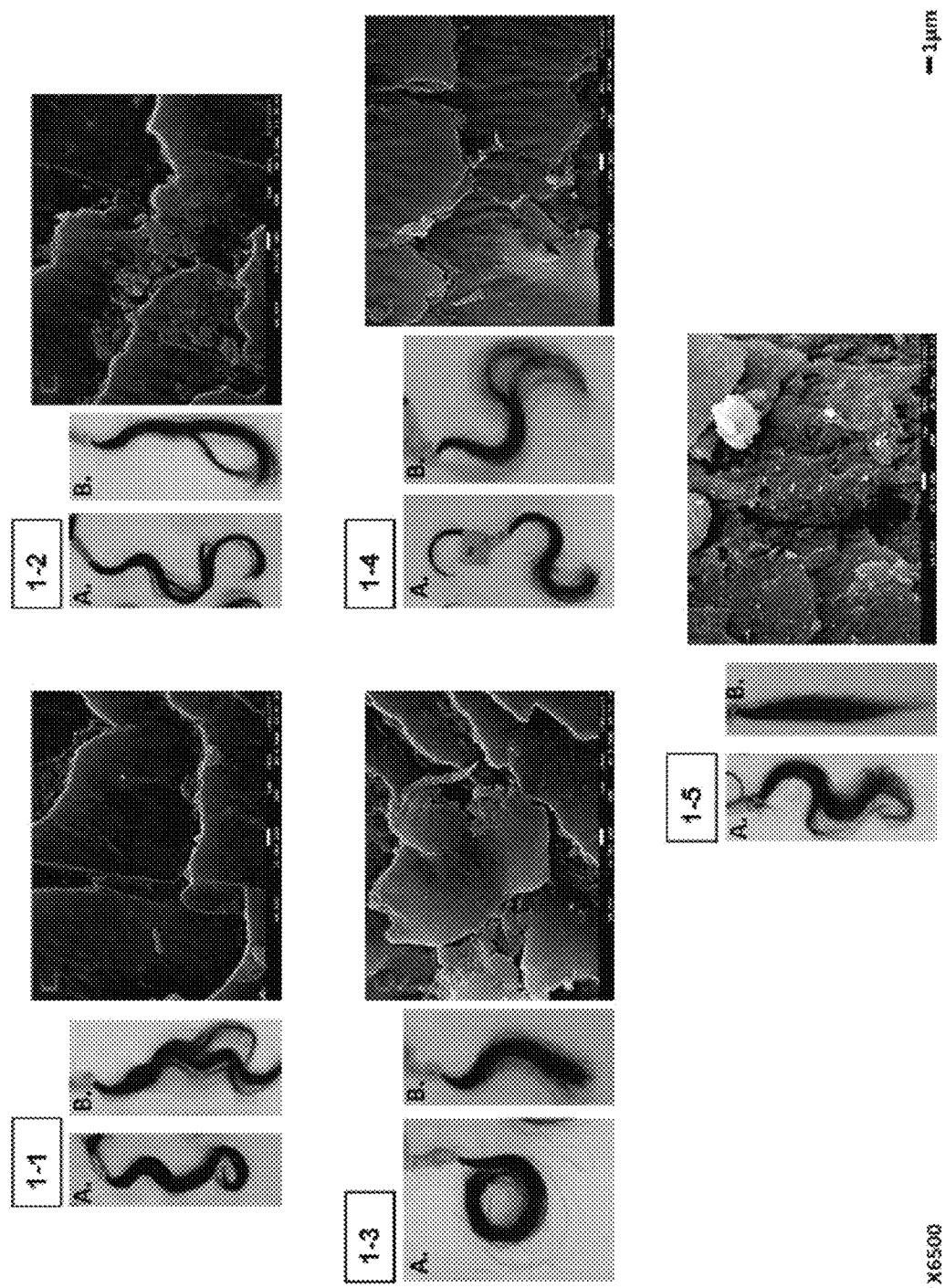
FIG. 3 presents photographic images of hair samples before (A) and after (B) treatment, and scanning electron micrographic images at ×6500 magnification (C) of the same treated hair samples as depicted in FIG. 1.

As shown in FIGS. 1-3, the use of CNC in combination with a disulfide-reducing agent (SMBS and/or cysteine) in hair treatment (e.g., Sample 1-5) was associated with a greater degree of hair straightening than obtained for hair treatment with disulfide-reducing agent without CNC (e.g., Sample 1-3), as well as in the presence of a layer coating the hair surface after treatment (observable by electron microscopy). As further shown therein, the effect of treatment with CNC was weaker following repeated washing of the hair (e.g., Sample 1-2).

These results indicate that application of CNC enhances hair straightening, and suggests that the effect of CNC is associated with formation of a layer coating the hair surface.

Healthy curly hair samples were further subjected to various hair care treatments for hair straightening (involving 5 mM sodium metabisulfite), in order to assess the long-term effect of cellulose nanocrystals (CNC). Following treatments, hair samples were washed with water 9 or 19 times, once per day, and then washed with regular shampoo 8 times (on 8 different days).

Sample 2-1—5 mM SMBS+200 mM cysteine+2% chitosan+CNC: Natural curly hair was washed with water and soapless soap and air-dried. Hair samples were straightened using hot iron, and then, 5 mM sodium metabisulfite (SMBS) was applied on the hair (spread on the hair samples). 200 mM cysteine was added immediately, and the hair was partially air-dried for 15 minutes and fan-dried. The hair was washed with water, fan-dried and straightened with a hot iron. 2% chitosan was spread onto the hair with a lice comb, and the hair was air-dried for 1 hour and then fan-dried. The hair was washed with water, fan-dried and straightened with a hot iron. CNC was spread onto the hair with a lice comb, and the hair was partially air-dried for 30 minutes and fan-dried. The hair was straightened very slowly for 6 minutes with a hot iron (with the help of a lice comb), washed with water and air-dried. The hair sample was washed with water 9 times, then washed with regular shampoo on days 15, 16, 19, 20, 21, 24, 25 and 26, and analyzed on day 27.

Sample 2-2—5 mM SMBS+200 mM cysteine: Natural curly hair was washed with water and soapless soap and air-dried. Hair samples were straightened with a hot iron, and then, 5 mM sodium metabisulfite (SMBS) was applied on the hair (spread on the hair samples). 200 mM cysteine was added immediately and the hair was partially air-dried for 15 minutes. The sample was fan dried and washed with water, and then again fan-dried, straightened with a hot iron, washed with water and air-dried. The hair sample was washed with water 9 times, then washed with regular shampoo on days 15, 16, 19, 20, 21, 24, 25 and 26, and analyzed on day 27.

Sample 2-3—5 mM SMBS+2% chitosan (new, prepared in 5% vinegar+0.2 M NaCl)+CNC: Natural curly hair was washed with water and soapless soap and air-dried. The hair sample was straightened using a hot iron, and then, 5 mM sodium metabisulfite (SMBS) was applied on the hair (spread on the hair samples). SMBS was left on the hair for 15 minutes, and the hair was then fan-dried and straightened with a hot iron. 2% chitosan was spread onto the hair with a lice comb, and the hair was partially air-dried for 1 hour, fan-dried and washed with water. The hair was then again fan-dried and straightened with a hot iron. CNC was spread onto the hair with a lice comb, and the hair was partially air dried for 30 minutes and fan-dried. The hair sample was straightened very slowly for 6 minutes with a hot iron (with the help of a lice comb), then washed with water and air-dried. The hair sample was washed with water 9 times, then washed with regular shampoo on days 15, 16, 19, 20, 21, 24, 25 and 26, and analyzed on day 27.

Sample 2-4—5 mM SMBS+2% chitosan: Natural curly hair was washed with water and soapless soap and air-dried. 5 mM sodium metabisulfite (SMBS) was applied on the hair (spread on the hair samples) and left for 15 minutes. The hair was fan-dried and straightened with a hot iron. SMBS was again spread on the hair and left for 15 minutes. The hair was washed with water, fan-dried and straightened with a hot iron. 2% chitosan was spread onto the hair, which was then partially air-dried for 1 hour and fan-dried. The hair was washed with water and air-dried. The hair sample was washed with water 19 times, then washed with regular shampoo on days 24, 25, 29, 30, 31, 34, 35 and 36, and analyzed on day 37.

Sample 2-5·5 mM SMBS+2% chitosan+CNC: Natural curly hair was washed with water and soapless soap and air-dried. 5 mM sodium metabisulfite (SMBS) was applied on the hair (spread on the hair samples) and left for 15 minutes. The hair was fan-dried and straightened with a hot iron. SMBS was again spread on the hair and left for 15 minutes. The hair was washed with water, fan-dried and straightened with a hot iron. 2% chitosan was spread onto the hair, which was then partially air-dried for 1 hour and fan-dried. The hair was washed with water and fan-dried. CNC was spread onto the hair, which was then partially air-dried for 30 minutes and fan-dried. The hair was straightened very slowly for 6 minutes with a hot iron, and then washed with water, fan-dried, washed again with water and air-dried. The hair sample was washed with water 19 times, then washed with regular shampoo on days 24, 25, 29, 30, 31, 34, 35 and 36, and analyzed on day 37.

Figure 4:
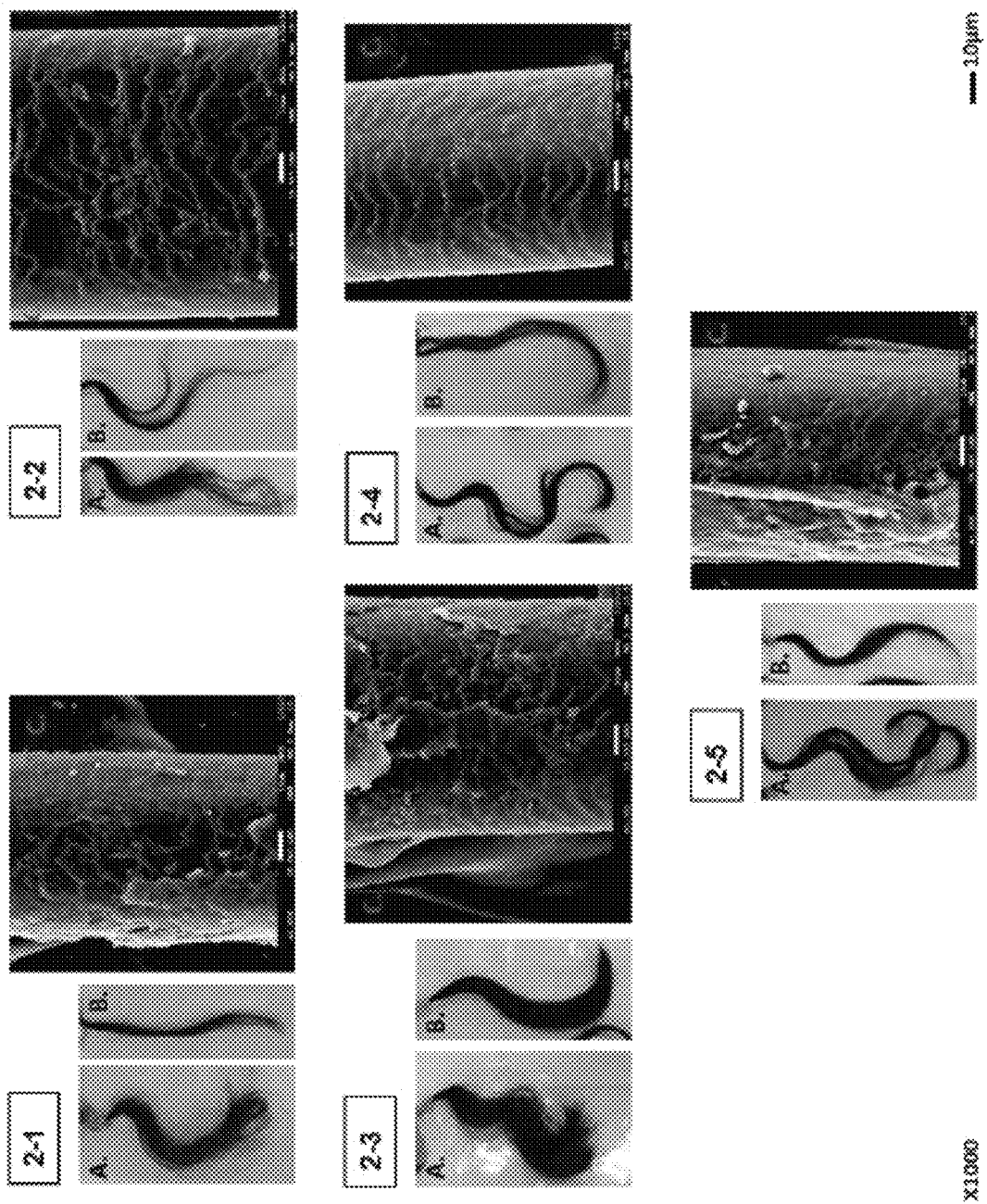
FIG. 4 presents photographic images of hair samples before (A) and after (B) treatment, and scanning electron micrographic images at ×1000 magnification (C) of the hair samples after a hair-straightening treatment using 5 mM SMBS+200 mM Cys+2% chitosan+CNC (Sample 2-1), 5 mM SMBS+200 mM Cys (Sample 2-2), 5 mM SMBS+2% chitosan (in 5% vinegar+0.2 M NaCl)+CNC (Sample 2-3), 5 mM SMBS+2% chitosan (Sample 2-4), or 5 mM SMBS+2% chitosan+CNC (Sample 2-5).
Figure 5:
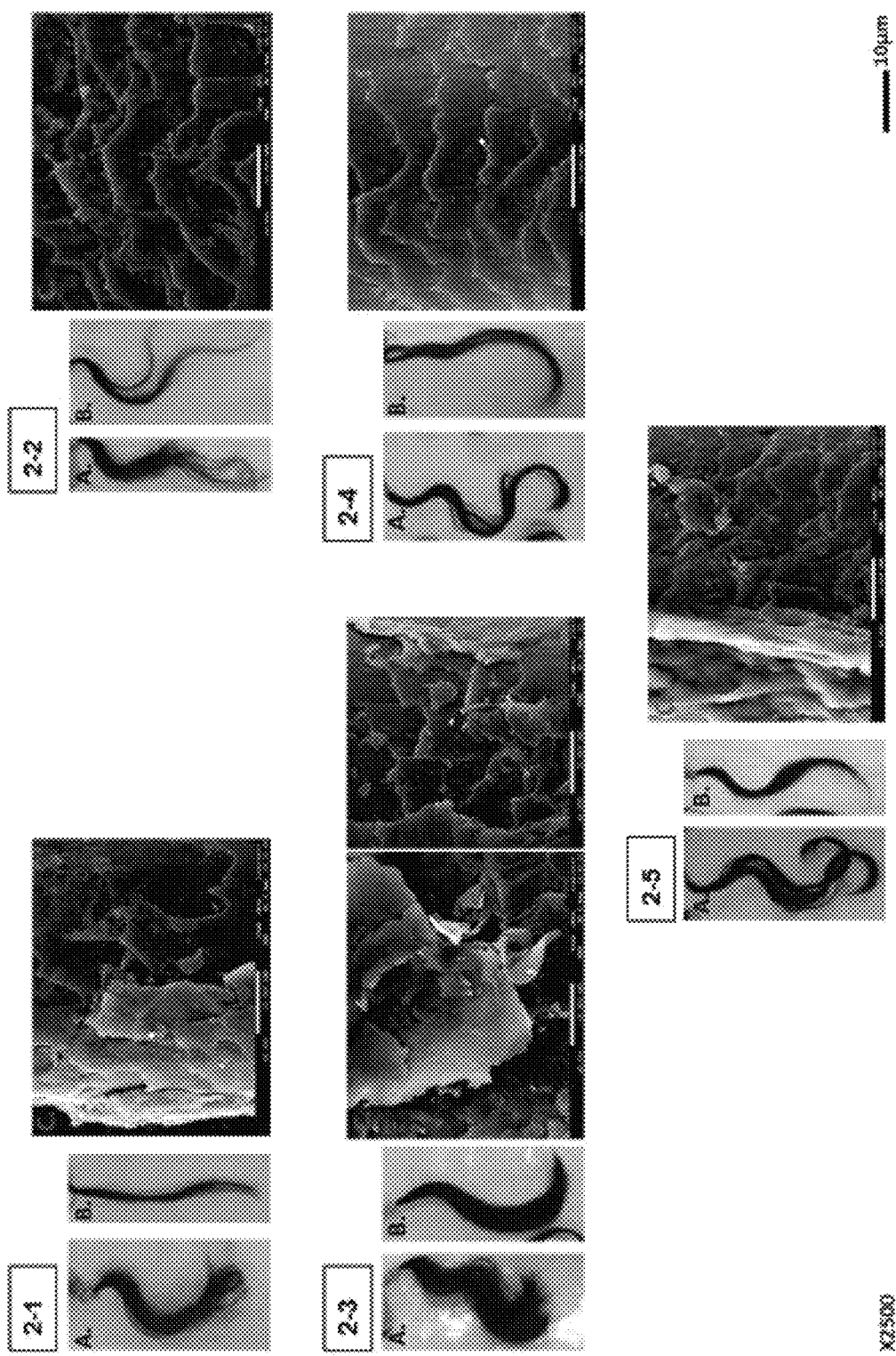
FIG. 5 presents photographic images of hair samples before (A) and after (B) treatment, and scanning electron micrographic images at ×2500 magnification (C) of the same treated hair samples as depicted in FIG. 4.
Figure 6:
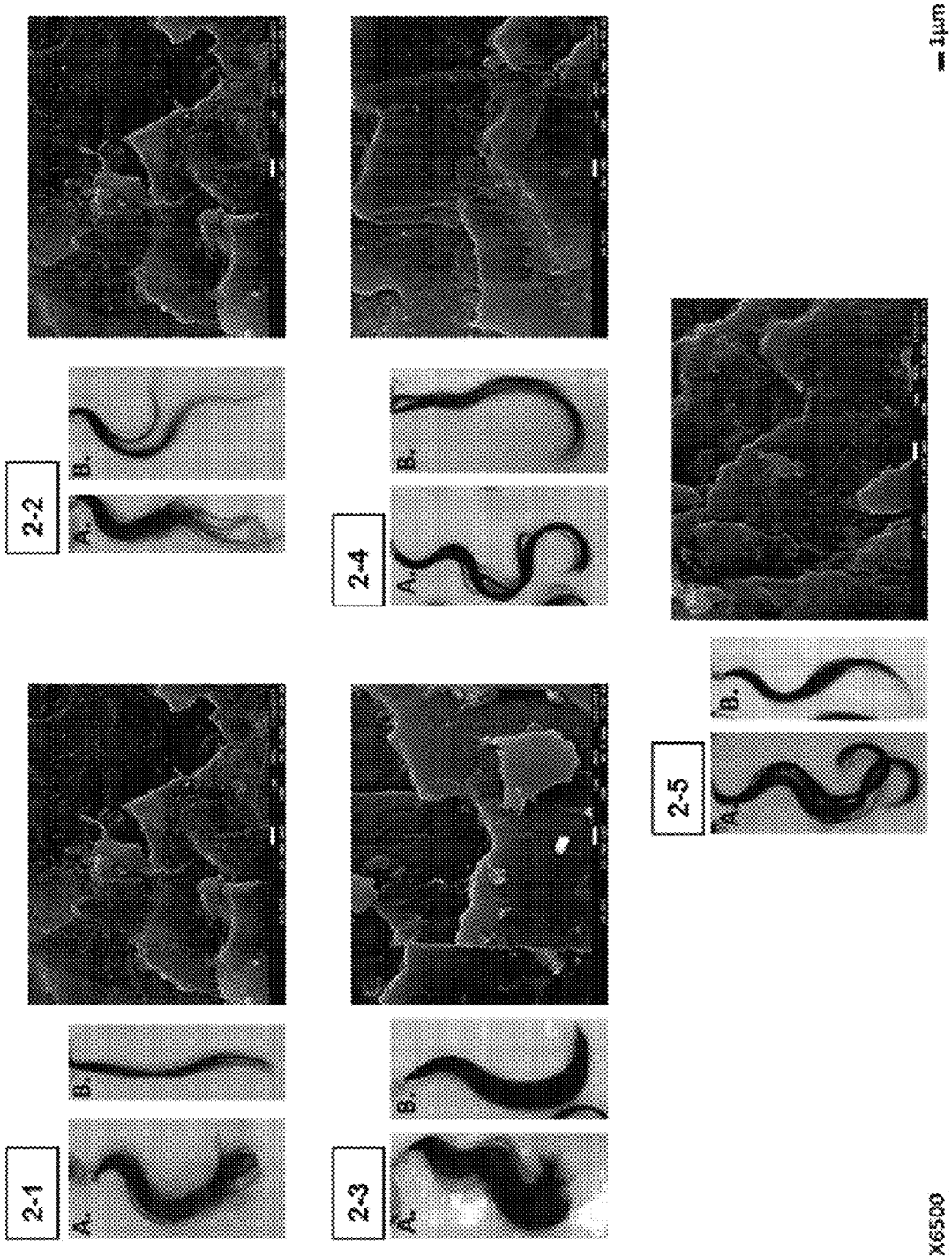
FIG. 6 presents photographic images of hair samples before (A) and after (B) treatment, and scanning electron micrographic images at ×6500 magnification (C) of the same treated hair samples as depicted in FIG. 4.
Figure 7:
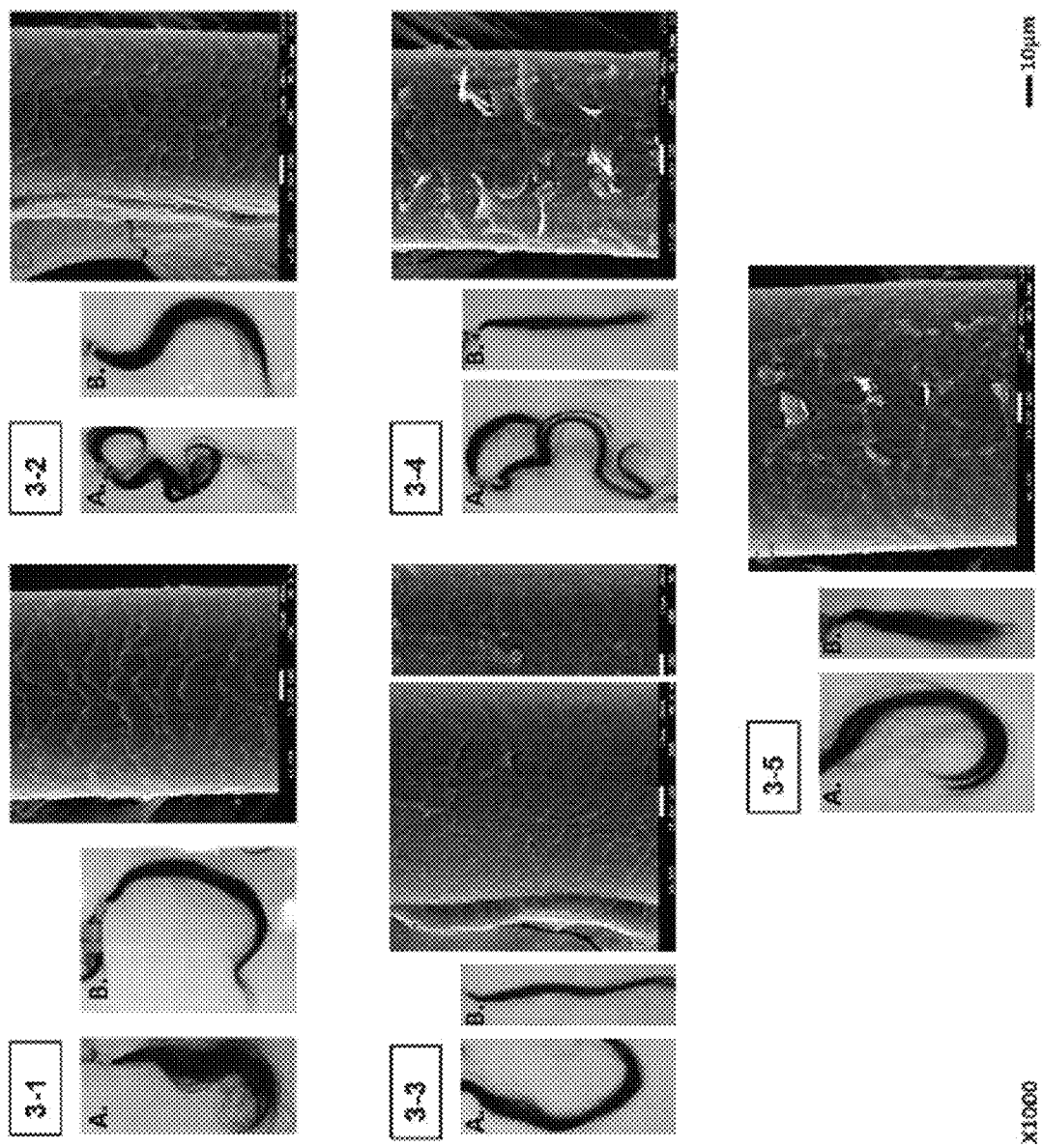
FIG. 7 presents photographic images of hair samples before (A) and after (B) treatment, and scanning electron micrographic images at ×1000 magnification (C) of the hair samples after a hair-straightening treatment using 5 mM SMBS+aldehyde-CNC (Sample 3-1), 5 mM SMBS+0.5 M Cys+2% gelatin (Sample 3-2), 5 mM SMBS+0.5 M Cys+2% chitosan+CNC (Sample 3-3), 5 mM SMBS+0.5 M Arg+CNC (Sample 3-4), or 5 mM SMBS+0.5 M Cys+2% gelatin+CNC (Sample 3-5).
Figure 8:
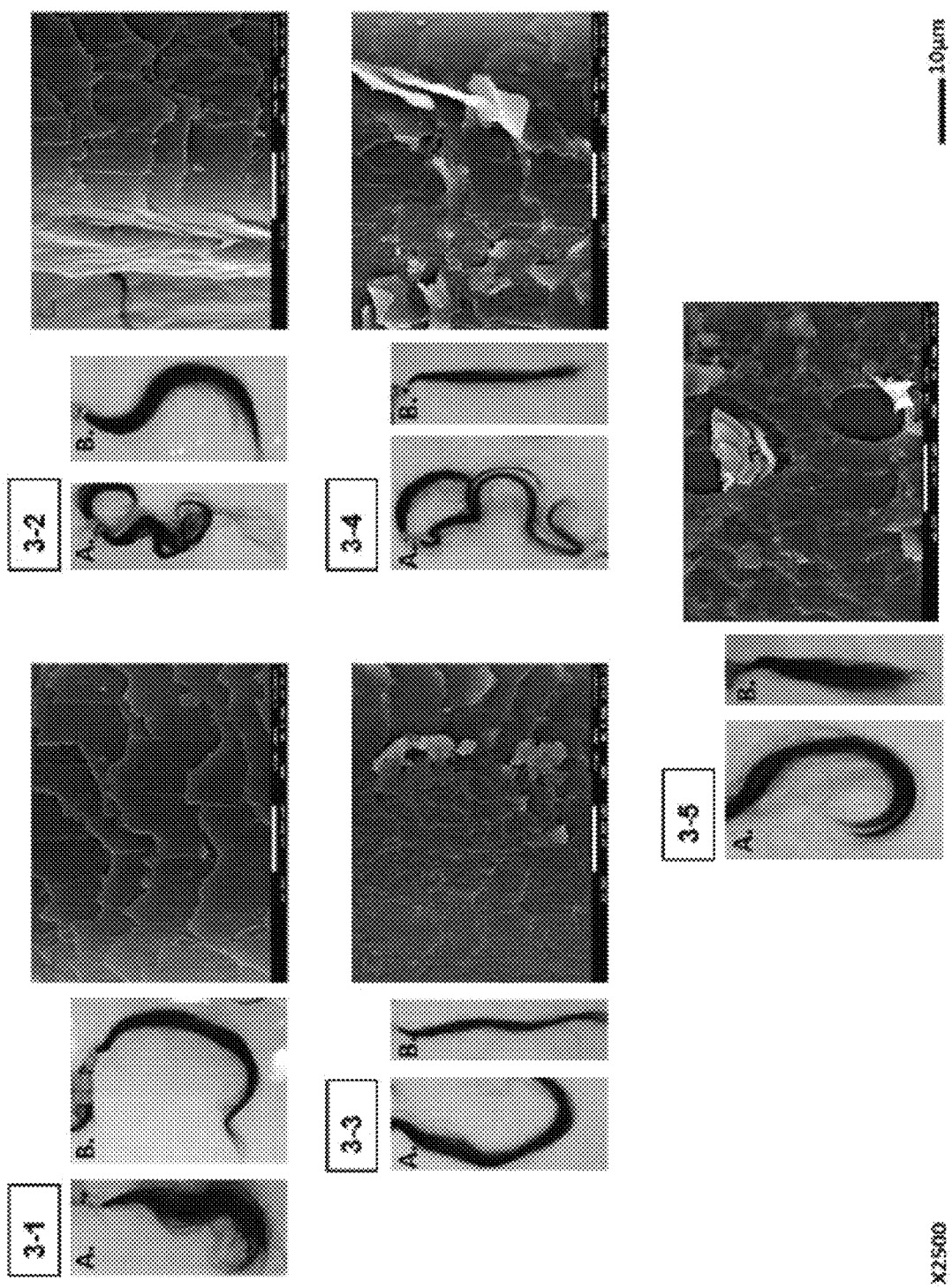
FIG. 8 presents photographic images of hair samples before (A) and after (B) treatment, and scanning electron micrographic images at ×2500 magnification (C) of the same treated hair samples as depicted in FIG. 7.
Figure 9:
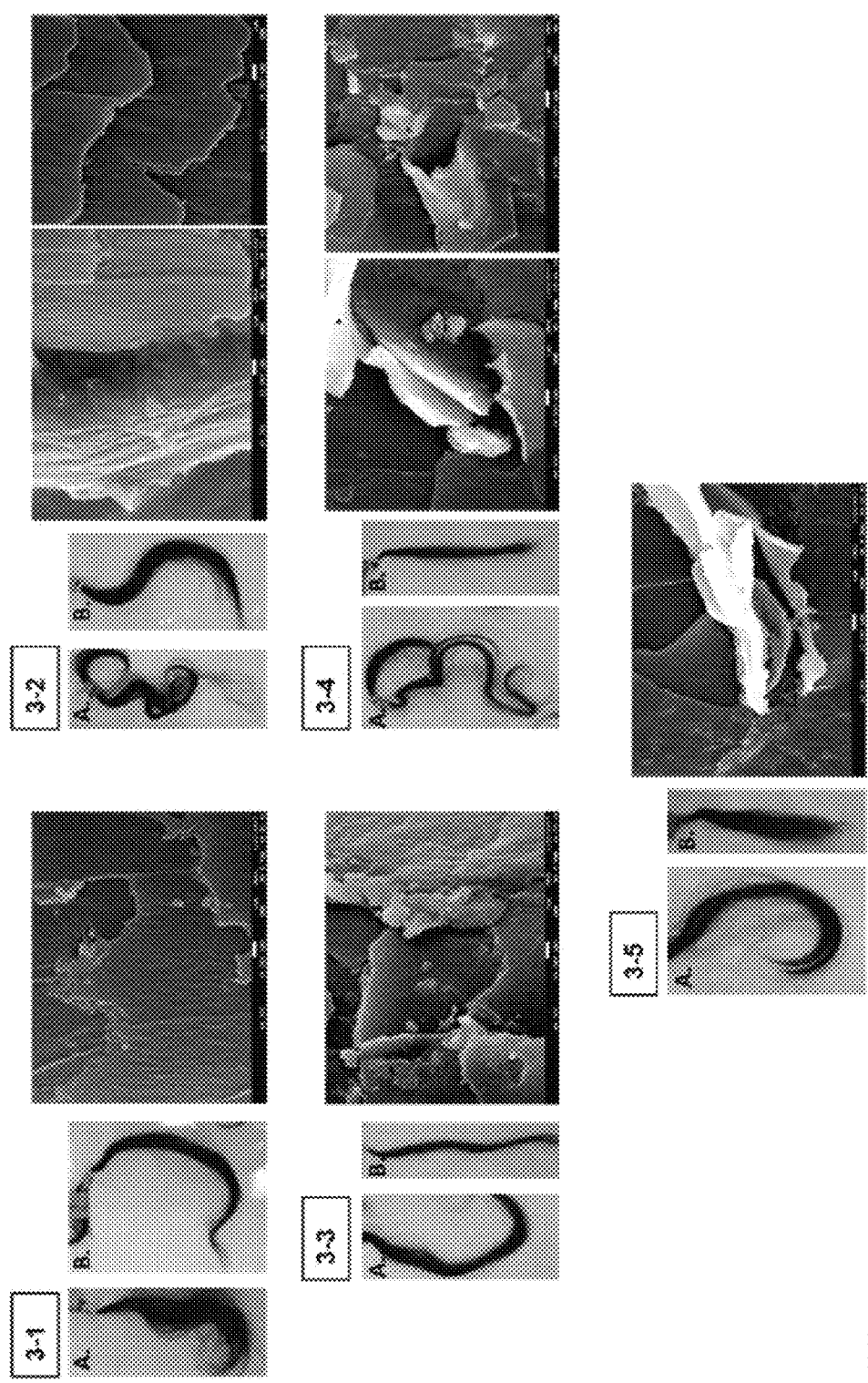
FIG. 9 presents photographic images of hair samples before (A) and after (B) treatment, and scanning electron micrographic images at ×6500 magnification (C) of the same treated hair samples as depicted in FIG. 7.
Figure 10:
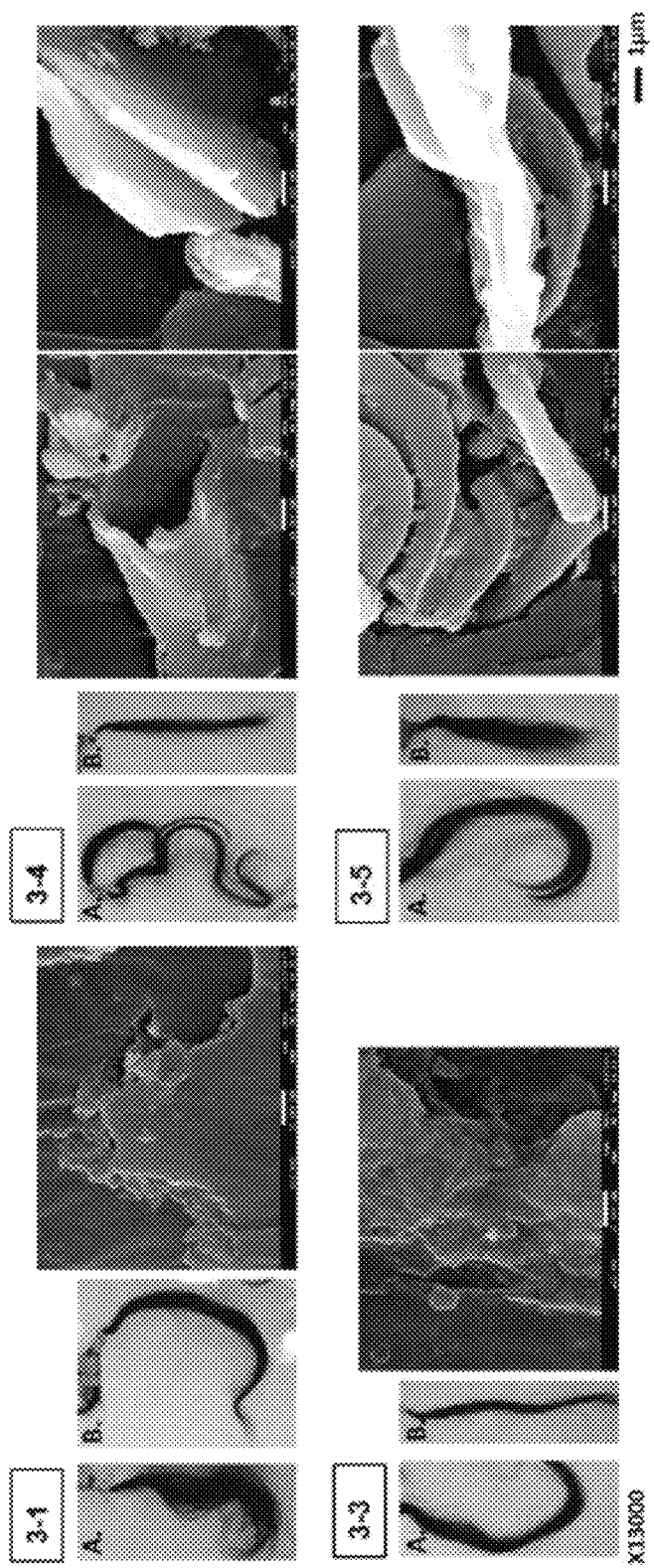
FIG. 10 presents photographic images of hair samples before (A) and after (B) treatment, and scanning electron micrographic images at ×13000 magnification (C) of the same treated hair samples as depicted in FIG. 7.

As shown in FIGS. 4-6, the use of CNC in combination with SMBS and/or cysteine in hair treatment (Samples 2-1, 2-3 and 2-5) was associated with a greater degree of hair straightening than obtained upon corresponding hair treatment with SMBS without CNC (Samples 2-2 and 2-4), as well as in the presence of a layer coating the hair surface after treatment (observable by electron microscopy). As further shown therein, the effect of treatment with CNC was maintained over the course of several weeks with repeated washings.

These results indicate that application of CNC enhances the permanence of hair straightening.

Healthy curly hair samples were further subjected to various hair care treatments for hair straightening (involving 5 mM sodium metabisulfite), followed by a regimen of regular washing, in order to further assess the long-term effect of cellulose nanocrystals (CNC).

Sample 3-1—5 mM SMBS+aldehyde-CNC: Natural curly hair was washed with water and soapless soap and air-dried. Hair samples were straightened using a hot iron, and then, 5 mM sodium metabisulfite (SMBS) was applied on the hair (spread on the hair samples) and left for 15 minutes, and the hair was then fan-dried and straightened with a hot iron. Aldehyde-CNC (prepared as described hereinabove) was spread onto the hair with a lice comb, and the hair was partially air-dried for 30 minutes and fan-dried. The hair was straightened using a hot iron (with the help of a lice comb), washed with water and air-dried. The hair sample was washed with water 9 times (once a day), and then washed with regular shampoo on days 15, 16, 19, 20, 21, 24, 25 and 26, and analyzed on day 27.

Sample 3-2—5 mM SMBS+0.5 M Cys+2% gelatin: Natural curly hair was washed with shampoo and conditioner and then fan-dried. The hair sample was straightened using a hot iron, and then, 5 mM sodium metabisulfite (SMBS) was applied on the hair (spread on the hair sample) and 0.5 M cysteine was added and left for 15 minutes. The hair was then fan-dried, straightened with a hot iron and washed with water, and again fan-dried and straightened with a hot iron. 0.5 M cysteine was added again, and 2% gelatin was spread onto the hair with a lice comb; and the hair was air-dried for 30 minutes and fan-dried, and then washed with water and air-dried. The hair sample was washed with water 10 times, on days 1, 2, 3, 4, 7, 8, 9, 12, 13 and 14, and analyzed on day 15.

Sample 3-3—5 mM SMBS+0.5 M Cys+2% chitosan+CNC: Natural curly hair was washed and treated with SMBS, cysteine and chitosan as described hereinabove for Sample 3-2, except that 2% chitosan was used instead of 2% gelatin. After application of the chitosan, the hair was air-dried for 30 minutes and fan-dried, and then washed with water, fan-dried and iron-straightened. CNC was then spread onto the hair with a lice comb, and the hair was partially air-dried for 30 minutes and fan-dried. The hair was then straightened slowly for 2 minutes with a hot iron (with the help of a lice comb) and then washed with water and air-dried. The hair sample was washed with water twice (on days 1 and 2) and with regular shampoo on days 4, 7, 8, 9, 12, 13 and 14, and analyzed on day 15.

Sample 3-4—5 mM SMBS+0.5 M Cys+0.5 M Arg+CNC: Natural curly hair was washed with shampoo and conditioner and then fan-dried. The hair sample was straightened using a hot iron, and then, 5 mM sodium metabisulfite (SMBS) was applied on the hair (spread using a lice comb) and 0.5 M cysteine was added, and immediately thereafter, 0.5 M arginine was added and left on the hair for 15 minutes. The hair was then fan-dried and hot iron-straightened, then washed with water and fan-dried. 0.5 M cysteine and 0.5 M arginine were added again, and left on the hair for 30 minutes, which was then fan-dried and straightened with a hot iron. CNC was then spread onto the hair with a lice comb, and the hair was partially air-dried for 30 minutes and fan-dried. The hair was then straightened slowly for 2 minutes with a hot iron (with the help of a lice comb) and then washed with water and air-dried. The hair sample was washed with water 10 times, on days 1, 2, 3, 4, 7, 8, 9, 12, 13 and 14, and analyzed on day 15.

Sample 3-5—5 mM SMBS+0.5 M Cys+2% gelatin+CNC: Natural curly hair was washed and treated with SMSBS, cysteine and gelatin as described hereinabove for Sample 3-2. After the application of gelatin, the hair was partially air-dried for 30 minutes, fan-dried, and straightened with a hot iron. CNC was then spread onto the hair with a lice comb, and the hair was partially air-dried for 30 minutes and fan-dried. The hair was then straightened slowly for 2 minutes with a hot iron (with the help of a lice comb) and then washed with water and air-dried, and again washed with water and air-dried. The hair sample was washed with water 10 times, on days 1, 2, 3, 4, 7, 8, 9, 12, 13 and 14, and analyzed on day 15.

As shown in FIGS. 7-10, the use of CNC in combination with SMBS and/or cysteine in hair treatment (e.g., Samples 3-3, 3-4 and 3-5) was associated with a greater degree of hair straightening than obtained upon similar treatments with SMBS without CNC (Sample 3-2), as well as in the presence of a layer coating the hair surface after treatment (observable by electron microscopy). As further shown therein, the effect of treatment with CNC was maintained over the course of several weeks with repeated washings.

These results further confirm that application of CNC enhances the permanence of hair straightening.

Example 2

Effect of Resilin Application to Hair Straightened Using Cellulose Nanocrystals

Healthy curly hair was subjected to hair straightening using cysteine and cellulose nanocrystals (CNC), followed by various secondary treatments over the course of three weeks, in order to assess the effect of different secondary treatments on maintenance of the effects of the hair-straightening treatment.

Cysteine was used as a reducing agent to break disulfide bonds in the keratin structure. In order to maintain keratin unattached by disulfide bonds, hydro-keratin (hydrolyzed keratin) was added. Positively charged molecules—arginine and the cationic surfactant BTMS (behentrimonium methosulfate)—were used to facilitate interaction of CNC with the hair surface.

Hair was washed with regular shampoo, fan-dried and subjected to the straightening treatment. A mixture of 1 M cysteine in a 100 mM MES (2-(N-morpholino)ethanesulfonic acid) solution at pH 3.5 and hydro-keratin was applied on the hair sample, spread on the hair, and left in the hair at 37° C. until semi-dried (15-30 minutes), after which the hair was dried with a hot fan. The hair was then washed with water, fan-dried and straightened at a temperature of 190° C. 0.5 M arginine in 1% BTMS was spread on the hair and left at 37° C. for 15-30 minutes and fan-dried. Hair was straightened at a temperature of 190° C., and 3% CNC was spread on the hair and left at 37° C. until semi-dried (15-30 minutes), after which the hair was fan-dried until completely dry and straightened at a temperature of 190° C., then washed with water and air-dried.

For about 2.5 weeks after hair-straightening, the hair was washed only with water (double-distilled) and then with SLS (sodium laureth sulfate)-free shampoo.

During the following week, the hair was washed with 4 mg/ml RES-CBD (resilin with a cellulose binding domain) in water and then 2 mg/ml RES-CBD in water.

For the next two weeks, the hair was washed with SLS-free shampoo and 1 mg/ml RES-CBD in water (2-3 times per week).

The hair was then treated by applying a 50 mg/ml RES-CBD solution and letting the hair dry with the applied RES-CBD, followed by washing with water.

For about 3 more weeks, the hair was treated (every 2-3 days) alternately by washing with SLS-free shampoo followed by 2 mg/ml RES-CBD in water, or by applying a 10 mg/ml RES-CBD solution and letting the hair dry.

At various stages of the treatment, the hair was examined several hours after the most recent treatment, when it was completely dry.

Figure 11:
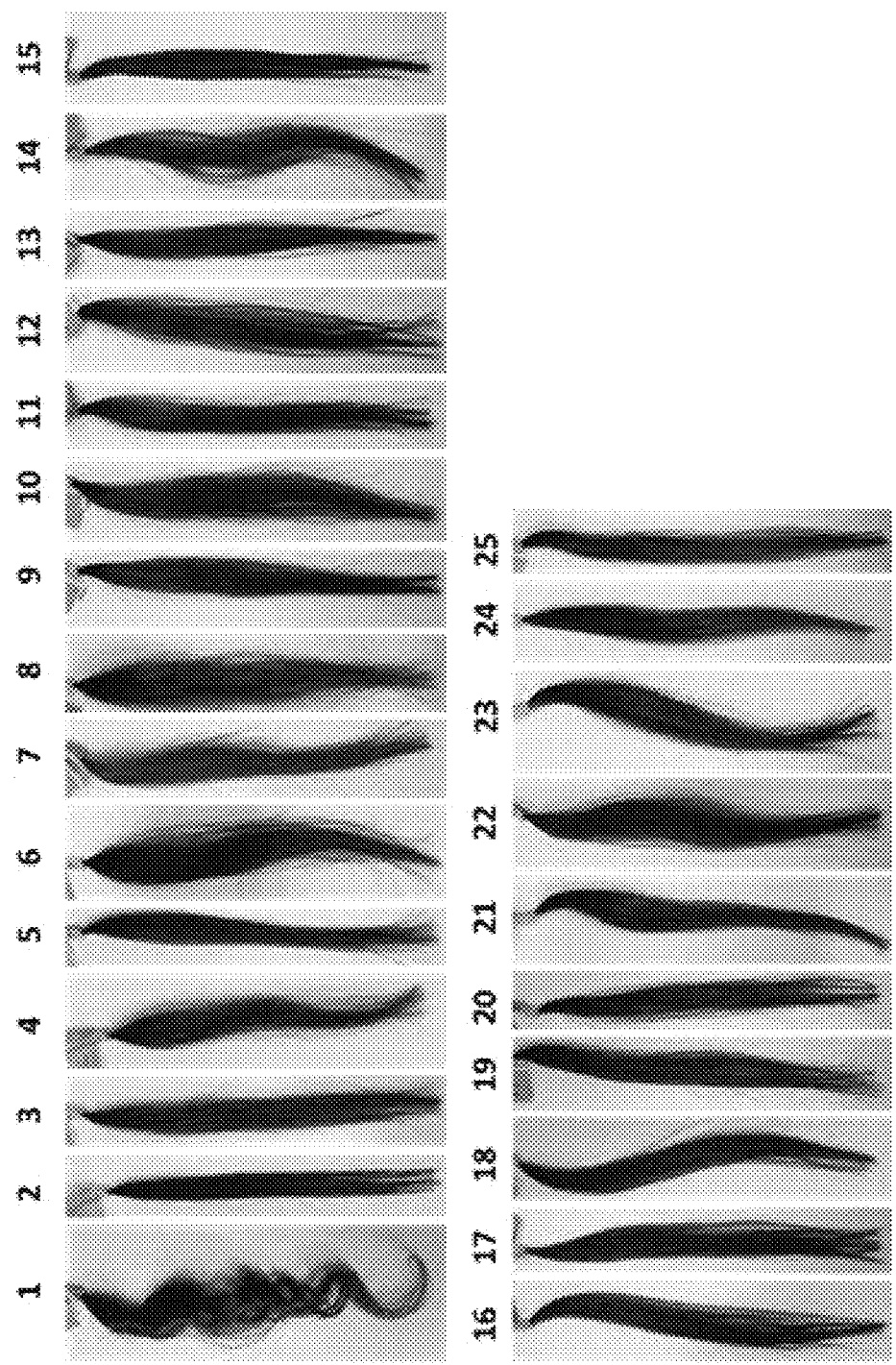
FIG. 11 presents photographic images of a hair sample before and at successive stages after a hair straightening treatment (using 1 M cysteine, 0.5 M arginine in 1% BTMS, and 3% CNC), as follows: before (image 1) and immediately after (image 2) treatment, after washing with water (image 3) and 5 times with SLS-free shampoo (images 4, 5, 6, 7, 8) over the course of about 2.5 weeks after treatment, followed by washing with 4 mg/ml (image 9) and 2 mg/ml (image 10) RES-CBD (resilin with cellulose binding domain) in water over the course of one week, and washing 4 times with SLS-free shampoo and 1 mg/ml RES-CBD in water over the course of 2 weeks (images 11, 12, 13, 14), followed by application of 50 mg/ml RES-CBD (image 15), and (over the course of about 3 weeks) alternating washes with SLS-free shampoo and 2 mg/ml RES-CBD in water (images 16, 18, 21, 22 and 25), application of 10 mg/ml RES-CBD (images 17, 19, 20, 23, 24) (images 19 and 23 show hair before washing with water after RES-CBD treatment, and images 17, 20 and 24 show hair after washing with water).

As shown in FIG. 11, the straightened hair gradually lost its straightened form during the initial period in which it was washed only with water or shampoo (images 3-8), whereas subsequent washing with 1-4 mg/ml resilin temporarily enhanced the straightened appearance (images 9-13) until the sixth wash with resilin (image 14). The appearance of the hair was then restored by treatment with a high concentration (50 mg/ml) of resilin left on the hair to dry (image 15). Subsequently, the appearance of the hair was enhanced when resilin was applied and deteriorated when washed with shampoo (images 16-25).

These results indicate that resilin applied to straightened hair restores and maintains the effects of the hair-straightening for at least several weeks after hair-straightening treatment.

Example 3

Effect of Resilin Application to Previously Straightened Hair

The effectiveness of resilin maintenance treatment was further assessed by applying resilin from about 3 weeks to about 3 months after a variety of hair-straightening treatments Hair was washed with regular shampoo, fan-dried and iron-straightened. 0.5 M cysteine was applied on the hair and left for 15 minutes, and the hair was then fan-dried, washed with water, fan-dried and iron-straightened. 0.5 M cysteine was applied on the hair again, and immediately thereafter, 0.5 M arginine was added and left on the hair for another 30 minutes. The hair was then fan-dried and iron-straightened. CNC was applied on the hair, which was then partially air-dried for 30 minutes, then fan-dried and slowly iron-straightened, and then washed with water and air-dried. The hair was subsequently washed with water once, with 0.5% SDS (sodium dodecyl sulfate) and 1% NaCl five times, and with regular shampoo 21 times.

About 3 months after the straightening treatment, a 10 mg/ml solution of RES-CBD was applied to the hair and left to dry. At intervals of two days, the hair was subsequently:
washed with water and air-dried;
washed with SLS-free shampoo and air-dried; and
again washed with SLS-free shampoo and air-dried.

Figure 12:
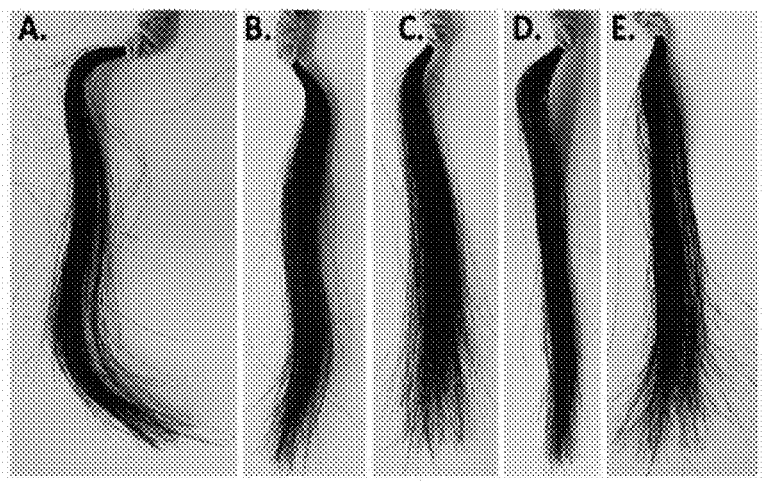
FIG. 12 presents photographic images of a hair sample about 3 months after an exemplary hair straightening treatment, before (FIG. 12A) and several hours after (FIG. 12B) application of 10 mg/ml RES-CBD (resilin with cellulose binding domain) in water, followed by washing (at intervals of 2 days) with water (FIG. 12C), SLS-free shampoo (FIG. 12D), and again with SLS-free shampoo (FIG. 12E).
Figure 13:
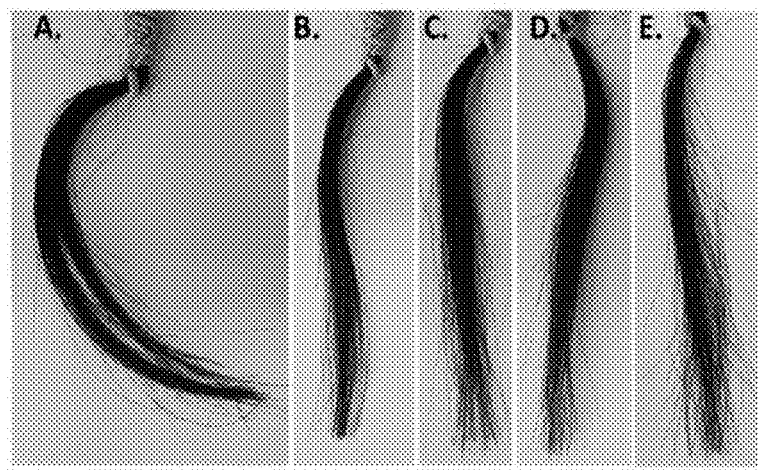
FIG. 13 presents photographic images of a hair sample about 3 months after an exemplary hair straightening treatment, before (FIG. 13A) and several hours after (FIG. 13B) application of 10 mg/ml RES-CBD (resilin with cellulose binding domain) in water, followed by washing (at intervals of 2 days) with water (FIG. 13C), SLS-free shampoo (FIG. 13D), and again with SLS-free shampoo (FIG. 13E).

As shown in FIGS. 12 and 13, the application of resilin was effective at restoring and maintaining the effect of the previous straightening treatment.

In an additional experiment, hair was washed with regular shampoo, air-dried and iron straightened. 0.5 M cysteine was applied on the hair and left for 15 minutes. 0.5 M cysteine was then applied on the hair again, and immediately thereafter, 0.5 M arginine was added and left on the hair for another 30 minutes. The hair was then fan-dried and iron-straightened. CNC was applied on the hair, which was then partially air-dried for 30 minutes, then fan-dried and slowly iron-straightened, and then washed with water and air-dried. The hair was subsequently washed with water once and with regular shampoo 20 times.

About 2 months after the straightening treatment, a 10 mg/ml solution of RES-CBD was applied to the hair and left to dry, followed by washing once with water and twice with SLS-free shampoo, as described hereinabove.

Figure 14:
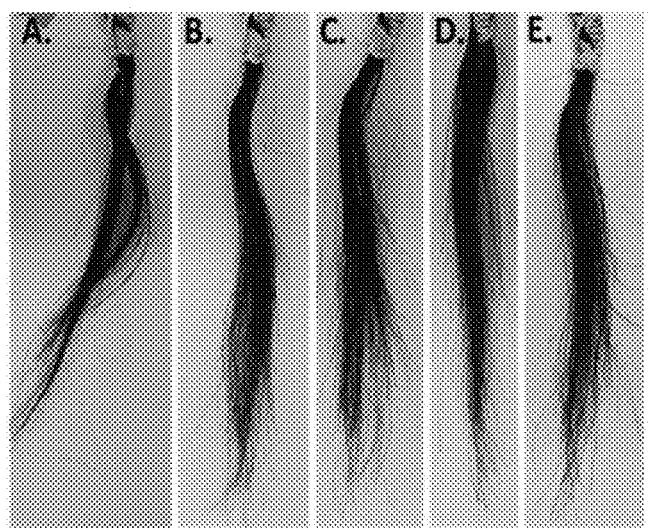
FIG. 14 presents photographic images of a hair sample about 2 months after an exemplary hair straightening treatment, before (FIG. 14A) and several hours after (FIG. 14B) application of 10 mg/ml RES-CBD (resilin with cellulose binding domain) in water, followed by washing (at intervals of 2 days) with water (FIG. 14C), SLS-free shampoo (FIG. 14D), and again with SLS-free shampoo (FIG. 14E).

As shown in FIG. 14, the application of resilin was effective at restoring and maintaining the effect of the previous straightening treatment.

In an additional experiment, naturally curly hair was washed with regular shampoo and then with a shampoo comprising 0.5% SDS, 1% NaCl, 5% glycerol and 2% polyethylene glycol distearate, and then fan-dried and iron-straightened. 5 mM sodium metabisulfite was then applied on the hair (spread using a lice comb) and left for 15 minutes. The hair was then washed with water. 0.5 M cysteine was then applied on the hair, and immediately thereafter, 0.5 M arginine was added and left on the hair for 15 minutes. The hair was then fan-dried and hot iron-straightened, and 0.5 M cysteine and 0.5 M arginine were applied again and left in the hair for 30 minutes. The hair was then washed fan-dried and iron-straightened. The hair was subsequently washed with water four times and 0.5% SDS and 1% NaCl three times.

About 3 weeks after the straightening treatment, a 10 mg/ml solution of RES-CBD was applied to the hair and left to dry, followed by washing once with water and twice with SLS-free shampoo, as described hereinabove.

Figure 15:
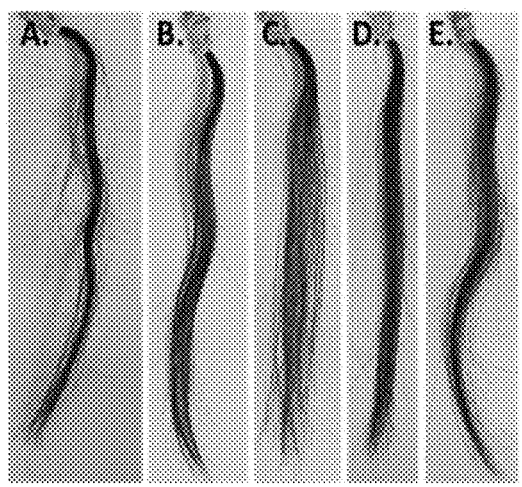
FIG. 15 presents photographic images of a hair sample about 3 weeks after an exemplary hair straightening treatment, before (FIG. 15A) and several hours after (FIG. 15B) application of 10 mg/ml RES-CBD (resilin with cellulose binding domain) in water, followed by washing (at intervals of 2 days) with water (FIG. 15C), SLS-free shampoo (FIG. 15D), and again with SLS-free shampoo (FIG. 15E).

As shown in FIG. 15, the application of resilin was effective at restoring and maintaining the effect of the previous straightening treatment (which did not involve CNC).

In an additional experiment, naturally curly hair was washed with regular shampoo and conditioner, and air-dried; and then washed again with 0.5% SDS and 1% NaCl. 5 mM sodium metabisulfite was then applied on the hair (spread using a lice comb) and left for 10 minutes and then fan-dried and hot iron-straightened. 0.5 M cysteine was then applied on the hair (spread using a lice comb) and left on the hair for 10 minutes. 2% cetrimonium chloride was added (spread using a lice comb) and the hair was partially air-dried for 30 minutes, then fan-dried, hot iron-straightened, and washed with water. CNC was spread onto the hair with a lice comb, and the hair was partially air-dried for 30 minutes, then fan-dried, iron-straightened slowly for 2 minutes (with the help of a lice comb), washed with water and air-dried. The hair was subsequently washed with 0.5% SDS and 1% NaCl nine times and with regular shampoo twice.

About one month after the straightening treatment, a 10 mg/ml solution of RES-CBD was applied to the hair and left to dry, followed by washing once with water and twice with SLS-free shampoo, as described hereinabove.

Figure 16:
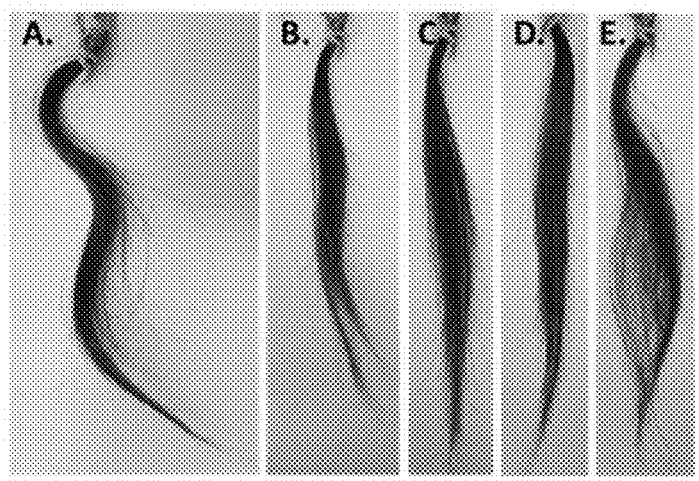
FIG. 16 presents photographic images of a hair sample about one month after an exemplary hair straightening treatment, before (FIG. 16A) and several hours after (FIG. 16B) application of 10 mg/ml RES-CBD (resilin with cellulose binding domain) in water, followed by washing (at intervals of 2 days) with water (FIG. 16C), SLS-free shampoo (FIG. 16D), and again with SLS-free shampoo (FIG. 16E).

As shown in FIG. 16, the application of resilin was effective at restoring and maintaining the effect of the previous straightening treatment.

In an additional experiment, naturally curly hair was washed with water and soapless soap and then air dried. The hair was then iron-straightened, and 5 mM sodium metabisulfite was then applied on the hair by spreading, and left on the hair for 15 minutes. Immediately thereafter, 200 mM cysteine was added to the hair, which was then fan-dried and washed with water, fan-dried gain, and hot iron-straightened. 2% chitosan was then spread onto the hair with a lice comb, and the hair was air-dried for 1 hour and then fan-dried, washed with water, fan-dried again, and hot iron-straightened. CNC was spread onto the hair with a lice comb, and the hair was partially air-dried for 30 minutes, then fan-dried, iron-straightened very slowly for 6 minutes (with the help of a lice comb), washed with water and air-dried. The hair was subsequently washed with water eight times, with regular shampoo 15 times, and with shampoo comprising 0.5% SDS, 1% NaCl, 5% glycerol and 2% polyethylene glycol distearate three times.

About 3 months after the straightening treatment, a 10 mg/ml solution of RES-CBD was applied to the hair and left to dry, followed by washing once with water and twice with SLS-free shampoo, as described hereinabove.

Figure 17:
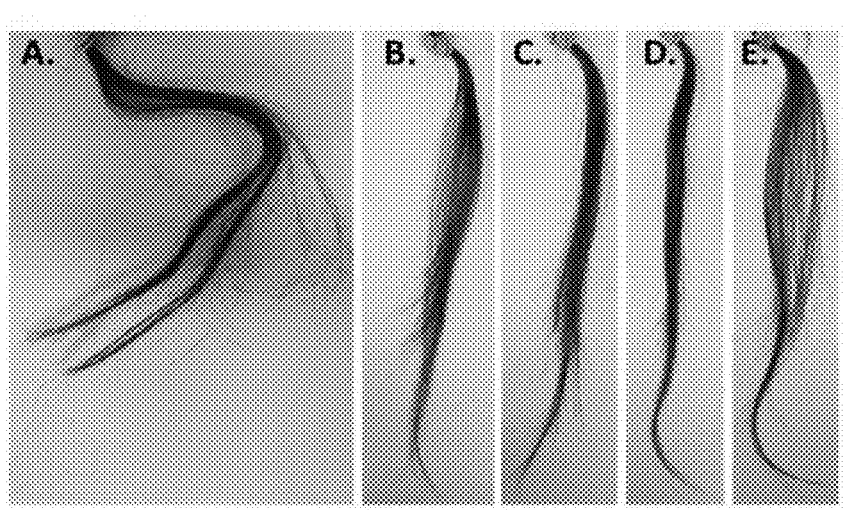
FIG. 17 presents photographic images of a hair sample about 3 months after an exemplary hair straightening treatment, before (FIG. 17A) and several hours after (FIG. 17B) application of 10 mg/ml RES-CBD (resilin with cellulose binding domain) in water, followed by washing (at intervals of 2 days) with water (FIG. 17C), SLS-free shampoo (FIG. 17D), and again with SLS-free shampoo (FIG. 17E).

As shown in FIG. 17, the application of resilin was effective at restoring and maintaining the effect of the previous straightening treatment.

In an additional experiment, hair was washed with regular shampoo, fan-dried and straightened. A mixture of 0.5 M cysteine, 0.5 M arginine and 2% CNC was spread onto the hair and left for 1 hour. The hair was then fan-dried and straightened, washed with water and air-dried. The hair was subsequently washed with regular shampoo eight times.

About one month after the straightening treatment, a 10 mg/ml solution of RES-CBD was applied to the hair and left to dry, followed by washing once with water and twice with SLS-free shampoo, as described hereinabove.

Figure 18:
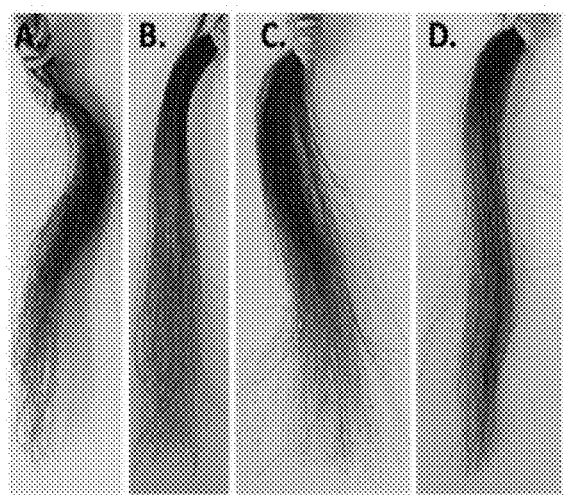
FIG. 18 presents photographic images of a hair sample about one month after an exemplary hair straightening treatment, before (FIG. 18A) and several hours after (FIG. 18B) application of 10 mg/ml RES-CBD (resilin with cellulose binding domain) in water, followed by washing (at intervals of 2 days) with water (FIG. 18C) and SLS-free shampoo (FIG. 18D).

As shown in FIG. 18, the application of resilin was effective at restoring and maintaining the effect of the previous straightening treatment.

In an additional experiment, naturally curly hair was washed with regular shampoo and conditioner and then fan-dried. The hair was then iron-straightened, and 5 mM sodium metabisulfite was then applied on the hair (spread using a lice comb). 0.5 M cysteine was added, and immediately thereafter 0.5 M arginine was added and left on the hair for 15 minutes; and the hair was then fan-dried and hot iron-straightened. The hair was then washed with water, fan-dried, and hot iron-straightened. 0.5 M cysteine and 0.5 M arginine were added again and left on the hair for 30 minutes, followed by fan-drying and iron-straightening the hair. CNC was spread onto the hair with a lice comb, and the hair was partially air-dried for 30 minutes, then fan-dried, iron-straightened slowly for 2 minutes (with the help of a lice comb), washed with water and air-dried. The hair was subsequently washed with water four times, with 0.5% SDS and 1% NaCl six times, with shampoo comprising 0.5% SDS, 1% NaCl, 5% glycerol and 2% polyethylene glycol distearate three times, and with regular shampoo twice.

About 1.5 months after the straightening treatment, a 10 mg/ml solution of RES-CBD was applied to the hair and left to dry, followed by washing once with water and twice with SLS-free shampoo, as described hereinabove.

Figure 19:
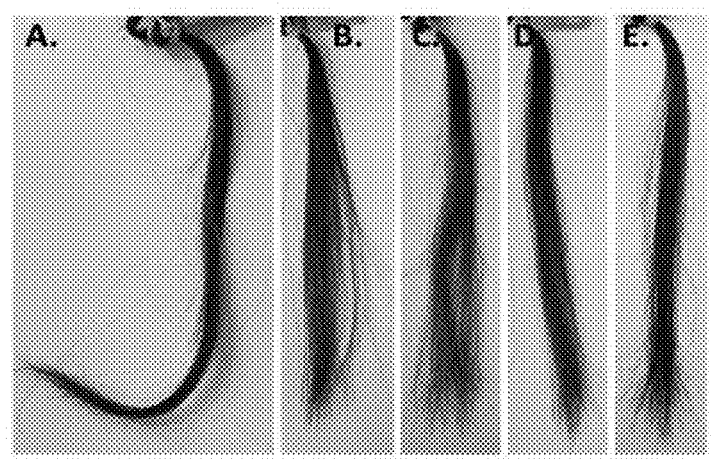
FIG. 19 presents photographic images of a hair sample about 1.5 months after an exemplary hair straightening treatment, before (FIG. 19A) and several hours after (FIG. 19B) application of 10 mg/ml RES-CBD (resilin with cellulose binding domain) in water, followed by washing (at intervals of 2 days) with water (FIG. 19C), SLS-free shampoo (FIG. 19D), and again with SLS-free shampoo (FIG. 19E).

As shown in FIG. 19, the application of resilin was effective at restoring and maintaining the effect of the previous straightening treatment.

In an additional experiment, naturally curly hair was washed with regular shampoo and conditioner and then fan-dried. The hair was then iron-straightened, and 5 mM sodium metabisulfite was then applied on the hair (spread using a lice comb). 0.5 M cysteine was added and left on the hair for 15 minutes, and the hair was then fan-dried and hot iron-straightened. The hair was then washed with water, fan-dried, and hot iron-straightened. 0.5 M cysteine was added again and 2% chitosan was spread onto the hair with a lice comb. The hair was then air-dried for 30 minutes and fan-dried, and then washed with water, fan-dried and iron straightened. CNC was spread onto the hair with a lice comb, and the hair was partially air-dried for 30 minutes, then fan-dried, iron-straightened slowly for 2 minutes (with the help of a lice comb), washed with water and air-dried. The hair was subsequently washed with water once, with regular shampoo 15 times, with shampoo comprising 0.5% SDS, 1% NaCl, 5% glycerol and 2% polyethylene glycol distearate three times, and then again with regular shampoo twice.

About 2 months after the straightening treatment, a 10 mg/ml solution of RES-CBD was applied to the hair and left to dry, followed by washing once with water and twice with SLS-free shampoo, as described hereinabove.

Figure 20:
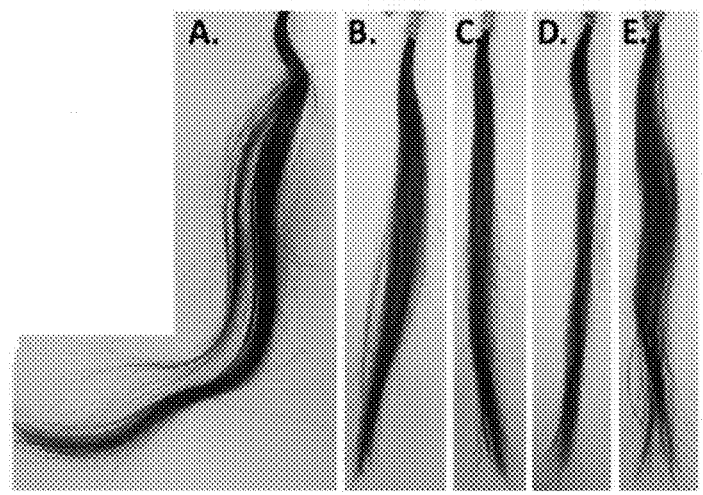
FIG. 20 presents photographic images of a hair sample about 2 months after an exemplary hair straightening treatment, before (FIG. 20A) and several hours after (FIG. 20B) application of 10 mg/ml RES-CBD (resilin with cellulose binding domain) in water, followed by washing (at intervals of 2 days) with water (FIG. 20C), SLS-free shampoo (FIG. 20D), and again with SLS-free shampoo (FIG. 20E).

As shown in FIG. 20, the application of resilin was effective at restoring and maintaining the effect of the previous straightening treatment.

The above results indicate that resilin is effective at restoring and maintaining straightened hair after a wide variety of hair-straightening treatments, and remains effective for at least several months after the hair-straightening treatment.

Example 4

Effect of Cellulose Nanocrystals and of Cellulose Nanocrystals and Resilin on Hair Undergoing Straightening Treatment Hair samples were washed with regular shampoo, fan dried and straightened. 1M cysteine in 100 mM MES pH 3.5 was spread on the hair and left for 15 minutes and thereafter fan-dried. Then, hair samples were washed with water, fan-dried and iron-straightened. Thereafter, 0.5M arginine in 1% BTMS in DDW was spread on the hair and left 15 minutes, the hair was fan-dried and iron-straightened, and then 2% CNC was spread on the hair and left for 30 minutes, and the hair sample was thereafter fan-dried and iron-straightened.

Figure 21C:
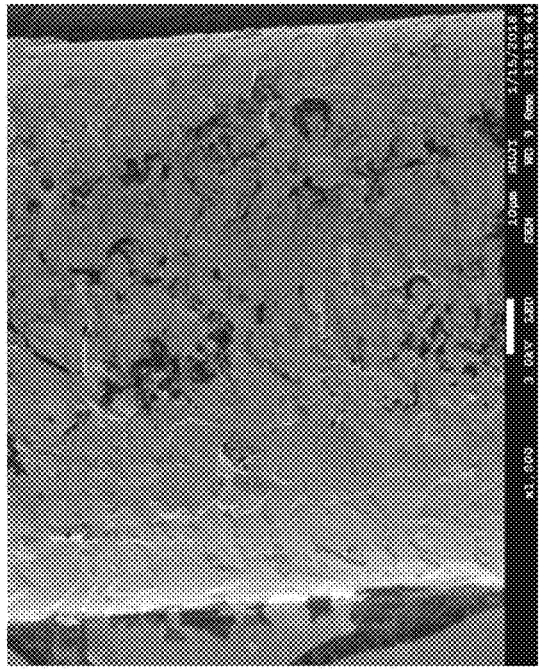
FIGS. 21A-D present scanning electron micrographic images of untreated hair sample at ×1000 magnification (FIG. 21A) and at ×6,500 magnification (FIG. 21B) and of the hair sample following sequential treatment with 1M cysteine in 100 mM MES pH 3.5, 0.5M arginine in 1% BTMS in DDW, and 2% CNC, at ×1000 magnification (FIG. 21C) and at ×6,500 magnification (FIG. 21D).
Figure 21D:
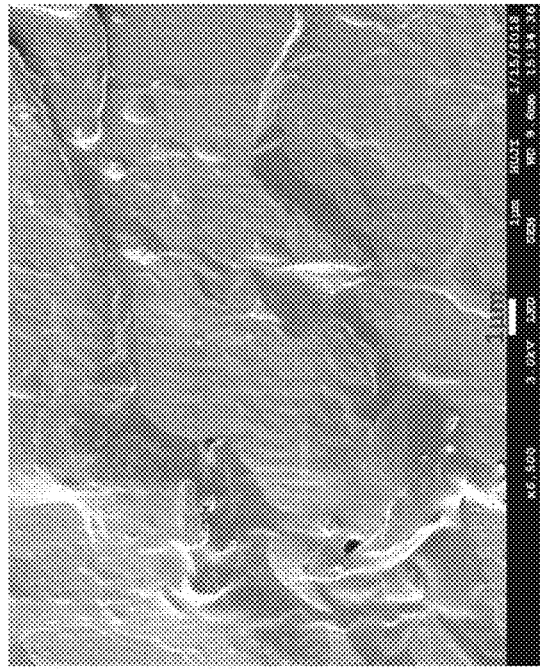
Figure 21A:
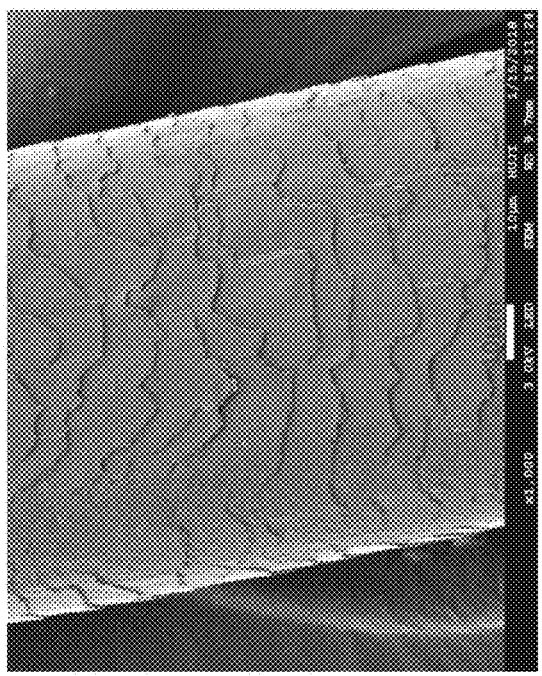
Figure 21B:
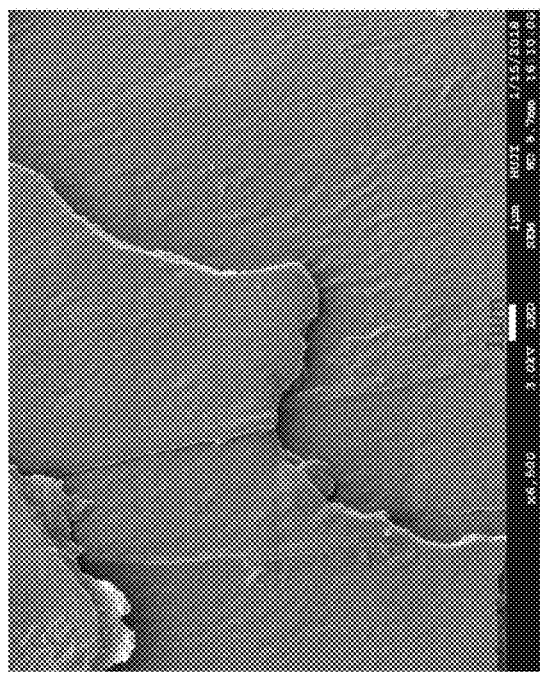

FIGS. 21A-D present SEM images of untreated hair sample, before the above-described treatment (FIGS. 21A and 21B) and of the hair sample following the above-described hair treatment (FIGS. 12C and 21D), with FIGS. 21B and 21D being at higher magnification. As can be seen, in the non-treated hair sample, normal cuticle scales are observed, whereby following treatment, the scales are coated and are hardly observed and are nearly invisible.

In additional experiment, hair samples were washed with regular shampoo, fan-dried and iron-straightened, and a mixture of 1M cysteine in 100 mM MES pH 3.3 and hydro-keratin was spread on the hair, left for 15 minutes and thereafter fan-dried. Then, hair samples were washed with water, fan-dried and iron-straightened, and 0.5M arginine in 1% BTMS was spread on the hair, left in for 15 minutes and thereafter the hair samples were fan-dried. Hair was iron-straightened and 3% CNC was spread on the hair and left for 30 minutes, and thereafter the hair samples were fan-dried and iron-straightened.

Figure 22A:
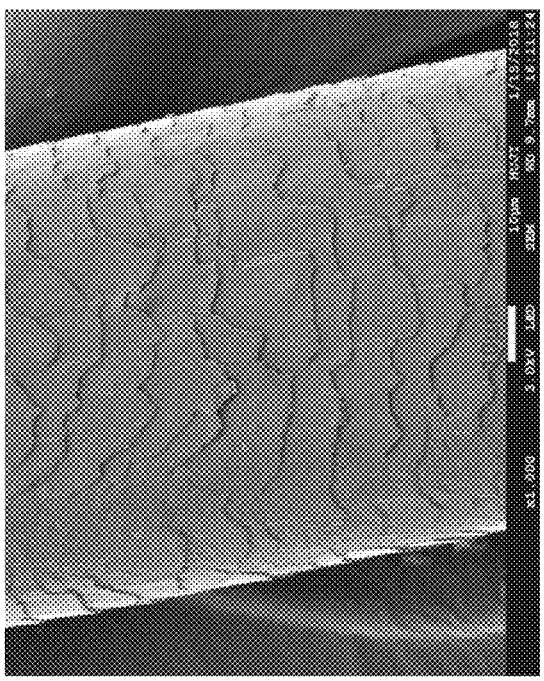
FIGS. 22A-D present scanning electron micrographic images of untreated hair sample at ×1000 magnification (FIG. 22A) and at ×23,000 magnification (FIG. 22B) and of the hair sample following sequential treatment with 1M cysteine in 100 mM MES pH 3.5, 0.5M arginine in 1% BTMS, and 3% CNC, at ×1000 magnification (FIG. 22C) and at ×23,000 magnification (FIG. 22D).
Figure 22B:
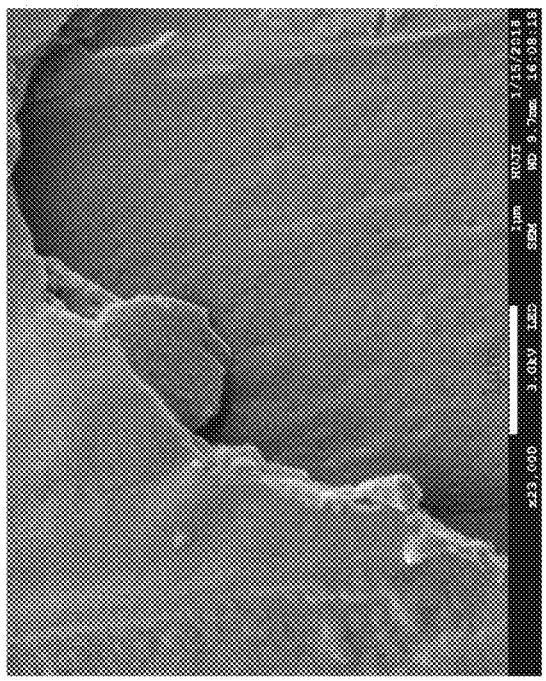
Figure 22C:
Figure 22D:
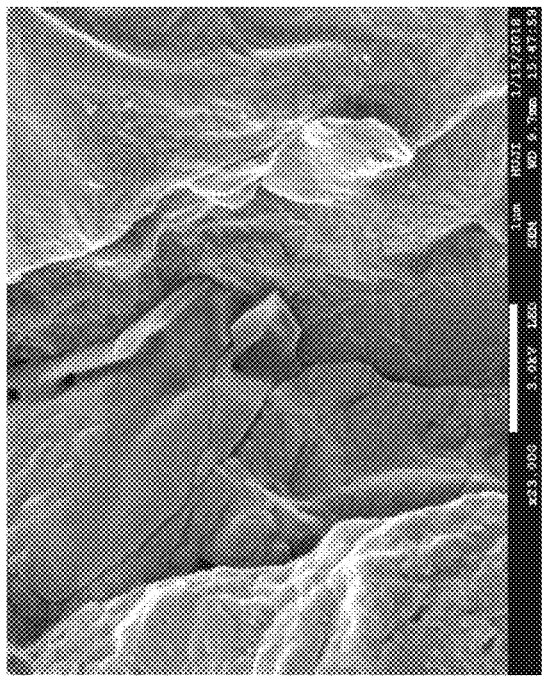

FIGS. 22A-D present SEM images of untreated hair sample, before the above-described treatment (FIGS. 22A and 22B) and of the hair sample following the above-described hair treatment (FIGS. 22C and 22D), with FIGS. 22B and 22D being at higher magnification. As can be seen, in the non-treated hair sample, normal cuticle scales are observed, whereby following treatment, scales are coated and are hardly observed and nearly invisible. In the larger magnification shown in FIG. 22D, the CNC coating on the hair is clearly seen.

In additional experiment, hair samples were washed with regular shampoo, fan-dried and iron-straightened, and thereafter 1M cysteine in 100 mM MES pH 3.5 was spread on the hair, left for 15 minutes and the hair sample was thereafter fan-dried. Then, hair samples were washed with water, fan-dried and iron-straightened, and 0.5M arginine in 1% BTMS in DDW was spread on the hair and left 15 minutes, and the hair was thereafter fan-dried and iron-straightened. 2% CNC containing 10:1 RES-CBD (1 protein to 10 CNC) was then spread on the hair and left for 30 minutes, and the hair was thereafter fan-dried and straightened.

FIGS. 23A-D present SEM images of untreated hair sample, before the above-described treatment (FIGS. 23A and 23B) and of the hair sample following the above-described hair treatment (FIGS. 23C and 23D), with FIGS. 23B and 23D being at higher magnification. As can be seen, in the non-treated hair, normal cuticle scales are observed, whereby following treatment, scales are coated and are hardly observed and nearly invisible. In the larger magnification shown in FIG. 23D, the CNC coating on the hair is clearly seen. In addition, protein clusters on the top of the CNC coating were observed.

Figure 23E:
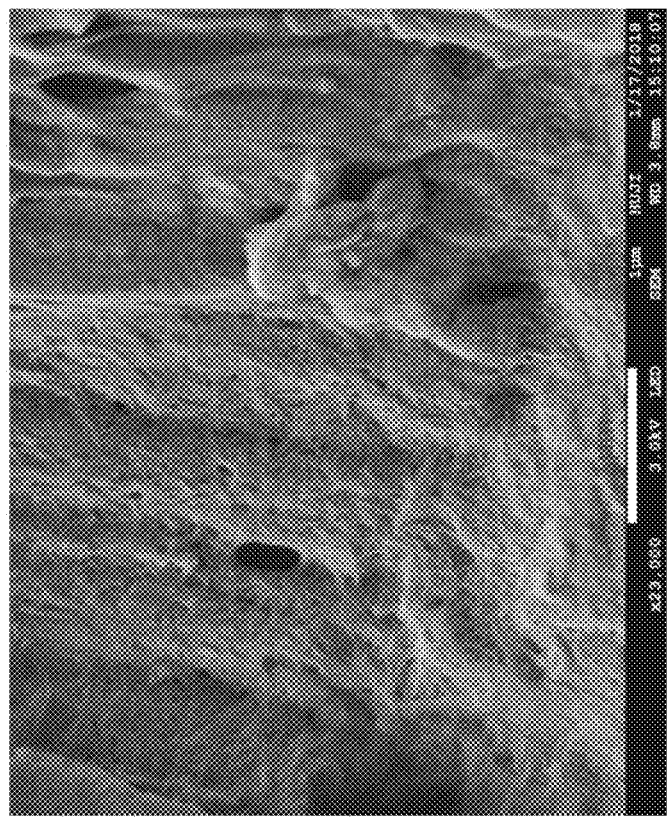

FIG. 23E shows an observation into a gap in the hair coating. The CNC coating on the hair is clearly seen.

These data further demonstrate the effectiveness of the CNC treatment, and moreover of the combined CNC and resilin treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A method of straightening hair, the method comprising:
applying to the hair cysteine, sodium metabisulfite or a combination thereof to thereby obtain cleaved disulfide bonds in the hair;
applying arginine or chitosan to the hair, having cleaved disulfide bonds and heat treating the hair;
subsequently to heat treating the hair, applying to the hair a formulation containing cellulose nanocrystals (CNC) bonded to cellulose binding domain (CBD)-modified resilin in a non-covalent interaction; and
subsequent to applying the formulation containing the CNC, applying heat and pressure to the hair, to cause hair straightening without causing damage to hair, thereby straightening the hair.

2. The method of claim 1, further comprising contacting said hair, having been treated with said formulation containing said CNC bonded to CBD-modified resilin in a non-covalent interaction, with a cross-linking agent capable of cross-linking cellulose nanocrystals.

3. The method of claim 1, comprising applying a further amount of CBD-modified resilin to the hair subsequently to the hair straightening.

4. The method of claim 3, wherein said applying the further amount of CBD-modified resilin is effected at least one day subsequently to the hair straightening.

5. The method of claim 4, wherein said applying the further amount of CBD-modified resilin is effected at least one week after the hair straightening.

6. The method of claim 4, wherein said applying the further amount of CBD-modified resilin is effected during a time period in a range of from one week to two years after hair straightening.

7. The method of claim 3, wherein said applying the further amount of CBD-modified resilin is effected on at least two different days.

8. The method of claim 7, wherein said applying the further amount of CBD-modified resilin is effected on at least 5 different days.

* * * * *

SEQUENCE LISTING

```
<160> NUMBER OF SEQ ID NOS: 21

<210> SEQ ID NO 1
<211> LENGTH: 324
<212> TYPE: PRT
<213> ORGANISM: Artificial sequence
<220> FEATURE:
<223> OTHER INFORMATION: Drosophila melanogaster derived resilin exon 1

<400> SEQUENCE: 1

Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Gly Arg Pro Ser Asp Ser
            20                  25                  30

Tyr Gly Ala Pro Gly Gly Gly Asn Gly Gly Arg Pro Ser Asp Ser Tyr
        35                  40                  45

Gly Ala Pro Gly Gln Gly Gln Gly Gln Gly Gln Gly Gln Gly Gly Tyr
```

```
                    50                  55                  60
Ala Gly Lys Pro Ser Asp Thr Tyr Gly Ala Pro Gly Gly Asn Gly
 65                  70                  75                  80

Asn Gly Gly Arg Pro Ser Ser Tyr Gly Ala Pro Gly Gly Asn
                 85                  90                  95

Gly Gly Arg Pro Ser Asp Thr Tyr Gly Ala Pro Gly Gly Asn Gly
                    100                 105                 110

Gly Arg Pro Ser Asp Thr Tyr Gly Ala Pro Gly Gly Gly Asn Gly
             115                 120                 125

Asn Gly Gly Arg Pro Ser Ser Tyr Gly Ala Pro Gly Gln Gly Gln
 130                 135                 140

Gly Asn Gly Asn Gly Gly Arg Ser Ser Ser Tyr Gly Ala Pro Gly
 145                 150                 155                 160

Gly Gly Asn Gly Gly Arg Pro Ser Asp Thr Tyr Gly Ala Pro Gly
                 165                 170                 175

Gly Asn Gly Gly Arg Pro Ser Asp Thr Tyr Gly Ala Pro Gly Gly
             180                 185                 190

Asn Asn Gly Gly Arg Pro Ser Ser Tyr Gly Ala Pro Gly Gly Gly
 195                 200                 205

Asn Gly Gly Arg Pro Ser Asp Thr Tyr Gly Ala Pro Gly Gly Asn
 210                 215                 220

Gly Asn Gly Ser Gly Gly Arg Pro Ser Ser Tyr Gly Ala Pro Gly
225                 230                 235                 240

Gln Gly Gln Gly Gly Phe Gly Gly Arg Pro Ser Asp Ser Tyr Gly Ala
                 245                 250                 255

Pro Gly Gln Asn Gln Lys Pro Ser Asp Ser Tyr Gly Ala Pro Gly Ser
                 260                 265                 270

Gly Asn Gly Asn Gly Gly Arg Pro Ser Ser Tyr Gly Ala Pro Gly
             275                 280                 285

Ser Gly Pro Gly Gly Arg Pro Ser Asp Ser Tyr Gly Pro Pro Ala Ser
     290                 295                 300

Gly Ser Gly Ala Gly Gly Ala Gly Gly Ser Gly Pro Gly Gly Ala Asp
305                 310                 315                 320

Tyr Asp Asn Asp

<210> SEQ ID NO 2
<211> LENGTH: 323
<212> TYPE: PRT
<213> ORGANISM: Artificial sequence
<220> FEATURE:
<223> OTHER INFORMATION: Drosophila melanogaster derived resilin exon 1

<400> SEQUENCE: 2

Gly Pro Glu Pro Pro Val Asn Ser Tyr Leu Pro Pro Ser Asp Ser Tyr
 1                5                  10                  15

Gly Ala Pro Gly Gln Ser Gly Pro Gly Gly Arg Pro Ser Asp Ser Tyr
                 20                  25                  30

Gly Ala Pro Gly Gly Gly Asn Gly Gly Arg Pro Ser Asp Ser Tyr Gly
             35                  40                  45

Ala Pro Gly Gln Gly Gln Gly Gln Gly Gln Gly Gln Gly Gly Tyr Ala
 50                  55                  60

Gly Lys Pro Ser Asp Thr Tyr Gly Ala Pro Gly Gly Asn Gly Asn
 65                  70                  75                  80

Gly Gly Arg Pro Ser Ser Tyr Gly Ala Pro Gly Gly Asn Gly
                 85                  90                  95
```

-continued

Gly Arg Pro Ser Asp Thr Tyr Gly Ala Pro Gly Gly Asn Gly Gly
            100                 105                 110

Arg Pro Ser Asp Thr Tyr Gly Ala Pro Gly Gly Gly Asn Gly Asn
        115                 120                 125

Gly Gly Arg Pro Ser Ser Tyr Gly Ala Pro Gly Gln Gly Gln Gly
    130                 135                 140

Asn Gly Asn Gly Gly Arg Ser Ser Ser Tyr Gly Ala Pro Gly Gly
145                 150                 155                 160

Gly Asn Gly Gly Arg Pro Ser Asp Thr Tyr Gly Ala Pro Gly Gly
                165                 170                 175

Asn Gly Gly Arg Pro Ser Asp Thr Tyr Gly Ala Pro Gly Gly Asn
            180                 185                 190

Asn Gly Gly Arg Pro Ser Ser Ser Tyr Gly Ala Pro Gly Gly Asn
        195                 200                 205

Gly Gly Arg Pro Ser Asp Thr Tyr Gly Ala Pro Gly Gly Asn Gly
    210                 215                 220

Asn Gly Ser Gly Gly Arg Pro Ser Ser Ser Tyr Gly Ala Pro Gly Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Asn Gly Gly Arg Pro Ser Ser Ser Tyr Gly Ala Pro Gly Ser
        275                 280                 285

Gly Pro Gly Gly Arg Pro Ser Asp Ser Tyr Gly Pro Pro Ala Ser Gly
    290                 295                 300

Ser Gly Ala Gly Gly Ala Gly Gly Ser Gly Pro Gly Gly Ala Asp Tyr
305                 310                 315                 320

Asp Asn Asp

<210> SEQ ID NO 3
<211> LENGTH: 62
<212> TYPE: PRT
<213> ORGANISM: Artificial sequence
<220> FEATURE:
<223> OTHER INFORMATION: Chitin binding sequence

<400> SEQUENCE: 3

Glu Pro Ala Lys Tyr Glu Phe Asn Tyr Gln Val Glu Asp Ala Pro Ser
1               5                   10                  15

Gly Leu Ser Phe Gly His Ser Glu Met Arg Asp Gly Asp Phe Thr Thr
            20                  25                  30

Gly Gln Tyr Asn Val Leu Leu Pro Asp Gly Arg Lys Gln Ile Val Glu
        35                  40                  45

Tyr Glu Ala Asp Gln Gln Gly Tyr Arg Pro Gln Ile Arg Tyr
    50                  55                  60

<210> SEQ ID NO 4
<211> LENGTH: 15
<212> TYPE: PRT
<213> ORGANISM: Artificial sequence
<220> FEATURE:
<223> OTHER INFORMATION: Resilin repeating unit

<400> SEQUENCE: 4

Gly Gly Arg Pro Ser Asp Ser Tyr Gly Ala Pro Gly Gly Gly Asn
1               5                   10                  15

<210> SEQ ID NO 5
<211> LENGTH: 9
<212> TYPE: PRT
<213> ORGANISM: Artificial sequence
<220> FEATURE:
<223> OTHER INFORMATION: Resilin repeating unit

<400> SEQUENCE: 5

Gly Arg Pro Ser Asp Ser Tyr Gly Ala
1               5

<210> SEQ ID NO 6
<211> LENGTH: 74
<212> TYPE: PRT
<213> ORGANISM: Artificial sequence
<220> FEATURE:
<223> OTHER INFORMATION: Chitin binding sequence

<400> SEQUENCE: 6

Pro Ala Lys Tyr Glu Phe Asn Tyr Gln Val Glu Asp Ala Pro Ser Gly
1               5                   10                  15

Leu Ser Phe Gly His Ser Glu Met Arg Asp Gly Asp Phe Thr Thr Gly
            20                  25                  30

Gln Tyr Asn Val Leu Leu Pro Asp Gly Arg Lys Gln Ile Val Glu Tyr
        35                  40                  45

Glu Ala Asp Gln Gln Gly Tyr Arg Pro Gln Ile Arg Tyr Glu Gly Asp
    50                  55                  60

Ala Asn Asp Gly Ser Gly Pro Ser Gly Pro
65                  70

<210> SEQ ID NO 7
<211> LENGTH: 900
<212> TYPE: DNA
<213> ORGANISM: Artificial sequence
<220> FEATURE:
<223> OTHER INFORMATION: Examples of polynucleotides which can be used
      to express resilin

<400> SEQUENCE: 7
agctatggag caccgggtca gagtggtccc ggcggcaggc cgtcggattc ctatggagct      60
cctggtggtg aaacggtgg acggccctca gacagctatg cgctccagg ccagggtcaa      120 ggacagggac aaggacaagg tggatatgca ggcaagccct cagatacgta tggagctcct     180
ggtggtggaa atggcaacgg aggtcgtcca tcgagcagct atggcgctcc tggcggtgga    240
aacggtggtc gtccttcgga tacctacggt gctcctggtg gcggaaatgg tggacgccca    300
tcggacactt atggtgctcc tggtggtggt ggaaatggca acggcggacg accttcaagc    360
agctatggag ctcctggtca aggacaaggc aacggaaatg gcggtcgctc atcgagcagc    420
tatggtgctc ctggcggtgg aaacggcggt cgtccttcgg ataccctacgg tgctcccggt    480 ggtggaaacg tggtcgtcc ttcggatact acggcgctc ctggtggcgg caataatggc      540
ggtcgtccct caagcagcta cggcgctcct ggtggtggaa acggtggtcg tccatctgac    600
acctatggcg ctcctggtgg cggtaacgga acggcagcg tggtcgtcc ttcaagcagc      660 tatggagctc ctggtcaggg ccaaggtgga tttggtggtc gtccatcgga ctcctatggt    720
gctcctggtc agaaccaaaa accatcagat tcatatggcg ccctggtag cggcaatggc    780 aacggcggac gtccttcgag cagctatgga gctccaggct caggacctgg tggccgaccc    840
tccgactcct acggacccc agcttctgga tcgggagcag gtggcgctgg aggcagtgga    900

<210> SEQ ID NO 8
<211> LENGTH: 1080
<212> TYPE: DNA
<213> ORGANISM: Artificial sequence
<220> FEATURE:
<223> OTHER INFORMATION: An exemplary DNA sequence of 6H-tagged resilin
(exon 1)

<400> SEQUENCE: 8

```
atgtcgtact accatcacca tcaccatcac gattacgata tcccaacgac cgaaaacctg      60
tattttcagg gcgccatggg accggagcca ccagttaact cgtatctacc tccgtccgat     120
agctatggag caccgggtca gagtggtccc ggcggcaggc cgtcggattc ctatggagct     180
cctggtggtg gaaacggtgg acggccctca gacagctatg gcgctccagg ccagggtcaa     240
ggacagggac aaggacaagg tggatatgca ggcaagccct cagataccta tggagctcct     300
ggtggtggaa atggcaacgg aggtcgtcca tcgagcagct atggcgctcc tggcggtgga     360
aacggtggtc gtccttcgga tacctacggt gctcctggtg gcgaaatgg tggacgccca      420
tcggacactt atggtgctcc tggtggtggt ggaaatggca acggcggacg accttcaagc     480
agctatggag ctcctggtca aggacaaggc aacggaaatg gcggtcgctc atcgagcagc     540
tatggtgctc ctggcggtgg aaacggcggt cgtccttcgg ataccacgg tgctcccggt      600
ggtggaaacg gtggtcgtcc ttcggatact tacggcgctc ctggtggcgg caataatggc     660
ggtcgtccct caagcagcta cggcgctcct ggtggtggaa acggtggtcg tccatctgac     720
acctatggcg ctcctggtgg cggtaacgga acggcagcg tggtcgtcc ttcaagcagc       780
tatggagctc ctggtcaggg ccaaggtgga tttggtggtc gtccatcgga ctcctatggt     840
gctcctggta gaaccaaaaa accatcagat tcatatggcg cccctggtag cggcaatggc     900
aacggcggac gtccttcgag cagctatgga gctccaggct caggacctgg tggccgaccc     960
tccgactcct acggacccc agcttctgga tcggagcag gtggcgctgg aggcagtgga     1020
cccggcggcg ctgactacga taacgatgag ggatccaatc actagtgaat tcgcggccgc    1080
```

<210> SEQ ID NO 9
<211> LENGTH: 354
<212> TYPE: PRT
<213> ORGANISM: Artificial sequence
<220> FEATURE:
<223> OTHER INFORMATION: An exemplary [protein sequence of 6H-tagged
resilin (exon 1)

<400> SEQUENCE: 9

```
Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
            85                  90                  95

Tyr Gly Ala Pro Gly Gly Gly Asn Gly Asn Gly Gly Arg Pro Ser Ser
            100                 105                 110
```

Ser Tyr Gly Ala Pro Gly Gly Asn Gly Gly Arg Pro Ser Asp Thr
            115                 120                 125

Tyr Gly Ala Pro Gly Gly Asn Gly Gly Arg Pro Ser Asp Thr Tyr
        130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Arg
            165                 170                 175

Ser Ser Ser Ser Tyr Gly Ala Pro Gly Gly Asn Gly Gly Arg Pro
        180                 185                 190

Ser Asp Thr Tyr Gly Ala Pro Gly Gly Gly Asn Gly Gly Arg Pro Ser
            195                 200                 205

Asp Thr Tyr Gly Ala Pro Gly Gly Gly Asn Asn Gly Gly Arg Pro Ser
        210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
            245                 250                 255

Pro Ser Ser Ser Tyr Gly Ala Pro Gly Gln Gly Gln Gly Gly Phe Gly
        260                 265                 270

Gly Arg Pro Ser Asp Ser Tyr Gly Ala Pro Gly Gln Asn Gln Lys Pro
    275                 280                 285

Ser Asp Ser Tyr Gly Ala Pro Gly Ser Gly Asn Gly Asn Gly Arg
        290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Gly Ser
        340                 345                 350

Asn His

<210> SEQ ID NO 10
<211> LENGTH: 1311
<212> TYPE: DNA
<213> ORGANISM: Artificial sequence
<220> FEATURE:
<223> OTHER INFORMATION: An exemplary DNA sequence of 6H-tagged resilin
      (exons 1 and 2)

<400> SEQUENCE: 10
catatgtcgt actaccatca ccatcaccat cacgattacg atatcccaac gaccgaaaac      60
ctgtattttc agggcgccat gggaccggag ccaccagtta actcgtatct acctccgtcc     120
gatagctatg agcaccgggt cagagtggt cccggcggca ggccgtcgga ttcctatgga     180
gctcctggtg gtggaaacgg tggacggccc tcagacagct atggcgctcc aggccagggt     240
caaggacagg gacaaggaca aggtggatat gcaggcaagc cctcagatac ctatggagct     300
cctggtggtg gaaatggcaa cggaggtcgt ccatcgagca gctatggcgc tcctggcggt     360
ggaaacggtg gtcgtccttc ggatacctac ggtgctcctg gtggcggaaa tggtggacgc     420
ccatcggaca cttatggtgc tcctggtggt ggtggaaatg gcaacggcgg acgaccttca     480
agcagctatg agctcctgg tcaaggacaa ggcaacggaa atggcggtcg ctcatcgagc     540
agctatggtg ctcctggcgg tggaaacggc ggtcgtcctt cggatacctc cggtgctccc     600

```
ggtggtggaa acggtggtcg tccttcggat acttacggcg ctcctggtgg cggcaataat    660
ggcggtcgtc cctcaagcag ctacggcgct cctggtggtg aaacggtgg tcgtccatct    720 gacacctatg gcgctcctgg tggcggtaac ggaaacggca gcggtggtcg tccttcaagc    780
agctatggag ctcctggtca gggccaaggt ggatttggtg tcgtccatc ggactcctat    840 ggtgctcctg gtcagaacca aaaaccatca gattcatatg gcgcccctgg tagcggcaat    900
ggcaacggcg gacgtccttc gagcagctat ggagctccag gctcaggacc tggtggccga    960
ccctccgact cctacggacc cccagcttct ggatcgggag caggtggcgc tggaggcagt   1020
ggacccggcg cgctgactac gataacgat gagcccgcca agtacgaatt taattaccag   1080
gttgaggacg cgcccagcgg actctcgttc gggcattcag agatgcgcga cggtgacttc   1140
accaccggcc agtacaatgt cctgttgccc gacggaagga agcaaattgt ggagtatgaa   1200
gccgaccagc agggctaccg gccacagatc cgctacgaag gcgatgccaa cgatggcagt   1260
ggtcccagcg gtccttaagg atccgagctc cgtcgacaag cttgcggccg c             1311
```

<210> SEQ ID NO 11
<211> LENGTH: 424
<212> TYPE: PRT
<213> ORGANISM: Artificial sequence
<220> FEATURE:
<223> OTHER INFORMATION: An exemplary protein sequence of 6H-tagged
      resilin (exons 1 and 2)

<400> SEQUENCE: 11

```
Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
            85                  90                  95

Tyr Gly Ala Pro Gly Gly Gly Asn Gly Asn Gly Arg Pro Ser Ser
            100                 105                 110

Ser Tyr Gly Ala Pro Gly Gly Gly Asn Gly Gly Arg Pro Ser Asp Thr
        115                 120                 125

Tyr Gly Ala Pro Gly Gly Gly Asn Gly Gly Arg Pro Ser Asp Thr Tyr
    130                 135                 140

Gly Ala Pro Gly Gly Gly Asn Gly Asn Gly Arg Pro Ser Ser
145                 150                 155                 160

Ser Tyr Gly Ala Pro Gly Gln Gly Gln Gly Asn Gly Asn Gly Arg
            165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
        195                 200                 205

Asp Thr Tyr Gly Ala Pro Gly Gly Gly Asn Asn Gly Gly Arg Pro Ser
    210                 215                 220

Ser Ser Tyr Gly Ala Pro Gly Gly Gly Asn Gly Gly Arg Pro Ser Asp
225                 230                 235                 240
```

Thr Tyr Gly Ala Pro Gly Gly Asn Gly Asn Gly Ser Gly Gly Arg
            245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
            275                 280                 285

Ser Asp Ser Tyr Gly Ala Pro Gly Ser Gly Asn Gly Asn Gly Gly Arg
        290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Pro Ala
            340                 345                 350

Lys Tyr Glu Phe Asn Tyr Gln Val Glu Asp Ala Pro Ser Gly Leu Ser
            355                 360                 365

Phe Gly His Ser Glu Met Arg Asp Gly Asp Phe Thr Thr Gly Gln Tyr
        370                 375                 380

Asn Val Leu Leu Pro Asp Gly Arg Lys Gln Ile Val Glu Tyr Glu Ala
385                 390                 395                 400

Asp Gln Gln Gly Tyr Arg Pro Gln Ile Arg Tyr Glu Gly Asp Ala Asn
            405                 410                 415

Asp Gly Ser Gly Pro Ser Gly Pro
            420

<210> SEQ ID NO 12
<211> LENGTH: 1580
<212> TYPE: DNA
<213> ORGANISM: Artificial sequence
<220> FEATURE:
<223> OTHER INFORMATION: An exemplary DNA sequence of 6H-tagged resilin
      (exon 1) fused to a cellulose-binding domain (CBD)

<400> SEQUENCE: 12
catatgtcgt actaccatca ccatcaccat cacgattacg atatcccaac gaccgaaaac    60
ctgtattttc agggcgccat gggaccggag ccaccagtta actcgtatct acctccgtcc   120
gatagctatg gagcaccggg tcagagtggt cccggcggca ggccgtcgga ttcctatgga   180
gctcctggtg gtggaaacgg tggacggccc tcagacagct atggcgctcc aggccagggt   240
caaggacagg gacaaggaca aggtggatat gcaggcaagc cctcagatac ctatggagct   300
cctggtggtg gaaatggcaa cggaggtcgt ccatcgagca gctatggcgc tcctggcggt   360
ggaaacggtg gtcgtccttc ggatacctac ggtgctcctg gtgcggaaa tggtggacgc    420 ccatcggaca cttatggtgc tcctggtggt ggtggaaatg gcaacggcgg acgaccttca   480
agcagctatg gagctcctgg tcaaggacaa ggcaacggaa atggcggtcg ctcatcgagc   540
agctatggtg ctcctggcgg tggaaacggc ggtcgtcctt cggatacctc ggtgctccc    600 ggtggtggaa acggtggtcg tccttcggat acttacggcg ctcctggtgg cggcaataat   660
ggcggtcgtc cctcaagcag ctacggcgct cctggtggtg aaacggtgg tcgtccatct    720 gacacctatg gcgctcctgg tggcggtaac ggaaacggca gcggtggtcg tccttcaagc   780
agctatggag ctcctggtca gggccaaggt ggatttggtg gtcgtccatc ggactcctat   840
ggtgctcctg gtcagaacca aaaaccatca gattcatatg gcgcccctgg tagcggcaat   900
ggcaacggcg gacgtccttc gagcagctat ggagctccag gctcaggacc tggtggccga   960

```
ccctccgact cctacggacc cccagcttct ggatcgggag caggtggcgc tggaggcagt    1020
ggacccggcg gcgctgacta cgataacgat gagggggatcc ccgaccccgg catggcagcg   1080
acatcatcaa tgtcagttga attttacaac tctaacaaat cagcacaaac aaactcaatt    1140
acaccaataa tcaaaattac taacacatct gacagtgatt taaatttaaa tgacgtaaaa    1200
gttagatatt attacacaag tgatggtaca caaggacaaa ctttctggtg tgaccatgct    1260
ggtgcattat taggaaatag ctatgttgat aacactagca aagtgacagc aaacttcgtt    1320
aaagaaacag caagcccaac atcaacctat gatacatatg ttgaatttgg atttgcaagc    1380
ggacgagcta ctcttaaaaa aggacaattt ataactattc aaggaagaat aacaaaatca    1440
gactggtcaa actacactca aacaaatgac tattcatttg atgcaagtag ttcaacacca    1500
gttgtaaatc caaagttac aggatatata ggtggagcta agtacttgg tacagcacca     1560 taggatcgat ccagatgtac                                                1580
```

<210> SEQ ID NO 13
<211> LENGTH: 519
<212> TYPE: PRT
<213> ORGANISM: Artificial sequence
<220> FEATURE:
<223> OTHER INFORMATION: An exemplary protein sequence of 6H-tagged
      resilin (exon 1) fused to a cellulose-binding domain (CBD)

<400> SEQUENCE: 13

```
Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
                85                  90                  95

Tyr Gly Ala Pro Gly Gly Gly Asn Gly Asn Gly Gly Arg Pro Ser Ser
            100                 105                 110

Ser Tyr Gly Ala Pro Gly Gly Gly Asn Gly Gly Arg Pro Ser Asp Thr
        115                 120                 125

Tyr Gly Ala Pro Gly Gly Gly Asn Gly Gly Arg Pro Ser Asp Thr Tyr
    130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Gly Arg
            165                 170                 175

Ser Ser Ser Ser Tyr Gly Ala Pro Gly Gly Asn Gly Gly Arg Pro
        180                 185                 190

Ser Asp Thr Tyr Gly Ala Pro Gly Gly Gly Asn Gly Gly Arg Pro Ser
    195                 200                 205

Asp Thr Tyr Gly Ala Pro Gly Gly Asn Asn Gly Gly Arg Pro Ser
    210                 215                 220

Ser Ser Tyr Gly Ala Pro Gly Gly Gly Asn Gly Gly Arg Pro Ser Asp
225                 230                 235                 240
```

```
Thr Tyr Gly Ala Pro Gly Gly Gly Asn Gly Asn Gly Ser Gly Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
        275                 280                 285

Ser Asp Ser Tyr Gly Ala Pro Gly Ser Gly Asn Gly Asn Gly Gly Arg
    290                 295                 300

Pro Ser Ser Ser Tyr Gly Ala Pro Gly Ser Pro Gly Gly Arg Pro
305                 310                 315                 320

Ser Asp Ser Tyr Gly Pro Pro Ala Ser Gly Ser Gly Ala Gly Gly Ala
                325                 330                 335

Gly Gly Ser Gly Pro Gly Gly Ala Asp Tyr Asp Asn Asp Glu Gly Ile
            340                 345                 350

Pro Asp Pro Gly Met Ala Ala Thr Ser Ser Met Ser Val Glu Phe Tyr
        355                 360                 365

Asn Ser Asn Lys Ser Ala Gln Thr Asn Ser Ile Thr Pro Ile Ile Lys
    370                 375                 380

Ile Thr Asn Thr Ser Asp Ser Asp Leu Asn Leu Asn Asp Val Lys Val
385                 390                 395                 400

Arg Tyr Tyr Tyr Thr Ser Asp Gly Thr Gln Gly Gln Thr Phe Trp Cys
                405                 410                 415

Asp His Ala Gly Ala Leu Leu Gly Asn Ser Tyr Val Asp Asn Thr Ser
            420                 425                 430

Lys Val Thr Ala Asn Phe Val Lys Glu Thr Ala Ser Pro Thr Ser Thr
        435                 440                 445

Tyr Asp Thr Tyr Val Glu Phe Gly Phe Ala Ser Gly Arg Ala Thr Leu
    450                 455                 460

Lys Lys Gly Gln Phe Ile Thr Ile Gln Gly Arg Ile Thr Lys Ser Asp
465                 470                 475                 480

Trp Ser Asn Tyr Thr Gln Thr Asn Asp Tyr Ser Phe Asp Ala Ser Ser
                485                 490                 495

Ser Thr Pro Val Val Asn Pro Lys Val Thr Gly Tyr Ile Gly Gly Ala
            500                 505                 510

Lys Val Leu Gly Thr Ala Pro
        515

<210> SEQ ID NO 14
<211> LENGTH: 1620
<212> TYPE: DNA
<213> ORGANISM: Artificial sequence
<220> FEATURE:
<223> OTHER INFORMATION: An exemplary DNA sequence of 6H-tagged resilin
      (exon 1) fused to a cellulose-binding domain (CBD)

<400> SEQUENCE: 14
catatgtcgt actaccatca ccatcaccat cacgattacg atatcccaac gaccgaaaac      60
ctgtattttc agggcgccat ggcagcgaca tcatcaatgt cagttgaatt ttacaactct     120
aacaaagcag cacaaacaaa ctcaattaca ccaataatca aaattactaa cacagctgac     180
agtgatttaa atttaaatga cgtaaaagtt agatattatt acacaagtga tggtacacaa     240
ggacaaactt tctggggtga tcatgctggt gcattattag gaaatagcta tgttgataac     300
actggcaaag tgacagcaaa cttcgttaaa gaaacagcaa gcccaacatc aacctatgat     360
acatatgttg aatttggatt tgcaagcgga gcagctactc ttaaaaaagg acaatttata     420
```

```
actattcaag gaagaataac aaaatcagac tggtcaaact acgctcagac aaatgactat    480
tcatttgatg caagtagttc aacaccagtt gtaaatccaa aagttacagg atatataggt    540
ggagctaaag tacttggtac agcaccaggt ccagatgtac catcttcaat aattaatcct    600
acttctgcaa catttgatcc ggagccacca gttaactcgt atctacctcc gtccgatagc    660
tatggagcac cgggtcagag tggtcccggc ggcaggccgt cggattccta tggagctcct    720
ggtggtggaa acggtggacg gccctcagac agctatggcg ctccaggcca gggtcaagga    780
cagggacaag gacaaggtgg atatgcaggc aagccctcag atacctatgg agctcctggt    840 ggtgaaatg gcaacggagg tcgtccatcg agcagctatg gcgctcctgg cggtggaaac    900
ggtggtcgtc cttcggatac ctacggtgct cctggtggcg gaaatggtgg acgcccatcg    960
gacacttatg gtgctcctgg tggtggtgga aatggcaacg gcggacgacc ttcaagcagc    1020
tatggagctc ctggtcaagg acaaggcaac ggaaatggcg gtcgctcatc gagcagctat    1080
ggtgctcctg gcggtggaaa cggcggtcgt ccttcggata cctacggtgc tcccggtggt    1140
ggaaacggtg gtcgtccttc ggatacttac ggcgctcctg gtggcggcaa taatggcggt    1200
cgtccctcaa gcagctacgg cgctcctggt ggtggaaacg gtggtcgtcc atctgacacc    1260
tatggcgctc ctggtggcgg taacggaaac ggcagcggtg gtcgtccttc aagcagctat    1320
ggagctcctg gtcagggcca aggtggattt ggtggtcgtc atcggactc ctatggtgct    1380 cctggtcaga accaaaaacc atcagattca tatgcgcccc tggtagcgg caatggcaac    1440 ggcggacgtc cttcgagcag ctatggagct ccaggctcag acctggtgg ccgaccctcc    1500 gactcctacg accccccagc ttctggatcg ggagcaggtg cgctggagg cagtggaccc    1560 ggcggcgctg actacgataa cgatgagtaa ggatccgagc tccgtcgaca agcttgcggc    1620
```

<210> SEQ ID NO 15
<211> LENGTH: 528
<212> TYPE: PRT
<213> ORGANISM: Artificial sequence
<220> FEATURE:
<223> OTHER INFORMATION: An exemplary protein sequence of 6H-tagged resilin (exon 1) fused to a cellulose-binding domain (CBD)

<400> SEQUENCE: 15

```
Met Ser Tyr Tyr His His His His His His Asp Tyr Asp Ile Pro Thr
1               5                   10                  15

Thr Glu Asn Leu Tyr Phe Gln Gly Ala Met Ala Ala Thr Ser Ser Met
            20                  25                  30

Ser Val Glu Phe Tyr Asn Ser Asn Lys Ala Ala Gln Thr Asn Ser Ile
        35                  40                  45

Thr Pro Ile Ile Lys Ile Thr Asn Thr Ala Asp Ser Asp Leu Asn Leu
    50                  55                  60

Asn Asp Val Lys Val Arg Tyr Tyr Tyr Thr Ser Asp Gly Thr Gln Gly
65                  70                  75                  80

Gln Thr Phe Trp Gly Asp His Ala Gly Ala Leu Leu Gly Asn Ser Tyr
                85                  90                  95

Val Asp Asn Thr Gly Lys Val Thr Ala Asn Phe Val Lys Glu Thr Ala
            100                 105                 110

Ser Pro Thr Ser Thr Tyr Asp Tyr Val Glu Phe Gly Phe Ala Ser
        115                 120                 125

Gly Ala Ala Thr Leu Lys Lys Gly Gln Phe Ile Thr Ile Gln Gly Arg
    130                 135                 140

Ile Thr Lys Ser Asp Trp Ser Asn Tyr Ala Gln Thr Asn Asp Tyr Ser
```

```
            145                 150                 155                 160
        Phe Asp Ala Ser Ser Ser Thr Pro Val Val Asn Pro Lys Val Thr Gly
                        165                 170                 175

Tyr Ile Gly Gly Ala Lys Val Leu Gly Thr Ala Pro Gly Pro Asp Val
                        180                 185                 190

Pro Ser Ser Ile Ile Asn Pro Thr Ser Ala Thr Phe Asp Pro Glu Pro
                        195                 200                 205

Pro Val Asn Ser Tyr Leu Pro Pro Ser Asp Ser Tyr Gly Ala Pro Gly
            210                 215                 220

Gln Ser Gly Pro Gly Gly Arg Pro Ser Asp Ser Tyr Gly Ala Pro Gly
        225                 230                 235                 240

Gly Gly Asn Gly Gly Arg Pro Ser Asp Ser Tyr Gly Ala Pro Gly Gln
                        245                 250                 255

Gly Gln Gly Gln Gly Gln Gly Gln Gly Gly Tyr Ala Gly Lys Pro Ser
                        260                 265                 270

Asp Thr Tyr Gly Ala Pro Gly Gly Gly Asn Gly Asn Gly Gly Arg Pro
                        275                 280                 285

Ser Ser Ser Tyr Gly Ala Pro Gly Gly Gly Asn Gly Gly Arg Pro Ser
            290                 295                 300

Asp Thr Tyr Gly Ala Pro Gly Gly Gly Asn Gly Gly Arg Pro Ser Asp
        305                 310                 315                 320

Thr Tyr Gly Ala Pro Gly Gly Gly Asn Gly Asn Gly Gly Arg Pro
                        325                 330                 335

Ser Ser Ser Tyr Gly Ala Pro Gly Gln Gly Gln Gly Asn Gly Asn Gly
                        340                 345                 350

Gly Arg Ser Ser Ser Tyr Gly Ala Pro Gly Gly Asn Gly Gly
                    355                 360                 365

Arg Pro Ser Asp Thr Tyr Gly Ala Pro Gly Gly Asn Gly Gly Arg
                    370                 375                 380

Pro Ser Asp Thr Tyr Gly Ala Pro Gly Gly Gly Asn Asn Gly Gly Arg
        385                 390                 395                 400

Pro Ser Ser Ser Tyr Gly Ala Pro Gly Gly Gly Asn Gly Gly Arg Pro
                        405                 410                 415

Ser Asp Thr Tyr Gly Ala Pro Gly Gly Gly Asn Gly Asn Gly Ser Gly
                        420                 425                 430

Gly Arg Pro Ser Ser Tyr Gly Ala Pro Gly Gln Gly Gln Gly Gly
                    435                 440                 445

Phe Gly Gly Arg Pro Ser Asp Ser Tyr Gly Ala Pro Gly Gln Asn Gln
            450                 455                 460

Lys Pro Ser Asp Ser Tyr Gly Ala Pro Gly Ser Gly Asn Gly Asn Gly
        465                 470                 475                 480

Gly Arg Pro Ser Ser Tyr Gly Ala Pro Gly Ser Gly Pro Gly Gly
                    485                 490                 495

Arg Pro Ser Asp Ser Tyr Gly Pro Pro Ala Ser Gly Ser Gly Ala Gly
                    500                 505                 510

Gly Ala Gly Gly Ser Gly Pro Gly Gly Ala Asp Tyr Asp Asn Asp Glu
                    515                 520                 525

<210> SEQ ID NO 16
<211> LENGTH: 324
<212> TYPE: PRT
<213> ORGANISM: Artificial sequence
<220> FEATURE:
<223> OTHER INFORMATION: Resilin exon 1
```

<400> SEQUENCE: 16

Gly Pro Glu Pro Pro Val Asn Ser Tyr Leu Pro Pro Ser Asp Ser Tyr
1               5                   10                  15

Gly Ala Pro Gly Gln Ser Gly Pro Gly Gly Arg Pro Ser Asp Ser Tyr
            20                  25                  30

Gly Ala Pro Gly Gly Gly Asn Gly Gly Arg Pro Ser Asp Ser Tyr Gly
        35                  40                  45

Ala Pro Gly Gln Gly Gln Gly Gln Gly Gln Gly Gln Gly Gly Tyr Ala
    50                  55                  60

Gly Lys Pro Ser Asp Thr Tyr Gly Ala Pro Gly Gly Gly Asn Gly Asn
65                  70                  75                  80

Gly Gly Arg Pro Ser Ser Ser Tyr Gly Ala Pro Gly Gly Gly Asn Gly
                85                  90                  95

Gly Arg Pro Ser Asp Thr Tyr Gly Ala Pro Gly Gly Gly Asn Gly Gly
            100                 105                 110

Arg Pro Ser Asp Thr Tyr Gly Ala Pro Gly Gly Gly Asn Gly Asn
        115                 120                 125

Gly Gly Arg Pro Ser Ser Ser Tyr Gly Ala Pro Gly Gln Gly Gln Gly
    130                 135                 140

Asn Gly Asn Gly Gly Arg Ser Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
                165                 170                 175

Asn Gly Gly Arg Pro Ser Asp Thr Tyr Gly Ala Pro Gly Gly Gly Asn
            180                 185                 190

Asn Gly Gly Arg Pro Ser Ser Ser Tyr Gly Ala Pro Gly Gly Gly Asn
        195                 200                 205

Gly Gly Arg Pro Ser Asp Thr Tyr Gly Ala Pro Gly Gly Gly Asn Gly
    210                 215                 220

Asn Gly Ser Gly Gly Arg Pro Ser Ser Ser Tyr Gly Ala Pro Gly Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Asn Gly Gly Arg Pro Ser Ser Ser Tyr Gly Ala Pro Gly Ser
        275                 280                 285

Gly Pro Gly Gly Arg Pro Ser Asp Ser Tyr Gly Pro Pro Ala Ser Gly
    290                 295                 300

Ser Gly Ala Gly Gly Ala Gly Gly Ser Gly Pro Gly Gly Ala Asp Tyr
305                 310                 315                 320

Asp Asn Asp Glu

<210> SEQ ID NO 17
<211> LENGTH: 180
<212> TYPE: PRT
<213> ORGANISM: Artificial sequence
<220> FEATURE:
<223> OTHER INFORMATION: Cellulose binding domain protein sequence

<400> SEQUENCE: 17

Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
            20                  25                  30

-continued

```
Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
     50                  55                  60

Ala Leu Leu Gly Asn Ser Tyr Val Asp Asn Thr Gly Lys Val Thr Ala
 65                  70                  75                  80

Asn Phe Val Lys Glu Thr Ala Ser Pro Thr Thr Tyr Asp Thr Tyr
                 85                  90                  95

Val Glu Phe Gly Phe Ala Ser Gly Ala Ala Thr Leu Lys Lys Gly Gln
                100                 105                 110

Phe Ile Thr Ile Gln Gly Arg Ile Thr Lys Ser Asp Trp Ser Asn Tyr
            115                 120                 125

Ala Gln Thr Asn Asp Tyr Ser Phe Asp Ala Ser Ser Thr Pro Val
        130                 135                 140

Val Asn Pro Lys Val Thr Gly Tyr Ile Gly Gly Ala Lys Val Leu Gly
145                 150                 155                 160

Thr Ala Pro Gly Pro Asp Val Pro Ser Ser Ile Ile Asn Pro Thr Ser
                165                 170                 175

Ala Thr Phe Asp
            180
```

<210> SEQ ID NO 18
<211> LENGTH: 163
<212> TYPE: PRT
<213> ORGANISM: Artificial sequence
<220> FEATURE:
<223> OTHER INFORMATION: Cellulose binding domain protein sequence

<400> SEQUENCE: 18

```
Met Ala Ala Thr Ser Ser Met Ser Val Glu Phe Tyr Asn Ser Asn Lys
 1               5                  10                  15

Ala Ala Gln Thr Asn Ser Ile Thr Pro Ile Ile Lys Ile Thr Asn Thr
                 20                  25                  30

Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
     50                  55                  60

Ala Leu Leu Gly Asn Ser Tyr Val Asp Asn Thr Gly Lys Val Thr Ala
 65                  70                  75                  80

Asn Phe Val Lys Glu Thr Ala Ser Pro Thr Thr Tyr Asp Thr Tyr
                 85                  90                  95

Val Glu Phe Gly Phe Ala Ser Gly Ala Ala Thr Leu Lys Lys Gly Gln
                100                 105                 110

Phe Ile Thr Ile Gln Gly Arg Ile Thr Lys Ser Asp Trp Ser Asn Tyr
            115                 120                 125

Ala Gln Thr Asn Asp Tyr Ser Phe Asp Ala Ser Ser Thr Pro Val
        130                 135                 140

Val Asn Pro Lys Val Thr Gly Tyr Ile Gly Gly Ala Lys Val Leu Gly
145                 150                 155                 160

Thr Ala Pro
```

<210> SEQ ID NO 19
<211> LENGTH: 605
<212> TYPE: PRT
<213> ORGANISM: Drosophila melanogaster

<400> SEQUENCE: 19

```
Met Val Arg Pro Glu Pro Val Asn Ser Tyr Leu Pro Pro Ser Asp
1               5                   10                  15

Ser Tyr Gly Ala Pro Gly Gln Ser Gly Pro Gly Gly Arg Pro Ser Asp
            20                  25                  30

Ser Tyr Gly Ala Pro Gly Gly Asn Gly Gly Arg Pro Ser Asp Ser
            35                  40                  45

Tyr Gly Ala Pro Gly Gln Gly Gln Gly Gln Gly Gln Gly Gly
    50                  55                  60

Tyr Ala Gly Lys Pro Ser Asp Thr Tyr Gly Ala Pro Gly Gly Asn
65                  70                  75                  80

Gly Asn Gly Gly Arg Pro Ser Ser Tyr Gly Ala Pro Gly Gly
                85                  90                  95

Asn Gly Gly Arg Pro Ser Asp Thr Tyr Gly Ala Pro Gly Gly Asn
            100                 105                 110

Gly Gly Arg Pro Ser Asp Thr Tyr Gly Ala Pro Gly Gly Gly Asn
        115                 120                 125

Gly Asn Gly Gly Arg Pro Ser Ser Tyr Gly Ala Pro Gly Gln Gly
    130                 135                 140

Gln Gly Asn Gly Asn Gly Gly Arg Ser Ser Ser Tyr Gly Ala Pro
145                 150                 155                 160

Gly Gly Gly Asn Gly Gly Arg Pro Ser Asp Thr Tyr Gly Ala Pro Gly
                165                 170                 175

Gly Gly Asn Gly Gly Arg Pro Ser Asp Thr Tyr Gly Ala Pro Gly Gly
            180                 185                 190

Gly Asn Asn Gly Gly Arg Pro Ser Ser Tyr Gly Ala Pro Gly Gly
        195                 200                 205

Gly Asn Gly Gly Arg Pro Ser Asp Thr Tyr Gly Ala Pro Gly Gly Gly
    210                 215                 220

Asn Gly Asn Gly Ser Gly Gly Arg Pro Ser Ser Ser Tyr Gly Ala Pro
225                 230                 235                 240

Gly Gln Gly Gln Gly Gly Phe Gly Gly Arg Pro Ser Asp Ser Tyr Gly
                245                 250                 255

Ala Pro Gly Gln Asn Gln Lys Pro Ser Asp Ser Tyr Gly Ala Pro Gly
            260                 265                 270

Ser Gly Asn Gly Asn Gly Gly Arg Pro Ser Ser Ser Tyr Gly Ala Pro
        275                 280                 285

Gly Ser Gly Pro Gly Gly Arg Pro Ser Asp Ser Tyr Gly Pro Pro Ala
    290                 295                 300

Ser Gly Ser Gly Ala Gly Gly Ala Gly Gly Ser Gly Pro Gly Gly Ala
305                 310                 315                 320

Asp Tyr Asp Asn Asp Glu Pro Ala Lys Tyr Glu Phe Asn Tyr Gln Val
                325                 330                 335

Glu Asp Ala Pro Ser Gly Leu Ser Phe Gly His Ser Glu Met Arg Asp
            340                 345                 350

Gly Asp Phe Thr Thr Gly Gln Tyr Asn Val Leu Leu Pro Asp Gly Arg
        355                 360                 365

Lys Gln Ile Val Glu Tyr Glu Ala Asp Gln Gly Tyr Arg Pro Gln
    370                 375                 380

Ile Arg Tyr Glu Gly Asp Ala Asn Asp Gly Ser Gly Pro Ser Gly Pro
385                 390                 395                 400

Gly Gly Pro Gly Gly Gln Asn Leu Gly Ala Asp Gly Tyr Ser Ser Gly
                405                 410                 415
```

```
Arg Pro Gly Asn Gly Asn Gly Asn Gly Gly Tyr Ser Gly Gly
            420             425             430

Arg Pro Gly Gly Gln Asp Leu Gly Pro Ser Gly Tyr Ser Gly Gly Arg
            435             440             445

Pro Gly Gly Gln Asp Leu Gly Ala Gly Gly Tyr Ser Asn Gly Lys Pro
            450             455             460

Gly Gly Gln Asp Leu Gly Pro Gly Gly Tyr Ser Gly Arg Pro Gly
465             470             475             480

Gly Gln Asp Leu Gly Arg Asp Gly Tyr Ser Gly Arg Pro Gly Gly
                485             490             495

Gln Asp Leu Gly Ala Ser Gly Tyr Ser Asn Gly Arg Pro Gly Gly Asn
            500             505             510

Gly Asn Gly Gly Ser Asp Gly Gly Arg Val Ile Ile Gly Gly Arg Val
            515             520             525

Ile Gly Gly Gln Asp Gly Gly Asp Gln Gly Tyr Ser Gly Gly Arg Pro
530             535             540

Gly Gly Gln Asp Leu Gly Arg Asp Gly Tyr Ser Ser Gly Arg Pro Gly
545             550             555             560

Gly Arg Pro Gly Gly Asn Gly Gln Asp Ser Gln Asp Gly Gln Gly Tyr
                565             570             575

Ser Ser Gly Arg Pro Gly Gln Gly Gly Arg Asn Gly Phe Gly Pro Gly
            580             585             590

Gly Gln Asn Gly Asp Asn Asp Gly Ser Gly Tyr Arg Tyr
            595             600             605

<210> SEQ ID NO 20
<211> LENGTH: 7
<212> TYPE: PRT
<213> ORGANISM: Artificial Sequence
<220> FEATURE:
<223> OTHER INFORMATION: Resilin consensus amino acid sequence repeats
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 20

Ser Xaa Xaa Tyr Gly Xaa Pro
1               5

<210> SEQ ID NO 21
<211> LENGTH: 1848
<212> TYPE: PRT
<213> ORGANISM: Clostridium cellulovorans

<400> SEQUENCE: 21

Met Gln Lys Lys Lys Ser Leu Asn Leu Leu Ala Leu Met Met Val
1               5                   10                  15

Phe Ala Leu Val Leu Pro Ser Ile Pro Ala Leu Ala Ala Thr Ser Ser
            20                  25                  30

Met Ser Val Glu Phe Tyr Asn Ser Asn Lys Ser Ala Gln Thr Asn Ser
            35                  40                  45

Ile Thr Pro Ile Ile Lys Ile Thr Asn Thr Ser Asp Ser Asp Leu Asn
            50                  55                  60

Leu Asn Asp Val Lys Val Arg Tyr Tyr Tyr Thr Ser Asp Gly Thr Gln
```

-continued

```
                65                  70                  75                  80
Gly Gln Thr Phe Trp Cys Asp His Ala Gly Ala Leu Leu Gly Asn Ser
                        85                  90                  95

Tyr Val Asp Asn Thr Ser Lys Val Thr Ala Asn Phe Val Lys Glu Thr
                    100                 105                 110

Ala Ser Pro Thr Ser Thr Tyr Asp Thr Tyr Val Glu Phe Gly Phe Ala
                115                 120                 125

Ser Gly Arg Ala Thr Leu Lys Lys Gly Gln Phe Ile Thr Ile Gln Gly
            130                 135                 140

Arg Ile Thr Lys Ser Asp Trp Ser Asn Tyr Thr Gln Thr Asn Asp Tyr
145                 150                 155                 160

Ser Phe Asp Ala Ser Ser Ser Thr Pro Val Val Asn Pro Lys Val Thr
                    165                 170                 175

Gly Tyr Ile Gly Gly Ala Lys Val Leu Gly Thr Ala Pro Gly Pro Asp
                180                 185                 190

Val Pro Ser Ser Ile Ile Asn Pro Thr Ser Ala Thr Phe Asp Lys Asn
            195                 200                 205

Val Thr Lys Gln Ala Asp Val Lys Thr Thr Met Thr Leu Asn Gly Asn
        210                 215                 220

Thr Phe Lys Thr Ile Thr Asp Ala Asn Gly Thr Ala Leu Asn Ala Ser
225                 230                 235                 240

Thr Asp Tyr Ser Val Ser Gly Asn Asp Val Thr Ile Ser Lys Ala Tyr
                    245                 250                 255

Leu Ala Lys Gln Ser Val Gly Thr Thr Thr Leu Asn Phe Asn Phe Ser
                260                 265                 270

Ala Gly Asn Pro Gln Lys Leu Val Ile Thr Val Val Asp Thr Pro Val
            275                 280                 285

Glu Ala Val Thr Ala Thr Ile Gly Lys Val Gln Val Asn Ala Gly Glu
        290                 295                 300

Thr Val Ala Val Pro Val Asn Leu Thr Lys Val Pro Ala Ala Gly Leu
305                 310                 315                 320

Ala Thr Ile Glu Leu Pro Leu Thr Phe Asp Ser Ala Ser Leu Glu Val
                    325                 330                 335

Val Ser Ile Thr Ala Gly Asp Ile Val Leu Asn Pro Ser Val Asn Phe
                340                 345                 350

Ser Ser Thr Val Ser Gly Ser Thr Ile Lys Leu Leu Phe Leu Asp Asp
            355                 360                 365

Thr Leu Gly Ser Gln Leu Ile Thr Lys Asp Gly Val Phe Ala Thr Ile
        370                 375                 380

Thr Phe Lys Ala Lys Ala Ile Thr Gly Thr Thr Ala Lys Val Thr Ser
385                 390                 395                 400

Val Lys Leu Ala Gly Thr Pro Val Val Gly Asp Ala Gln Leu Gln Glu
                    405                 410                 415

Lys Pro Cys Ala Val Asn Pro Gly Thr Val Thr Ile Asn Pro Ile Asp
                420                 425                 430

Asn Arg Met Gln Ile Ser Val Gly Thr Ala Thr Val Lys Ala Gly Glu
            435                 440                 445

Ile Ala Ala Val Pro Val Thr Leu Thr Ser Val Pro Ser Thr Gly Ile
        450                 455                 460

Ala Thr Ala Glu Ala Gln Val Ser Phe Asp Ala Thr Leu Leu Glu Val
465                 470                 475                 480

Ala Ser Val Thr Ala Gly Asp Ile Val Leu Asn Pro Thr Val Asn Phe
                    485                 490                 495
```

```
Ser Tyr Thr Val Asn Gly Asn Val Ile Lys Leu Leu Phe Leu Asp Asp
            500                 505                 510

Thr Leu Gly Ser Gln Leu Ile Ser Lys Asp Gly Val Phe Val Thr Ile
    515                 520                 525

Asn Phe Lys Ala Lys Ala Val Thr Ser Thr Val Thr Thr Pro Val Thr
        530                 535                 540

Val Ser Gly Thr Pro Val Phe Ala Asp Gly Thr Leu Ala Glu Val Gln
545                 550                 555                 560

Ser Lys Thr Ala Ala Gly Ser Val Thr Ile Asn Ile Gly Asp Pro Ile
                565                 570                 575

Leu Glu Pro Thr Ile Ser Pro Val Thr Ala Thr Phe Asp Lys Lys Ala
            580                 585                 590

Pro Ala Asp Val Ala Thr Thr Met Thr Leu Asn Gly Tyr Thr Phe Asn
        595                 600                 605

Gly Ile Thr Gly Leu Thr Thr Ser Asp Tyr Ser Ile Ser Gly Asn Val
    610                 615                 620

Val Lys Ile Ser Gln Ala Tyr Leu Ala Lys Gln Pro Val Gly Asp Leu
625                 630                 635                 640

Thr Leu Thr Phe Asn Phe Ser Asn Gly Asn Lys Thr Ala Thr Ala Lys
                645                 650                 655

Leu Val Val Ser Ile Lys Asp Ala Pro Lys Thr Val Thr Ala Thr Val
            660                 665                 670

Gly Thr Ala Thr Val Asn Ala Gly Glu Thr Val Ala Val Pro Val Thr
        675                 680                 685

Leu Ser Asn Val Ser Gly Ile Ser Thr Ala Glu Leu Gln Leu Ser Phe
    690                 695                 700

Asp Ala Thr Leu Leu Glu Val Val Ser Ile Thr Ala Gly Asp Ile Val
705                 710                 715                 720

Leu Asn Pro Ser Val Asn Phe Ser Ser Val Asn Gly Ser Thr Ile
                725                 730                 735

Lys Leu Leu Phe Leu Asp Asp Thr Leu Gly Ser Gln Leu Ile Ser Lys
            740                 745                 750

Asp Gly Val Phe Ala Thr Ile Asn Phe Lys Ala Lys Ser Val Thr Ser
        755                 760                 765

Thr Val Thr Thr Pro Val Lys Val Ser Gly Thr Pro Val Phe Ala Asp
    770                 775                 780

Gly Thr Leu Ala Glu Leu Ser Tyr Glu Thr Val Ala Gly Ser Val Thr
785                 790                 795                 800

Ile Asn Ala Ile Gly Pro Val Lys Thr Val Thr Ala Thr Val Gly Thr
                805                 810                 815

Ala Thr Val Lys Ser Gly Glu Thr Val Ala Val Pro Val Thr Leu Ser
            820                 825                 830

Asn Val Pro Gly Ile Ala Thr Ala Glu Leu Gln Leu Ser Phe Asp Ala
        835                 840                 845

Thr Leu Leu Glu Val Ala Ser Ile Thr Val Gly Asp Ile Val Leu Asn
    850                 855                 860

Pro Ser Val Asn Phe Ser Ser Val Val Asn Gly Ser Thr Ile Lys Leu
865                 870                 875                 880

Leu Phe Leu Asp Asp Thr Leu Gly Ser Gln Leu Ile Ser Lys Asp Gly
                885                 890                 895

Val Leu Ala Thr Ile Asn Phe Lys Ala Lys Thr Val Ser Thr Val
            900                 905                 910
```

```
Thr Thr Pro Val Ala Val Ser Gly Thr Pro Val Phe Ala Asp Gly Thr
            915                 920                 925

Leu Ala Glu Leu Gln Ser Lys Thr Val Ala Gly Ser Val Thr Ile Glu
    930                 935                 940

Pro Ser Gln Pro Val Lys Thr Val Thr Ala Thr Val Gly Thr Ala Thr
945                 950                 955                 960

Val Lys Ser Gly Glu Thr Val Ala Val Pro Val Thr Leu Ser Asn Val
                965                 970                 975

Pro Gly Ile Ala Thr Ala Glu Leu Gln Val Gly Phe Asp Ala Thr Leu
            980                 985                 990

Leu Glu Val Ala Ser Ile Thr Val Gly Asp Ile Val Leu Asn Pro Ser
    995                 1000                1005

Val Asn Phe Ser Ser Val Val Asn Gly Ser Thr Ile Lys Leu Leu
    1010                1015                1020

Phe Leu Asp Asp Thr Leu Gly Ser Gln Leu Ile Ser Lys Asp Gly
    1025                1030                1035

Val Leu Ala Thr Ile Asn Phe Lys Ala Lys Thr Val Thr Ser Lys
    1040                1045                1050

Val Thr Thr Pro Val Ala Val Ser Gly Thr Pro Val Phe Ala Asp
    1055                1060                1065

Gly Thr Leu Ala Glu Leu Asn Met Lys Thr Val Ala Gly Ser Val
    1070                1075                1080

Thr Ile Glu Pro Ser Gln Pro Val Lys Thr Val Thr Ala Thr Val
    1085                1090                1095

Gly Thr Ala Thr Val Lys Ser Gly Glu Thr Val Ala Val Pro Val
    1100                1105                1110

Thr Leu Ser Asn Val Pro Gly Ile Ala Thr Ala Glu Leu Gln Val
    1115                1120                1125

Gly Phe Asp Ala Thr Leu Leu Glu Val Ala Ser Ile Thr Val Gly
    1130                1135                1140

Asp Ile Val Leu Asn Pro Ser Val Asn Phe Ser Ser Val Val Asn
    1145                1150                1155

Gly Ser Thr Ile Lys Leu Leu Phe Leu Asp Asp Thr Leu Gly Ser
    1160                1165                1170

Gln Leu Ile Ser Lys Asp Gly Val Leu Ala Thr Ile Asn Phe Lys
    1175                1180                1185

Ala Lys Thr Val Thr Ser Lys Val Thr Thr Pro Val Ala Val Ser
    1190                1195                1200

Gly Thr Pro Val Phe Ala Asp Gly Thr Leu Ala Glu Leu Lys Tyr
    1205                1210                1215

Glu Thr Val Ala Gly Ser Val Thr Ile Glu Pro Ser Gln Pro Val
    1220                1225                1230

Lys Thr Val Thr Ala Thr Val Gly Thr Ala Thr Gly Lys Val Gly
    1235                1240                1245

Glu Thr Val Ala Val Pro Val Thr Leu Ser Asn Val Pro Gly Ile
    1250                1255                1260

Ala Thr Ala Glu Val Gln Val Gly Phe Asp Ala Thr Leu Leu Glu
    1265                1270                1275

Val Ala Ser Ile Thr Ala Gly Asp Ile Val Leu Asn Pro Ser Val
    1280                1285                1290

Asn Phe Ser Ser Val Val Asn Gly Ser Thr Ile Lys Ile Leu Phe
    1295                1300                1305

Leu Asp Asp Thr Leu Gly Ser Gln Leu Ile Ser Lys Asp Gly Val
```

```
            1310                1315                1320

Phe Ala Thr Ile Asn Phe Lys Ile Lys Ala Val Pro Ser Thr Gly
            1325                1330                1335

Thr Thr Pro Val Ala Ile Ser Gly Thr Pro Val Phe Ala Asp Gly
            1340                1345                1350

Thr Leu Ala Glu Val Gln Tyr Lys Thr Val Ala Gly Ser Val Thr
            1355                1360                1365

Ile Ala Ala Asp Ile Lys Ala Val Lys Ala Thr Val Gly Thr
            1370                1375                1380

Ala Thr Gly Lys Ala Gly Asp Thr Val Ala Val Pro Val Thr Leu
            1385                1390                1395

Ser Asn Val Ser Gly Ile Ala Thr Val Glu Leu Gln Leu Ser Phe
            1400                1405                1410

Asp Ala Thr Leu Leu Glu Val Ala Ser Ile Thr Ala Gly Asp Ile
            1415                1420                1425

Val Leu Asn Pro Ser Val Asn Phe Ser Ser Val Asn Gly Ser
            1430                1435                1440

Thr Ile Lys Ile Leu Phe Leu Asp Asp Thr Leu Gly Ser Gln Leu
            1445                1450                1455

Ile Ser Lys Asp Gly Val Phe Ala Thr Val Asn Phe Lys Val Lys
            1460                1465                1470

Ser Thr Ala Thr Asn Ser Ala Val Thr Pro Val Thr Val Ser Gly
            1475                1480                1485

Thr Pro Val Phe Ala Asp Gly Thr Leu Ala Glu Leu Lys Ser Glu
            1490                1495                1500

Ser Ala Ala Gly Arg Leu Thr Ile Leu Pro Thr Val Ile Ile Val
            1505                1510                1515

Asp Ser Thr Val Ala Pro Thr Ala Val Thr Phe Asp Lys Ala Asn
            1520                1525                1530

Gln Ala Asp Ala Ala Ile Thr Met Thr Leu Asn Gly Asn Thr Phe
            1535                1540                1545

Ser Ala Ile Lys Asn Gly Thr Ala Thr Leu Val Lys Gly Thr Asp
            1550                1555                1560

Tyr Thr Val Ser Glu Asn Val Val Thr Ile Ser Lys Ala Tyr Leu
            1565                1570                1575

Ala Lys Gln Thr Gly Thr Val Thr Leu Glu Phe Val Phe Asp Lys
            1580                1585                1590

Gly Asn Ser Ala Lys Val Val Ala Val Lys Glu Ile Gln Ile
            1595                1600                1605

Val Asn Ser Thr Ile Thr Pro Val Val Ala Thr Phe Glu Lys Thr
            1610                1615                1620

Ala Ala Lys Gln Ala Asp Val Val Val Thr Met Ser Leu Asn Gly
            1625                1630                1635

Asn Thr Phe Ser Ala Ile Lys Asn Gly Thr Thr Leu Val Lys
            1640                1645                1650

Gly Thr Asp Tyr Thr Ile Ser Gly Ser Thr Val Thr Ile Ser Lys
            1655                1660                1665

Ala Tyr Leu Ala Thr Leu Ala Asp Gly Ser Ala Thr Leu Glu Phe
            1670                1675                1680

Val Phe Asn Gln Gly Ala Ser Ala Lys Leu Arg Leu Thr Ile Val
            1685                1690                1695

Pro Ala Val Val Asp Pro Val Val Thr Asp Phe Ala Val Lys Ile
            1700                1705                1710
```

-continued

```
Asp Lys Val Ser Ala Ala Ala Gly Ser Thr Val Lys Val Pro Val
    1715            1720            1725

Ser Leu Ile Asn Val Ser Lys Val Gly Asn Val Cys Val Ala Glu
    1730            1735            1740

Tyr Lys Ile Ser Phe Asp Ser Ser Val Leu Thr Tyr Val Gly Thr
    1745            1750            1755

Thr Ala Gly Thr Ser Ile Lys Asn Pro Ala Val Asn Phe Ser Ser
    1760            1765            1770

Gln Leu Asn Gly Asn Thr Ile Thr Leu Leu Phe Phe Asp Asn Thr
    1775            1780            1785

Ile Gly Asn Glu Leu Ile Thr Ala Asp Gly Gln Phe Ala Thr Ile
    1790            1795            1800

Glu Phe Lys Val Asn Ala Ala Ala Thr Ser Gly Thr Thr Ala Glu
    1805            1810            1815

Val Lys Val Ala Thr Ile Ser Ser Phe Ala Asp Ala Ser Leu Thr
    1820            1825            1830

Glu Ile Thr Lys Val Ala Thr Val Asn Gly Ser Val Lys Val Ser
    1835            1840            1845
```